(12) United States Patent
Nishimura et al.

(10) Patent No.: US 9,139,607 B2
(45) Date of Patent: Sep. 22, 2015

(54) METHOD OF PURIFYING/CONCENTRATING SUGAR CHAIN WITH SUGAR CHAIN-TRAPPING MOLECULE AND METHOD OF ANALYZING SUGAR CHAIN STRUCTURE

(75) Inventors: Shinichiro Nishimura, Sapporo (JP); Kenichi Niikura, Sapporo (JP); Hiroaki Nakagawa, Sapporo (JP); Minenobu Okayama, Toride (JP)

(73) Assignee: Sumitomo Bakelite Co., Ltd., Tokyo (JP)

( * ) Notice: Subject to any disclaimer, the term of this patent is extended or adjusted under 35 U.S.C. 154(b) by 2339 days.

(21) Appl. No.: 10/540,723

(22) PCT Filed: Dec. 25, 2003

(86) PCT No.: PCT/JP03/16841
§ 371 (c)(1),
(2), (4) Date: Apr. 19, 2006

(87) PCT Pub. No.: WO2004/058687
PCT Pub. Date: Jul. 15, 2004

(65) Prior Publication Data
US 2006/0188996 A1    Aug. 24, 2006

(30) Foreign Application Priority Data
Dec. 26, 2002  (JP) ................. 2002-378733

(51) Int. Cl.
*C07H 1/08* (2006.01)
*C07C 239/20* (2006.01)
(52) U.S. Cl.
CPC ............... *C07H 1/08* (2013.01); *C07C 239/20* (2013.01)
(58) Field of Classification Search
CPC .............................. C07C 239/20; C07H 1/08
USPC ............... 544/106; 558/232; 564/17, 18, 301
See application file for complete search history.

(56) References Cited

U.S. PATENT DOCUMENTS

| 2,723,972 | A | * | 11/1955 | Herrick et al. ............... 562/556 |
| 5,334,761 | A | * | 8/1994 | Gebeyehu et al. ............ 564/197 |
| 5,514,505 | A | * | 5/1996 | Limburg et al. ............... 430/41 |
| 6,376,663 | B1 | | 4/2002 | Williams et al. |

FOREIGN PATENT DOCUMENTS

| CN | 1087554 | A | | 6/1994 |
| EP | 0 399 464 | A2 | | 11/1990 |
| JP | 58-53757 | | | 3/1983 |
| JP | 60-163667 | | | 8/1985 |
| JP | 62-228273 | | | 10/1987 |
| JP | 3-73852 | | | 3/1991 |
| JP | 05-261281 | A | | 10/1993 |
| JP | 11-209389 | A | | 8/1999 |
| JP | 2000-502062 | A | | 2/2000 |
| JP | 2001-89494 | | | 4/2001 |
| WO | 96/41813 | | * | 12/1996 |
| WO | WO96/41813 | | * | 12/1996 |
| WO | 01/55160 | A1 | | 8/2001 |
| WO | 02/057422 | A2 | | 7/2002 |
| WO | 03/084634 | A1 | | 10/2003 |

OTHER PUBLICATIONS

CAS Registry, CAS No. 4297-70-5.*
Rydon et al, "Polypeptides. Part XII. The Synthesis and Oxidation of L-Cysteinyl-6-aminohexanoyl-L-cysteine and L-Cysteinyl-11-amino-undecanoyl-L-cytsteine," Journal of the Chemical Society (Aug. 1965), 4246-53.*
Guillier et al., "Linkers and Cleavage Strategies in Solid-Phase Organic Synthesis and Combinatorial Chemistry," Chem. Rev. 100, 2091-2157, 2000.*
CAS Registry No. 152417-88-4 (Entered in STN Jan. 21, 1994).*
CAS Registry No. 22004-70-2 (Entered in STN Nov. 16, 1984).*
CAS Registry No. 150013-38-0 (Entered in STN Sep. 15, 1993).*
Lee et al., "Development of Tripeptidyl Farnesyltransferase Inhibitors," Bioorganic & Medicinal Chemistry Letters, 12, 1599-1602, 2002.*
CAS Registry No. 97686-20-9 (Entered in STN Aug. 18, 1985).*
Guillaumie et al., "Immobilization of Pectin Fragments on Solid Supports: Novel Coupling by Thiazolidine Formation," *Bioconjugate Chem.* 13:285-294, 2002.

* cited by examiner

*Primary Examiner* — Paul A Zucker
*Assistant Examiner* — Mark Luderer
(74) *Attorney, Agent, or Firm* — Seed IP Law Group, PLLC

(57) ABSTRACT

The present invention provides substance which can specifically interact with sugar chains. Further, the present invention provides a method for separating, concentrating, or purifying sugar chains or a sugar chain-containing substance in a sample, comprising the steps of: a) contacting a sugar chain-trapping carrier comprising a substance which can specifically interact with sugar chains with the sample in a fluid phase under conditions that the sugar chain-trapping carrier can react with the sugar chains or sugar chain-containing substance; b) isolating a composite of the sugar chain-trapping carrier and the sugar chains or sugar chain-containing substance from the fluid phase; and c) exposing the composite to the conditions that the interaction between the sugar chain-trapping carrier and the sugar chains or sugar chain-containing substance is at least partially eliminated.

5 Claims, 16 Drawing Sheets

Scheme 1: Synthesis path to photopolymerizable
hydroxylamino derivative

FIG.7

| Peak number | Sugar chain structure | Proportion (%) |
|---|---|---|
| 1 | GNβ1, 2-Mα1, 6 \\ Fα1, 6<br>　　　　　　　　Mβ1, 4-GNβ1, 4-GN<br>GNβ1, 2-Mα1, 3 / | 19 |
| 2 | Gβ1, 3-GNβ1, 2-Mα1, 6 \\ Fα1, 6<br>　　　　　　　　Mβ1, 4-GNβ1, 4-GN<br>GNβ1, 2-Mα1, 3 / | 22 |
| 3 | GNβ1, 2-Mα1, 6 \\ Fα1, 6<br>　　　　　　　　Mβ1, 4-GNβ1, 4-GN<br>Gβ1, 3-GNβ1, 2-Mα1, 3 / | 15 |
| 4 | Gβ1, 3-GNβ1, 2-Mα1, 6 \\ Fα1, 6<br>　　　　　　　　Mβ1, 4-GNβ1, 4-GN<br>Gβ1, 3-GNβ1, 2-Mα1, 3 / | 28 |
| 5 | GNβ1, 2-Mα1, 6 \\ Fα1, 6<br>　　　GNβ1, 4-Mβ1, 4-GNβ1, 4-GN<br>GNβ1, 2-Mα1, 3 / | 4 |
| 6 | Gβ1, 3-GNβ1, 2-Mα1, 6 \\ Fα1, 6<br>　　　GNβ1, 4-Mβ1, 4-GNβ1, 4-GN<br>GNβ1, 2-Mα1, 3 /<br>及び<br>GNβ1, 2-Mα1, 6 \\ Fα1, 6<br>　　　GNβ1, 4-Mβ1, 4-GNβ1, 4-GN<br>Gβ1, 3-GNβ1, 2-Mα1, 3 / | 7 |
| 7 | Gβ1, 3-GNβ1, 2-Mα1, 6 \\ Fα1, 6<br>　　　GNβ1, 4-Mβ1, 4-GNβ1, 4-GN<br>Gβ1, 3-GNβ1, 2-Mα1, 3 / | 5 |

METHOD OF PURIFYING/CONCENTRATING SUGAR CHAIN WITH SUGAR CHAIN-TRAPPING MOLECULE AND METHOD OF ANALYZING SUGAR CHAIN STRUCTURE

TECHNICAL FIELD

The present invention generally relates to a substance which can be used for separating, concentrating, purifying, and analyzing sugar chains or a sugar chain-containing substance (for example, glycoproteins and glycolipids). The present invention also relates to a method, an apparatus, and a system for separating, concentrating, purifying, and analyzing (by a mass spectrometry method, for example) sugar chains or sugar chain-containing substances using such a substance. The present invention further relates to a medicine (for example, vaccine), a reagent, a sugar chain array, using a sugar chain composition purified by the method according to the present invention. The present invention further relates to a method for diagnosing, treating, differentiating, and using a sugar chain composition purified by the method according to the present invention.

BACKGROUND ART

Sugar chain is a generic term including glucose, galactose, mannose, fucose, xylose, N-acetylglucosamine, N-acetylgalactosamine, sialic acid, and molecules in which monosaccharides, which are derivatives thereof, are linked by glycosidic bonds. Sugar chains encompass a wide variety of substances and are involved in various functions of living organisms. Analysis of sugar chains by electrophoresis is widely known as a technique for studying functions or analyzing structures or the like of sugar chains (see, for example, Japanese National Phase PCT Laid-open Publication No. 5-500563). This method visualizes the migration patterns of the sugar chain for analysis.

A method of transferring sugar chains from an electrophoresis gel to a film using a semidry blot transfer device is also known (see, for example, Japanese National Phase PCT Laid-open Publication No. 5-503146). In this method, sugar chains separated by electrophoresis are further transferred to a film of negative charge derivatives etc. of PVDF (polyvinylidene difluoride) after fluorescence detection in order to analyze the sugar chains on the film. In this way, it is possible to examine sugar chains, which react with a lectin or an antibody only when these are bound to proteins or lipids, by reacting the sugar chains with a lectin or an antibody without being influenced by a protein or a lipid, by transferring the sugar chains to the film. It is also possible to liberate a sugar chain band from the film, and apply mass spectrometry to the sugar chains. However, in this method, transfer is performed by electrophoretic transfer. Thus, charged sugar chains readily pass to the film, and as a result, the amount of transferred sugar chains is small. Therefore, the method is not suitable for precise quantitative determination and analysis.

Sugar chains of complex carbohydrates which widely exist in nature are important components of living bodies, and it is becoming evident that these play an important role in interactions between cells. Thus, various techniques for analyzing a small amount of sugar chain structures have been developed. In these techniques, steps of liberating sugar chains, separating and purifying sugar chains, labeling sugar chains and the like are combined as appropriate. However, such steps require cumbersome processes. Particularly, a separation and purification process for the sugar chains included in a mixture in a small amount after liberation is difficult and requires a great deal of experience. Generally used methods include ion exchange resin, reverse-phase chromatography, active carbon, gel filtration chromatography, and the like. However, these separation methods are not methods for specifically recognizing a sugar. Thus, contamination with other components (such as peptides or proteins) is considerable. Further, the recovery rate varies depending upon the structures of the sugar chains. Finally, identification by NMR spectrum or MS spectrum is required in order to gain reliable information on the obtained sugar. Particularly, a method using MS spectrums is an effective method for sugar chain analysis because identification of a molecular weight is possible with a small amount in the order of nanograms to micrograms. Methods which can determine sugar chain structures conveniently without using MS are also proposed.

Methods for analyzing sugar chain structures of glycoproteins and the like include a method for analyzing sugar chain structures of an unknown sample by utilizing the principle that, when a sugar chain of a glycoprotein is liberated and then separated and analyzed using liquid chromatography, an elution behavior according to the sugar chain structure thereof is observed by comparing the elution behavior with the elution behavior of known sugar chains. Generally used methods include ion exchange resin, reverse-phase chromatography, active carbon, gel filtration chromatography, and the like. However, these separation methods are not methods for specifically recognizing a sugar. Thus, contamination by other components (such as peptides or proteins) is considerable. Further, recovery rates vary depending upon the structures of the sugar chains. Moreover, identification by NMR spectrums or MS spectrums is required in order to confirm the structure. Particularly, a method using MS spectrums is an effective method for sugar chain analysis because identification of a molecular weight is possible with a small amount in the order of nanograms to micrograms. Methods which can determine sugar chain structures conveniently without using MS are also proposed.

Methods in which high performance liquid chromatography (HPLC) is applied also exist. Such methods include methods by two-dimensional HPLC (see, for example, Anal. Biochem., 171, 73 (1988) Tomitani et al.) in which HPLC of two types of modes are combined, and a method in which a sample is treated beforehand with a mixed enzyme series such as exoglycosidase and the like, and the treated sample is analyzed by HPLC for determining the structure of the sugar chain (see, for example, Chemistry and Living Organism 32 (10) 661 (1994), Konishi et al.). In these methods, sugar chains can be detected by performing a sugar chain-selective chemical reaction, and fluorescein-labelling sugar chains. In both methods, the sugar chain structure is determined based on the holding period depicted in the HPLC chromatogram. On the other hand, an analysis method employing a column in which a lectin having sugar recognition capability is fixed (see, for example, Anal. Biochem., 164, 374 (1987) Harada et al.) is also reported.

However, an analysis method employing a method of HPLC has the following problems: (1) only one sample is analyzed at a time, thus many numbers of samples cannot be analyzed at the same time; (2) condition settings for HPLC are delicate and holding periods may deviate and are likely to be incorrect; (3) HPLC when combined with a post-column reactor or a pre-column reactor consume a large amount of reagent (4) when a lectin fixed column is used, adsorbing glycopeptide may be affected by a change in affinity of the lectin to the sugar; and (5) sugar chains have to be labeled by fluorescein, radio isotopes, or the like, thereby requiring time and effort.

Further, a method for analyzing by fixing sugar chains to a solid phase has been attempted. However, fixing sugar chains which have high hydrophilicity is technically difficult. Thus, methods for directly fixing sugar chains are proposed. Such methods include, for example, a method for fixing to an amino plate by an acid amide bond utilizing reducing terminals of the sugar chains (see, for example, O'Shannessy et al., Anal. Chemistry, 1990, 91, 1-8), highly polymerizing sugar chains in order to give hydrophobicity to sugar chains themselves and adsorbing to a plate (see, for example, Japanese Laid-Open Publication No. 62-212568), and a method in which the sugar chains are biotinylated and the sugar chains are fixed to a solid phase to which avidin is bound by utilizing strong affinity between the avidin and the biotin.

However, the method in which sugar chains are fixed to a solid phase such as plates, has the problem that fixing yield is lowered, operations become cumbersome, and a long time is required due to pre-treatment of the sugar chains and fixing using a condensation agent, and that non-specific adsorption tends to occur due to coexistence of contaminants. Recently, a method for analyzing sugar chains by an analysis method employing surface plasmon resonance was proposed. However, since expensive specific equipment is used, it is difficult to obtain wide-use.

There are some examples reported about a method in which sugar chains are oxidized using enzymes such as galactose oxidase, and then coupled to a solid substrate to which hydrazide groups are introduced, such as cellulose, gel, or the like. (see, for example, O'Shannessy et al., Anal. Chemistry, 1990, 91, 1-8). In this method, there is a process of oxidizing sugar chains, which requires additional effort. Further, if the sugar chains are not oxidized, cellulose or gel to which hydrazide groups are introduced does not react sufficiently. The reaction varies depending on the sugar chains. Sometimes, the reaction does not occur at all depending on a type of sugar chains.

A convenient method for organic synthesis of glycopeptide has been reported (see, for example, Stefano E. Cervigni, Pascal Dumy, Manfred Mutter Angew. Chem. Int. Ed. Engl., 1996, 35, 1230-1232). However, chemical reactions utilizing specificity for sugar chains, which are used in this method, are intended for obtaining a product of a novel sugar chain cointegrate. There is no reported example on a carrier material specific to sugar chains targeting separation, purification and analysis of unknown sugar chain samples. Moreover, the peptide used in this method can be attached to a solid support and the like, but the form of the reaction is adsorption, and no phase transition occurs. This means that the peptide attached in this example are not bound to a solid support. Thus, when the attached peptides are exposed to a large amount of excessive solvent, they are liberated. Therefore, it is substantially impossible to perform purification, separation, analysis and the like even when the peptide used in this method is used. It is also impossible to produce a device which requires strong bonds to a support, such as a sugar chain chip.

As described above, a technique which enables one to directly separate and analyze sugar chains, irrespective of the types thereof, still does not exist. Such a technique is very important and desirable in the post-genomics and post-proteomics era.

The objective of the present invention is to provide a substance which can specifically bind to sugar chains irrespective of the type of the sugar chains. Another objective of the present invention is to provide a method for separating, purifying, concentrating or analyzing sugar chains or sugar chain-containing substances, efficiently and/or in faithful accordance with the state in nature, and a system and apparatus used therefor. Yet another object of the present invention is to utilize sugar chain components which naturally exist in a sample in a form where the ratio of content reflected.

DISCLOSURE OF THE INVENTION

The problems as described above related to the present invention have been resolved by providing a substance which can specifically bind to sugar chains. The substance solves substantially all the above-described problems, since it preferably has no difference with respect to sugar chains.

Therefore, the present invention provides a method for efficiently fixing sugar chains derived from complex carbohydrates of a biological sample to a high molecular carrier in an aqueous solution in one stage or two stages, conveniently fractionating a sugar chain composition, and efficiently determining the sugar chain structure. According to the method of the present invention, a series of reactions necessary for analysis can be performed efficiently using conventional detection equipment. Sugar chains which can be fractionated according to the method of the present invention may be sugar chains present on an outermost surface of a cell membrane, sugar chains of a mass of tissue or segments thereof, and sugar chains of bacteria, virus and the like. According to the methods of the present invention, pre-treatment required for such analysis can be efficiently performed. Further, a number of samples of a small amount can be treated without requiring skill.

In one embodiment, the method of the present invention is a sugar chain separation method and/or purification method and/or concentration method comprising the following novel steps: a) binding sugar chains to a reactive carrier in water and/or a water-containing organic solvent and/or an organic solvent; b) separating the sugar chains and the carrier which are bound in step a) from a liquid phase; and c) substantially separating the sugar chains from the liquid phase by cleaving the compound separated in step b) chemically or physically, or by using enzymes, in which a functional group of the reactive carrier is a hydroxylamino group, N-alkyl hydroxylamino group, hydrazide group, thiosemicarbazide group and cysteine residue.

As described above, the present invention provides the following things.

(1) A substance which can specifically interact with sugar chains.

(2) A substance according to item 1, wherein the substance has an interaction level to the sugar chains substantially higher than interaction levels of all the substances which do not include sugar chains.

(3) A substance according to item 1, specifically interacting with any sugar chains at a predetermined level or higher.

(4) A substance according to item 1, wherein the substance maintains specific interactions with at least a certain amount of sugar chains when the substance is exposed to conditions that dissociate the non-specific interactions with substances other than sugar chains.

(5) A substance according to item 1, wherein a level of interaction between the substance and the sugar chains is such that a necessary dissociation energy when laser irradiation is performed in a MALDI-TOF is at least 5 eV.

(6) A substance according to item 1, which can specifically interact with any sugar chain at a level within the range having the maximum value 10 times the minimum value or smaller.

(7) A substance according to item 1, wherein the sugar chains include oxidized sugar chains and sugar chains which are not oxidized.

(8) A substance according to item 1, which is bindable to a support.

(9) A substance according to item 8, wherein at least part of the support and substance may experience phase transition.

(10) A substance according to item 8, wherein the support is solid at room temperature.

(11) A substance according to item 1, which is useable as a support.

(12) A substance according to item 1, wherein the substance comprises a functional group which can react with an aldehyde group in a fluid.

(13) A substance according to item 12, wherein the fluid includes substantially no substance including a keto group.

(14) A substance according to item 12, wherein the fluid is selected from a group consisting of aqueous solution, organic solvent and the mixture thereof.

(15) A substance according to item 12, wherein the fluid phase includes an aqueous solution.

(16) A substance according to item 12, wherein the functional group is selected from a group consisting of a hydroxylamino group, a N-alkylhydroxylamino group, a hydrazide group, a thiosemicarbazide group and a cysteine residue.

(17) A substance according to item 1, wherein the interaction comprises a covalent bond.

(18) A substance according to claim 1, wherein the interaction comprises oxime bond, hydrazone bond, thiosemihydrazone bond, perhydrothiazine ring formation or thiazolidine ring formation.

(19) A substance according to claim 1, represented by formula (I): X—Y—Z (I)

[herein, X is a group represented by formulae:

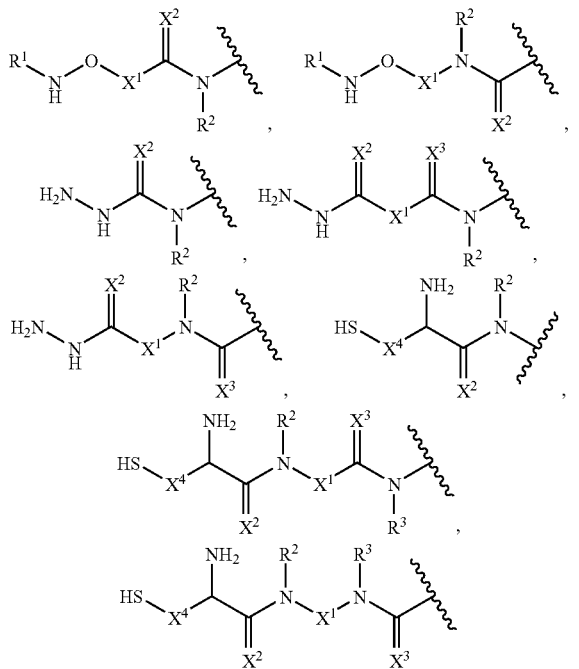

(herein, $X^1$ is alkylene which may be substituted or alkenylene which may be substituted, $X^2$ is an oxygen atom or a sulfur atom, $X^3$ is an oxygen atom or a sulfur atom, $X^4$ is methylene or ethylene, $R^1$ is a hydrogen atom or alkyl, and $R^2$ and $R^3$ are independently a hydrogen atom or alkyl);

Y is single bond; optionaly substituted alkylene in which at least one group selected from the group consisting —O—, —S—, —S—S—, —N($R^a$)—C(=O)—, —C(=O)—N($R^b$)—, and phenylene which may be substituted, may intervene; or optionaly substituted alkenylene in which at least one group selected from the group consisting —O—, —S—, —S—S—, —N($R^a$)—C(=O)—, —C(=O)—N($R^b$)—, and phenylene which may be substituted, may intervene (herein, $R^a$ and $R^b$ are independently a hydrogen atom or alkyl):

Z is a group represented by formulae:

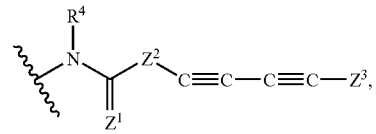

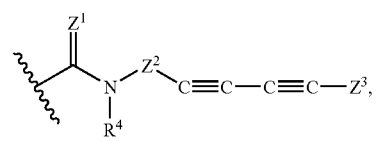

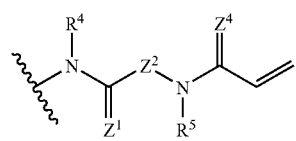

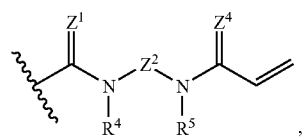

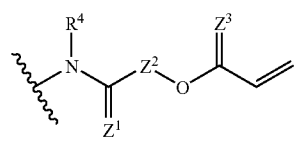

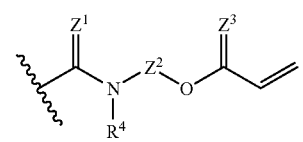

(herein, $Z^1$ is an oxygen atom or sulfur atom, $Z^2$ and $Z^3$ are independently optionaly substituted alkylene in which phenylene may intervene, or optionaly substituted alkenylene in which phenylene may intervene, $Z^4$ is an oxygen atom or a sulfur atom, $R^4$ and $R^5$ are independently a hydrogen atom or alkyl)].

(20) A substance obtained by polymerizing the substance according to item 19.

(21) A substance according to item 20, wherein the polymerization is initiated by UV-irradiation.

(22) A substance according to item 20, obtained by polymerizing a monolayer obtained by physical adsorption of Z site of the compound represented by formula (I) to a support.

(23) A substance according to item 1, which is a copolymer obtained by polymerizing a compound represented by formula (I): X—Y—Z (I)

[herein, X is a group represented by formulae:

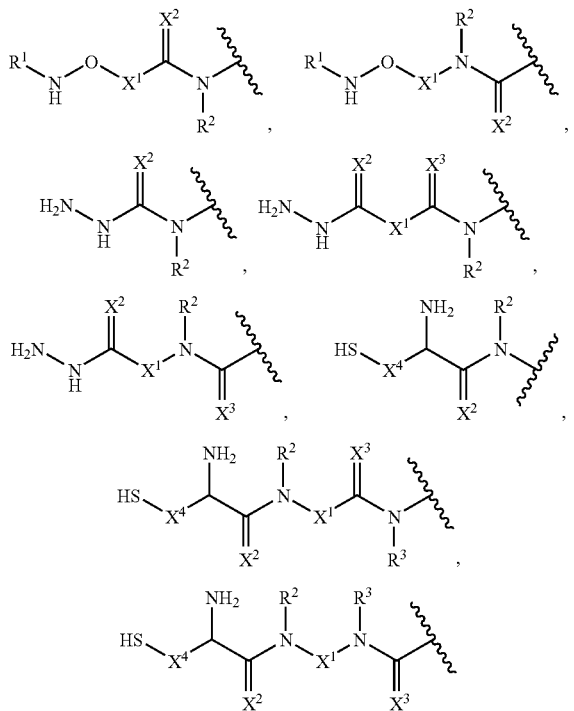

(herein, $X^1$ is alkylene which may be substituted or alkenylene which may be substituted, $X^2$ is an oxygen atom or a sulfur atom, $X^3$ is an oxygen atom or a sulfur atom, $X^4$ is methylene or ethylene, $R^1$ is a hydrogen atom or alkyl, and $R^2$ and $R^3$ are independently a hydrogen atom or alkyl);

Y is single bond; optionaly substituted alkylene in which at least one group selected from the group consisting —O—, —S—, —S—S—, —N($R^a$)—C(=O)—, —C(=O)—N($R^b$)—, and phenylene which may be substituted, may intervene; or optionaly substituted alkenylene in which at least one group selected from the group consisting —O—, —S—, —S—S—, —N($R^a$)—C(=O)—, —C(=O)—N($R^b$)—, and phenylene which may be substituted, may intervene (herein, $R^a$ and $R^b$ are independently a hydrogen atom or alkyl);

Z is a group represented by formulae:

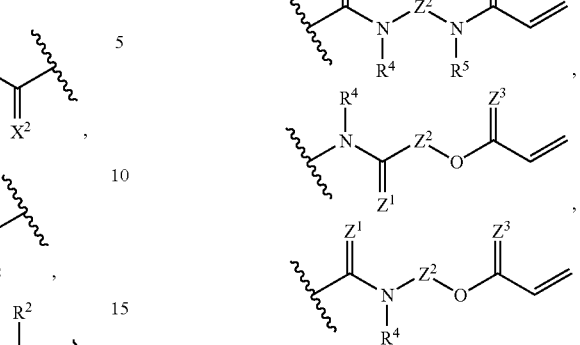

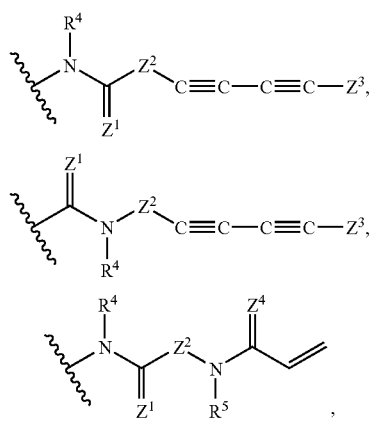

-continued

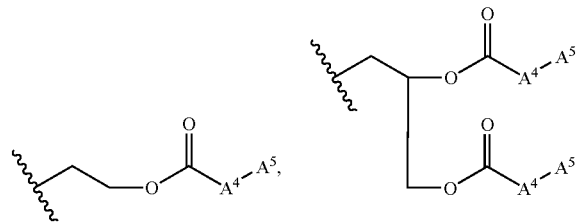

(herein, $Z^1$ is an oxygen atom or sulfur atom, $Z^2$ and $Z^3$ are independently optionaly substituted alkylene in which phenylene may intervene, or optionaly substituted alkenylene in which phenylene may intervene, $Z^4$ is an oxygen atom or a sulfur atom, $R^4$ and $R^5$ are independently a hydrogen atom or alkyl)]; and a compound represented by formula (II): $A^1$-$A^2$(II)

[herein, $A^1$ is H(OCH$_2$CH$_2$)$_n$O— (n is an integer from 1 to 5) or a group represented by a formula:

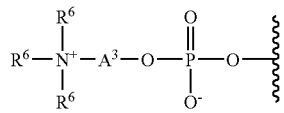

(herein, $A^3$ is alkylene, and $R^6$ is alkyl); and
$A^2$ is a group represented by formulae:

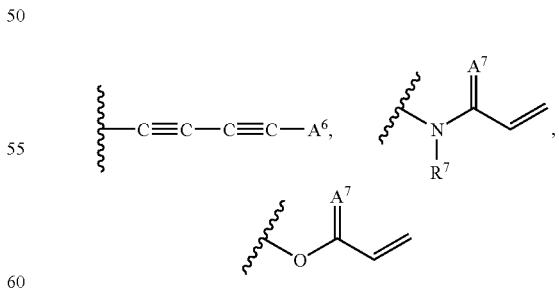

(herein, $A^4$ is alkylene, and As is represented by formulae:

[formulae shown]

($A^6$ is alkylene, $A^7$ is an oxygen atom or a sulfur atom, and $R^7$ is a hydrogen atom or alkyl))].

(24) A substance according to item 23, wherein the polymerization is initiated by UV-irradiation.

(25) A substance according to item 23, wherein mole fraction of the compound represented by formula (II) is 0.1 to 0.9.

(26) A substance according to item 23, obtained by polymerizing monolayers obtained by physical adsorption of Z site of the compound represented by formula (I) and $A^2$ site of the compound represented by formula (II) to a support.

(27) A substance according to item 23, obtained by polymerizing water dispersion or a cast film of a mixture comprising the compound represented by formula (I) and the compound represented by formula (II).

(28) A lipid including a functional group which can react with an aldehyde group in a fluid.

(29) A sugar chain-trapping carrier, comprising a substance which can specifically interact with sugar chains.

(30) A sugar chain-trapping carrier according to item 29, further comprising a support.

(31) A sugar chain-trapping carrier, in which the substance according to item 20 or 23 is transferred to a support.

(32) A sugar chain-trapping carrier according to item 30, wherein the support is a cross-linked polymer or lipid film.

(33) A sugar chain-trapping carrier according to item 30, wherein the support includes a photopolymerizable lipid derivative.

(34) A sugar chain-trapping carrier according to item 30, wherein the support is an insoluble in organic solvent.

(35) A sugar chain-trapping carrier according to item 30, wherein the support is a self-closed lipid film.

(36) A sugar chain-trapping carrier according to item 33, wherein the photopolymerizable lipid derivative has a diacetylene represented by formula 1-C—C—C≡C—.

(37) A sugar chain-trapping carrier according to item 36, wherein the photopolymerizable lipid derivative is polymerized by ultraviolet ray.

(38) A sugar chain-trapping carrier according to item 30, wherein the support is two-dimensionally extended.

(39) A sugar chain-trapping carrier according to item 38, wherein the support is a cast film or monolayer.

(40) A method for synthesizing a substance which can specifically interact with sugar chains, comprising the steps oft
  A) providing a functional group which can react with an aldehyde group in a fluid; and
  B) binding the functional group to a desired substance.

(41) A method according to item 40, wherein binding to the desired substance is achieved by ester bonding or amide bonding.

(42) A method for separating, concentrating, or purifying sugar chains or a sugar chain-containing substance in a sample, comprising the steps of:
  a) contacting a sugar chain-trapping carrier comprising a substance which can specifically interact with sugar chains with the sample in a fluid phase under conditions that the sugar chain-trapping carrier can react with the sugar chains or sugar chain-containing substance;
  b) isolating a composite of the sugar chain-trapping carrier and the sugar chains or sugar chain-containing substance from the fluid phase; and
  c) exposing the composite to conditions that the interaction between the sugar chain-trapping carrier and the sugar chains or sugar chain-containing substance is at least partially eliminated.

(43) A method according to item 42, wherein the sugar chain-trapping carrier further includes a support.

(44) A method according to item 42, wherein the steps a), b) and a) are performed in the same container.

(45) A method according to item 42, wherein the step b) includes performing centrifugal separation.

(46) A method according to item 42, further comprising the step of liberating an aldehyde group in the sample before step a).

(47) A method according to item 46, wherein the step of liberating the aldehyde group comprises proton-donating reaction by an enzyme treatment and/or a chemical method.

(48) A method according to item 46, wherein the step of liberating the aldehyde group comprises a treatment by glycosidase and/or a hydrazinolysis.

(49) A method according to item 42, further comprising the step of:
  d) subjecting the sample to conditions where the sugar chain-containing substance is separated into sugar chains and the remainder.

(50) An apparatus for separating, concentrating, or purifying sugar chains or a sugar chain-containing substance in a sample, comprising:
  a) a sample introduction section;
  b) a container having a space which can house a fluid phase; and
  c) a sugar chain-trapping carrier comprising a substance which can specifically interact with sugar chains,
  the container being in fluid communication with the sample introduction section.

(51) An apparatus according to item 48, wherein the substance which can specifically interact with sugar chains bound to the support, and the support is bound to a container.

(52) A system for separating, concentrating, or purifying sugar chains or a sugar chain-containing substance in a sample, comprising:
  A) an apparatus comprising:
    a) a sample introduction section;
    b) a container having a space which can house a fluid phase; and
    c) a sugar chain-trapping carrier comprising a substance which can specifically interact with sugar chains,
    the container being in fluid communication with the sample introduction section;
  B) means for isolating a composite of the sugar chain-trapping carrier and the sugar chains in the fluid phase; and
  C) means for exposing the composite to conditions that the interaction between the sugar chain-trapping carrier and the sugar chains is at least partially eliminated.

(53) A system according to item 52, wherein the sugar chain-trapping carrier further includes a support.

(54) A system according to item 52, wherein the means C) are means for liberating aldehyde.

(55) A system according to item 52, wherein the means C) are an enzyme or chemical substance for liberating aldehyde.

(56) A system according to item 52, further comprising:
  D) subjecting the sample to conditions that separate sugar chain-containing substance into sugar chains and the remainder.

(57) A method for manufacturing an apparatus for separating, concentrating, or purifying sugar chains or a sugar chain-containing substance in a sample comprising the steps of:
  a) providing a substance which can specifically interact with sugar chains;
  b) causing the substance which can specifically interact with sugar chains to interact with the support to produce a sugar chain-trapping carrier; and
  c) fixing the sugar chain-trapping carrier to a container.

(58) A method according to item 57, wherein the sugar chain-trapping carrier further includes a support.

(59) A method for analyzing sugar chains or a sugar chain-containing substance in a sample, comprising the steps of:

a) contacting a sugar chain-trapping carrier comprising a substance which can specifically interact with sugar chains with the sample in a fluid phase under the conditions that the sugar chain-trapping carrier can react with the sugar chains;

b) exposing the sugar chain-trapping carrier and the sample to conditions of desired stringency; and c) identifying a substance interacted with the sugar chain-trapping carrier.

(60) A method according to item 59, wherein the sugar chain-trapping carrier further includes a support.

(61) A method according to item 59, wherein the sample is derived from a subject which has or is expected to have a condition.

(62) A method according to item 59, wherein the steps a)-c) are performed on a chip supporting the sugar chain-trapping carrier.

(63) A method according to item 59, wherein the sugar chain-trapping carrier is arranged into an array on the chip.

(64) A method according to item 59, wherein the identifying step c) includes mass spectrometry analysis.

(65) A method for producing a sugar chain replica of a sample comprising or expected to comprise sugar chains, comprising the steps of:

a) locating a substance which can specifically interact with sugar chains on a surface of a two-dimensionally extended support, and contacting a surface on which the substance is not being located with a solid foil; and b) contacting the sample comprising or expected to comprise sugar chains with the solid foil.

(66) A method according to item 65, wherein the sugar chain-trapping carrier further includes a support.

(67) A method according to item 65, wherein the solid foil is transparent.

(68) A method according to item 65, comprising the step of marking a desired character of the sample on the solid foil.

(69) A method according to item 68, wherein the desired character is a lesion.

(70) A sugar chain replica of a sample comprising or expected to comprise sugar chains, comprising:

a) solid foil:

b) a two-dimensionally extended support on which a substance which can specifically interact with sugar chains is located, the support for interacting with the solid foil; and c) a component derived from the sample comprising or expected to comprise sugar chains, the component being trapped by the substance which can specifically interact with sugar chains.

(71) A sugar chain replica according to item 70, wherein the sugar chain-trapping carrier further includes a support.

(72) A sugar chain replica according to item 70, wherein the solid foil is marked with a mark related to the desired character of the sample.

(73) A method for analyzing sugar chains on a sample comprising or expected to comprise sugar chains, comprising the steps of:

a) locating a substance which can specifically interact with sugar chains on a surface of a two-dimensionally extended support, and contacting the surface on which the substance is not located with a solid foil;

b) contacting the sample comprising or expected to comprise sugar chains with the solid foil; and c) analyzing sugar chains existing on a surface of the solid foil.

(74) A method according to item 73, wherein the sugar chain-trapping carrier further includes a support.

(75) A method according to item 73, wherein the analyzing step includes ionizing a surface of the solid foil, and then performing mass spectrometry analysis.

(76) A method according to item 73, further comprising the steps of marking the desired character of the sample on the solid foil, and correlating the mark with the sugar chains identified by the mass spectrometry analysis.

(77) An apparatus for analyzing sugar chains or a sugar chain-containing substance in a sample, comprising:

a) sugar chain-trapping carrier comprising a substance which can specifically interact with sugar chains; and b) means for identifying the sugar chains.

(78) An apparatus according to item 77, wherein the sugar chain-trapping carrier further includes a support.

(79) A device for analyzing sugar chains or a sugar chain-containing substance in a sample, comprising a support on which a substance which can specifically interact with sugar chains is located.

(80) A device according to item 79, wherein the substance which can specifically interact with sugar chains is arranged on the support in an array.

(81) A device according to item 79, having a chip shape.

(82) A method for diagnosing or differentiating a subject, comprising the step of:

a) analyzing sugar chains or a sugar chain-containing substance in a sample derived from the subject using the device according to item 79.

(83) A method according to item 82, wherein the analyzing step comprises detecting presence of an antibody and/or lectin to the sugar chains or sugar chain-containing substance.

(84) A system for analyzing sugar chains or a sugar chain-containing substance in a sample, comprising:

a) sugar chain-trapping carrier comprising a substance which can specifically interact with sugar chains;

b) means for exposing the sugar chain-trapping carrier and the sample to the conditions of desired stringency; and c) means for identifying the sugar chains.

(85) A system according item 84, wherein the sugar chain-trapping carrier further includes a support.

(86) A system according item 84, wherein the means for identifying the sugar chains is a mass spectrometry analyzer.

(87) A method for manufacturing an apparatus for analyzing sugar chains or a sugar chain-containing substance in a sample, comprising the steps of:

a) providing a substance which can specifically interact with sugar chains; and b) causing the substance which can specifically interact with sugar chains to interact with the support to produce a sugar chain-trapping carrier.

(88) A method according to item 87, wherein the sugar chain-trapping carrier further includes a support.

(89) A method for producing a sugar chain array, comprising the steps of:

a) providing a support:

b) locating a substance which can specifically interact with sugar chains in a desired arrangement.

(90) A method for analyzing a substance specifically binding to sugar chains or a sugar chain-containing substance in a sample, comprising the steps of:

a) causing a sugar chain-trapping carrier comprising a substance which can specifically interact with sugar chains to interact with the sugar chains or sugar chain-containing substance in a fluid phase to fix;

b) contacting the sugar chain-trapping carrier with the sample under the conditions expected that the substance specifically binding to sugar chains or a sugar chain-containing substance can react with the sugar chains;

c) exposing a mixture of the sugar chain-trapping carrier and the sample to the conditions of desired stringency; and d) identifying the substance specifically binding to sugar chains or a sugar chain-containing substance.

(91) A method according to item 90, wherein the sugar chain-trapping carrier further includes a support.

(92) A method according to item 90, wherein the substance specifically binding to sugar chains or a sugar chain-containing substance is an antibody or lectin.

(93) A method according to item 90, wherein the sample is derived from a subject expected to have a lesion.

(94) A method according to item 90, further comprising the steps of:

e) correlating the antibody or lectin, and disease, disorder, disease damage or conditions related to its presence.

(95) A device for analyzing a substance specifically binding to sugar chains or a sugar chain-containing substance in a sample, comprising:

a) a sugar chain-trapping carrier comprising a substance which can specifically interact with sugar chains, in which the sugar chains or sugar chain-containing substance is fixed to the carrier by specific interaction.

(96) A device according to item 95, wherein the sugar chain-trapping carrier further includes a support.

(97) A system for analyzing a substance specifically binding to sugar chains or a sugar chain-containing substance in a sample, comprising:

a) a device comprising a sugar chain-trapping carrier comprising a substance which can specifically interact with sugar chains, in which the sugar chains or sugar chain-containing substance is fixed to the carrier by specific interaction;

b) a sample introduction section:

c) means for exposing a mixture of the sugar chain-trapping carrier and the sample to the conditions of desired stringency; and d) means for identifying the substance specifically binding to sugar chains or a sugar chain-containing substance.

(98) A system according to item 97, wherein the sugar chain-trapping carrier further includes a support.

(99) A sugar chain composition having an increased sugar chain content, obtained by contacting a sample comprising sugar chains with a substance which can specifically interact with sugar chains, and then separating sugar chains in the interacted sample.

(100) A sugar chain composition according to item 99, wherein the substance which can specifically interact with sugar chains can specifically interact with any sugar chain at a certain level or higher.

(101) A medicine comprising a sugar chain composition according to item 99.

(102) A food comprising a sugar chain composition according to item 99.

(103) A cosmetic comprising a sugar chain composition according to item 99.

(104) A polymeric material comprising a sugar chain composition according to item 99.

(105) An agricultural chemical comprising a sugar chain composition according to item 99.

(106) An assay kit comprising a sugar chain composition according to item 99.

BRIEF DESCRIPTION OF THE DRAWINGS

FIG. 7 is a diagram showing a proportion of sugar chain structures calculated from HPLC peak intensities of FIG. 6.

BEST MODE FOR CARRYING OUT THE INVENTION

Figure 1:
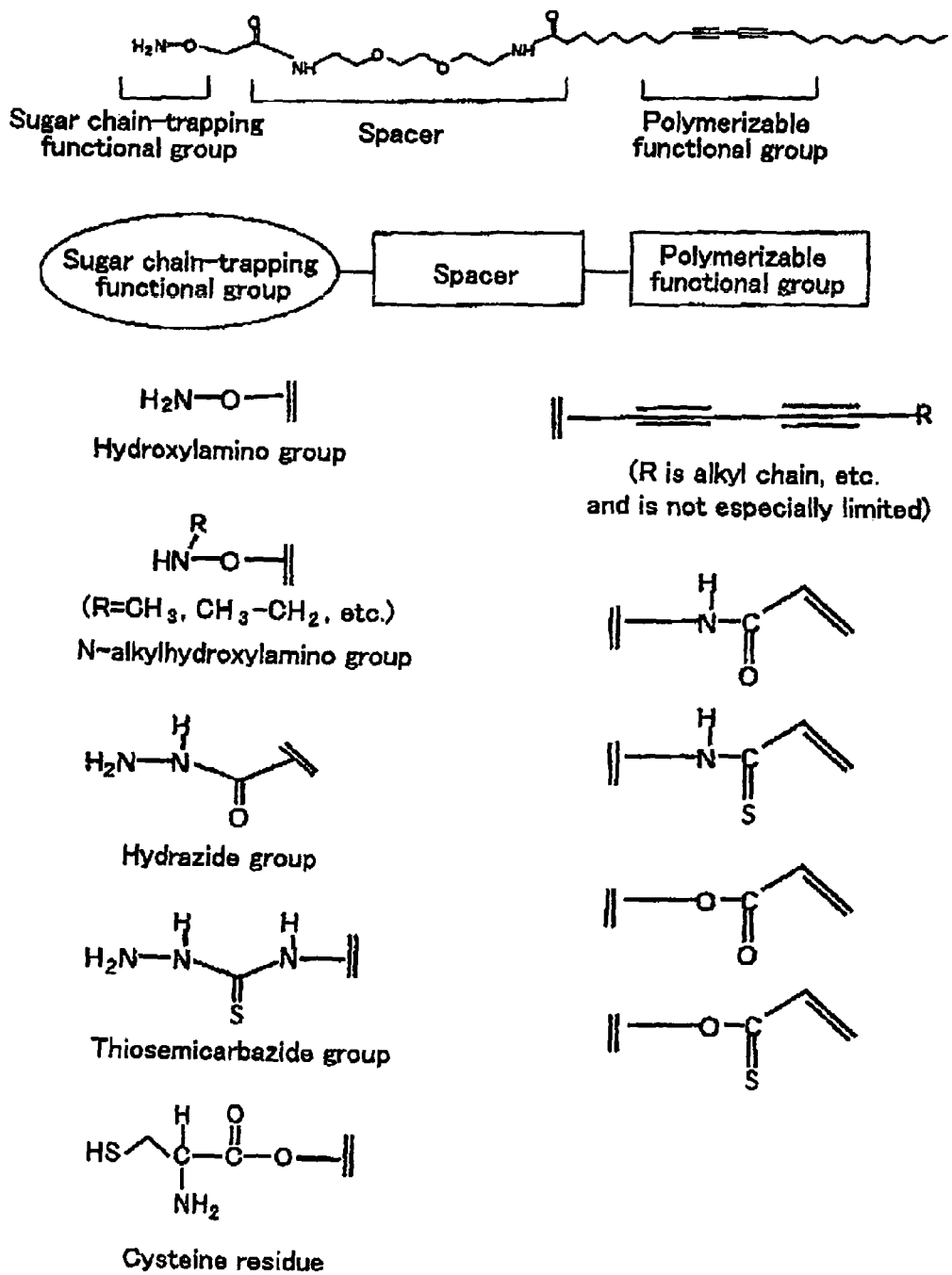
FIG. 1 is a schematic diagram of the substance which can specifically interact with sugar chains of the present invention.

Hereinafter, the present invention will be described. It should be understood that, throughout the specification, expressions in singular forms also include concepts of plural forms unless otherwise noted. Furthermore, it should be understood that the terms as used herein have the meanings which are generally referred to in the field unless otherwise noted.

(Terms)

Hereinafter, definitions of the terms used herein will be listed.

As used herein, "sugar chain" refers to a compound formed by one or more unit sugar (monosaccharide and/or derivatives thereof) in series. When there are two or more unit sugars in series, each of the unit sugars are bound by dehydrocondensation by a glycosidic bond. Such sugar chains include a wide variety of sugar chains, for example, polysaccharide (glucose, galactose, mannose, fucose, xylose, N-acetylglucosamine, N-acetylgalactosamine, sialic acid and, composites and derivatives thereof) included in living bodies, decomposed polysaccharides, sugar chains decomposed or derived from composite living body molecules such as glycoproteins, proteoglycan, glycosaminoglycan, and glycolipid, and the like, but not limited to these. Thus, as used herein, the term sugar chain is used interchangeably with "polysaccharide", "glucid", and "carbohydrate". Furthermore, unless specifically referred to, "sugar chains" as used herein may include both sugar chains and a sugar chain-containing substance.

As used herein, "monosaccharide" refers to a compound which cannot be hydrolyzed into more simple molecules, and represented by the formula $C_nH_{2n}O_n$. The compounds in which, n=2, 3, 4, 5, 6, 7, 8, 9 and 10, are respectively referred to as diose, triose, tetrose, pentose, hexose, heptose, octose, nonose and decose. In general, the compounds correspond to aldehyde or ketone of linear polyvalent alcohol. The former is called aldose, and the latter is called ketose.

As used herein, "derivative of monosaccharide" refers to a substance produced as a result of substitution of one or more hydroxyl group on a monosaccharide by another substituent, which does not falls upon the range of monosaccharide. Such derivatives of monosaccharides include sugar having a carboxyl group (for example, aldonic acid which has C-1 site oxidized and became carboxylic acid (for example, D-gluconic acid having D-glucose oxidized), uronic acid having C atom at terminal became carboxylic acid (D-glucuronic acid having D-glucose oxidized), sugar having an amino group or a derivative of an amino group (for example, acetylated amino group) (for example, N-acetyl-D-glucosamine, N-acetyl-D-galactosamine and the like), sugar having both an amino group and a carboxyl group (for example, N-acetyl neuraminic acid (sialic acid), N-acetyl muramic acid and the like), deoxylated sugar (for example, 2-deoxy-D-ribose), sulfated sugar including a sulfuric acid group, phosphorylate sugar including a phosphate group, and the like, but not limited to these. Glycoside having an acetal structure formed by reacting with alcohol in sugar forming a hemiacetal structure is also within the range of the deliverive of monosaccharide.

As used herein, "sugar chain-containing substance" refers to a substance including a sugar chain and a substance other than sugar chains. Such a sugar chain-containing substance is found in living bodies in a large quantity, and includes, for example, a wide variety of polysaccharides included in living bodies, decomposed polysaccharides, sugar chains decomposed or derived from composite living body molecules such as glycoprotein, proteoglycan, glycosaminoglycan, glycolipid, and the like, but not limited to these.

As used herein, "glycoprotein" includes, for example, enzymes, hormone, cytokine, antibody, vaccine, receptor, serum proteins and the like, but not limited to these.

As used herein, "substance which does not include sugar chains" refers to a substance which does not include a sugar chain at all or does not include in an amount which can be detected. Such substances which do not include sugar chains include, for example, organic compounds other than sugar chains, such as, simple protein, simple lipids and the like, but not limited to these.

As used herein, "specificity" or to be "specific" to sugar chains or a sugar chain-containing substance refers to a property of a certain substance. It means that the substance can interact with the sugar chains or the sugar chain-containing substance, but interact less actively with substances other than the sugar chains and the sugar chain-containing substance.

As used herein, "specifically interact with sugar chains" refers to the capability to interact with the sugar chains with a higher specificity compared to that of a substance which does not include sugar chains. Preferably, such a substance which does not include sugar chains may include substances inside living bodies. Such a capability can be confirmed by determining that the specific interaction with at least a constant amount of sugar chains remains, when exposed to the conditions such that non-specific interaction with a substance other than the sugar chains is dissociated. More specifically, such capability can be confirmed when necessary dissociation energy for a bound composite of sugar chains and a subject substance, irradiated with laser in a MALDI-TOF, is at least about 5 eV, preferably, at least about 10 eV, and more preferably, at least about 15 eV, and the interaction is destroyed in a significant amount and in large percentages when a composite of a substance which does not include sugar chains and the subject substance is irradiated under similar conditions.

As used herein, when "interaction" is used for describing two objects, it means two objects exert forces on each other. Such interaction includes, for example, covalent bond, hydrogen bond, van der Waals force, ionic interaction, nonionic interaction, hydrophobic interaction, electrostatic interaction, and the like, but not limited to these. Preferably, the interaction is a covalent bond. As used herein, "covalent bond" is used to have a normal meaning in the field of the art, refers to chemical bonds formed when a pair of electrons are shared by two atoms. Such covalent bond includes, but not limited to, for example, oxime bonding, hydrazone bonding, thiosemihydrazone bonding, perhydrothiazine ring formation, thiazolidine ring formation, and the like.

As used herein, "level" of interaction and the like refers to an extent of strength of the interaction and the like, and is also called "strength". It may be used for determining the specificity toward sugar chains. As such a level of interaction, for example, is the necessary dissociation energy when laser irradiation is performed in MALDI-TOF.

As used herein, "predetermined level" refers to an extent of specific interaction with sugar chains set in accordance with a certain objective, and may be any level which is useful for determining the specificity to the sugar chains. Such predetermined level varies depending upon the measurement conditions, but, for example, may be a level where necessary dissociation energy when laser irradiation is performed in MALDI-TOF, is at least about 5 eV, preferably about 10 eV, and more preferably about 15 eV. However, the level is not limited to such level. Preferably, such predetermined level may have both a lower limit and an upper limit. Therefore, for example, it may be preferable that the necessary dissociation energy when laser irradiation is performed in MALDI-TOF is within the range of about 5-500 eV, about 10-100 eV, about 15-50 eV, or the like. Alternatively, if expressed in relative ways, difference in the highest and lowest level may be preferably within a range of 100 times, 50 times, 20 times, 10 times, 5 times, 4 times, 3 times, 2 times, or 1.5 times.

As used herein, "range" of the level of interaction from the highest to the lowest refers to the range from the maximum value to the minimum value of the interaction level measured by using the above-mentioned methods. The maximum value can be represented in multiples of the minimum value. The smaller the value, the more uniform the specificity is.

As used herein, "MALDI-TOF(MS)" refers to the abbreviation of Matrix Assisted Laser Desorption Ionization-Time-of-Flight (Mass Spectrometer). MALDI is a method discovered by Tanaka et al., and developed by Hillenkamp et al. (Karas M., Hillenkamp, F., Anal. Chem., 1988, 60, 2299-2301). In this method, after a sample and a matrix solution are mixed to a molar ratio of $(10^{-2}-5\times10^{-4}):1$, the mixed solution is dried on a target to be in a crystal condition. Large energy is given to the matrix by pulse laser irradiation, and thus ions derived from the sample such as $(M+H)^+$, $(M+Na)^+$ and the like, and ions derived from the matrix are dissociated from each other. Analysis is possible even when there is a contamination by a small amount of phosphoric acid buffer, Tris buffer, guanidine, and the like. MALDI-TOF (MS) measures a mass based on time of flight using MALDI. When an ion is accelerated at a certain accelerating voltage V, where mass of the ion is m, speed of the ion is v, charge number of the ion is z, elementary electric charge is e, and time of flight of the ion is t, m/z of the ion can be expressed by the formula $m/z=2eVt^2/L^2$. For such MALDI-TOF measurement, KOMPACT MALDI II/III of Shimazu/Kratos or the like can be used. When such measurement is performed, reference can be made to pamphlets offered by the manufactures. Irradiation energy of laser irradiation used for measurement by the MALDI-TOF is referred to as "dissociation energy" herein.

As used herein, "sugar chains which are not oxidized" refer to sugar chains which do not include oxidized monosaccharide or derivatives of oxidized monosaccharide. Regarding the derivative of monosaccharide, a derivative of monosaccharide which is not oxidized is, preferably, a derivative of monosaccharide in which a portion derived from the monosaccharide is not oxidized.

As used herein, "oxidized sugar chains" refer to sugar chains including oxidized monosaccharide and a derivative of oxidized monosaccharide. The oxidized monosaccharide is as described above, and may be, for example, D-gluconic acid or the like, but not limited to this. Regarding the derivative of monosaccharide, a derivative of oxidized sugar chains is, preferably, sugar chains in which a portion derived from the monosaccharide is oxidized.

As used herein, "bindable to a support" means a capability of a substance to be bound to a support when it refers to a property of a substance, As used herein, "support" and "substrate" can be used interchangeably, unless otherwise noted, it refers to a material (preferably a solid) which can support another substance in the presence of a fluid (particularly, solvent such as liquid) when it is used for supporting the substance. A material used for support includes any solid material which has a property, or derivatized to have a property to bind to the substance of the present invention by either a covalent bond or a non-covalent bond, but not limited to this. Preferably, the support is solid at room temperature (from 0° C. to 30° C.). More preferably, the support maintains a solid state in a circumstance where purification, concentration, separation or analysts. Such a circumstance may be at temperature below 0° C., or 30° C. or higher. High temperature may be preferably less than 100° C. When it is assumed that the support interacts with the substance of the present invention, it may be advantageous that the interaction of the support with the substance of the present invention is maintained under the presence of a strong acid at least partially, preferably, half or more of the interaction is maintained, more preferably, most of the interaction is maintained.

As used herein, "substrate" may refer to a support which has an appropriate shape such as a chip when it is used for a sugar chain chip.

A material used as the support, can be any material which can form a solid surface, for example, glass, silica, silicon, ceramic, silicon dioxide, plastic, metal (including alloy), natural and synthetic polymer (for example, polystyrene, cellulose, chitosan, dextran, and nylon), lipid, and the like, but not limited to these materials. Preferably, the support has a hydrophobic surface. The support may be formed by layers of a plurality of different types of materials. For example, a plurality of inorganic insulating materials such as glass, quartz glass, alumina, sapphire, forsterite, silicon carbide, silicon oxide, silicon nitride and the like may be used, but not limited to these materials. Other materials for the support, like organic materials such as polyethylene, ethylene, polypropylene, polyisobutylene, polyethylene terephthalate, unsaturated polyester, fluorine-containing resin, polyvinyl chloride, polyvinylidene chloride, polyvinyl acetate, polyvinyl alcohol, polyvinyl acetal, acryl resin, polyacrylonitrile, polystyrene, acetal resin, polycarbonate, polyamide, phenol resin, urea resin, epoxy resin, melamine resin, styrene-acrylonitrile copolymer, acrylonitrile butadiene-stylene copolymer, silicone resin, polyphenylene oxide, polysulfone and the like, may also be used. In the present invention, films used for blotting, such as, a nylon film, a nitrocellulose film, a PVDF film, and the like may also be used. When a nylon film is used, the result can be analyzed using a convenient analysis system. For analyzing a substance with high density, it is preferable to use materials having a certain hardness, such as glass. In one embodiment, for example, cross-linked liposome, cross-linked polymer or non-cross linked polymer can be used as the support, but not limited to this. The support may be magnetic. If the support is magnetic, it becomes easy to perform purification using magnetic property. In a preferred embodiment, the support used in the present invention may be cross-linked liposome, cross-linked polymer or non-cross-linked polymer, and may be particles which can be dispersed in water or organic solvent having an average particle size of 0.001 micron or higher and less than hundreds of microns.

The substance of the present invention may be bound to another substance as described above which is used as the support, or the substance of the present invention itself may serve as the support.

As used herein, "functional group which can react with an aldehyde group in a fluid" refers to a functional group having the property to react with an aldehyde group and form a specific and stable bond in an equilibrium between the cyclic hemiacetal type and the non-cyclic aldehyde type, which are formed by sugar chains in fluids such as an aqueous solution. Such a functional group may be hydroxylamino group, N-alkylhydroxylamino group, hydrazide group, thiosemicarbazide group and cysteine residue, but not limited to these. Preferably, such functional group is a hydroxylamino group. Linkage pattern between a hydroxylamino group and saccharide (oxime bonding) is particularly weak towards acid. Thus, there is an advantage that a step of cleaving out sugar chains from a sugar chain-trapping carrier can be readily performed.

As used herein, "fluid" can be any kind of fluid as long as it provides a circumstance where the substance of the present invention can interact with the sugar chains. Preferably, such a fluid includes substantially no substance including a keto group. Because, if fluid includes a substance having a keto group in a significant amount, the aldehyde group in the fluid and the substance of the present invention do not react well. Thus, an embodiment which does not include a substance including a keto group is not essential, but preferable.

Therefore, a fluid as used herein is preferably a fluid which brings the saccharide into an equilibrium between the cyclic hemiacetal type and the non-cyclic aldehyde type. Such fluid may be, for example, an aqueous solution, an organic solvent and a mixture thereof, but not limited to these. Preferably, the fluid is an aqueous solution.

As used herein, "cross-linked polymer" refers to a polymer having cross-linking bonds. Cross-linking bond may be generated by methods using, for example, cross-linking agent, ultraviolet rays, electron beam, or radiation ray. Such cross-linked polymer may be, for example, phenol resin, urea resin, melamine resin, epoxy resin, polyurethane, vinylester resin, cross-linked polystyrene, cross-linked rubber, acrylamide polymer and the like, but not limited to these.

As used herein, "lipid film" refers to lipid in a film form. As used herein, "lipid" refers to a group of substances forming living bodies which are not very soluble in water and readily soluble in organic solvents. The lipids include a variety of organic compounds. Typically, the lipids include long chain fatty acids and derivatives or analogs thereof. However, in the present specification, organic compound groups in living bodies which are water-insoluble and readily soluble in organic solvents, such as, steroid, carotenoid, terpenoid, isoprenoid, fat-soluble vitamins, and the like are also included. Lipids are, for example, 1) simple lipid (which is ester of fatty acid and an alcohol and may also be referred to as neutral lipid; for example, fat and oil (triacylglycerol), wax (fatty acid ester of higher alcohol), sterolester, fatty acid esters of vitamins, and the like); 2) complex lipid (compounds which have ester bond or amide bond and have a polar group such as phosphoric acid, saccharide, sulfuric acid, amine and the like besides fatty acid and alcohol, including glycerophospholipid, sphingophospholipid, glyceroglycolipid, sphingoglycolipid, lipid having C—P bond, sulfolipid, and the like): 3) derived lipid (compounds produced by hydrolysis of simple lipid and complex lipid which are fat-soluble, including fatty acid, higher alcohol, fat-soluble vitamins, steroid, hydrocarbon, and the like), but not limited to these. In the present invention, any lipid can serve as a support by itself as long as the lipid does not inhibit the specific interaction with sugar chains.

As used herein, "photopolymerizable lipid derivative" refers to lipids or derivatives thereof having a property to initiate polymerization reaction when exposed to light (for example, visible light rays, ultraviolet rays, and the like). Such lipids may be, for example, compounds having a diacetylene structure represented by formula (III): —C≡C—C≡C—, photopolymerizable monomers other than diacetylene such as acrylate, epoxide, vinyl ether and the like, but not limited to these. Such photopolymerizable lipid derivatives may be polymerized preferably by ultraviolet rays.

As used herein, "two-dimensionally extend" refers to, in terms of the substance which can specifically interact with sugar chains of the present invention, to be in a form of film or to bring into a form of film. The form of a shape obtained by two-dimensionally extending as such, may be, for example, cast film, monolayer, water dispersion (synonymous to liposome in the present specification), but not limited to these. As used herein, "cast film" is a film produced by using the cast method, and such cast film can be produced by casting and drying a solution including the substance which can specifically interact with sugar chains of the present invention. As used herein, "monolayer" refers to a film of unimolecular layer in the order of nm, which is formed on a gas-liquid interface or a solid-liquid interface. In the present invention, for producing "sugar chain-trapping carrier" or "sugar chain replica" which will be shown below, a method in which a monolayer including the substance which can specifically interact with sugar chains of the present invention is transferred to a support is used. In the present invention, it is preferable to employ a Langmuir-Blodgett film (commonly known as a LB film) obtained by forming a monolayer of a substance which can specifically interact with the sugar chains of the present invention formed on the surface of water, among the "monolayer" in a broader sense as described above, on a surface of water, and transferring to and depositing on a solid substrate by an arbitrary method. The most universal way to form an LB film is a technique of moving a solid support (or a solid substrate) vertically by traversing a monolayer on the surface of water at a constant surface pressure, but not limited to this. Other techniques include a horizontal attachment method in which only one layer of the monolayer is transferred to a solid support. This method is also useful in the present invention. In the present invention, "deposit" means that a monolayer is transferred to a solid support. The monolayer may be transferred to the solid support once, or may be transferred a plurality of times. In order to deposit the monolayer onto the solid support with a film condition or a film order on a surface of water being maintained, those skilled in the art may try all kinds of things. However, it is necessary to two-dimensionally extend the substance which can specifically interact with sugar chains of the present invention on the surface of the water, and form a monolayer. Thus, it is preferable that the substance which can specifically interact with sugar chains of the present invention, which forms the film, to be amphiphilic. In such cases, a sugar chain-trapping functional group, which is a component of the substance which can specifically interact with sugar chains of the present invention, is hydrophilic, and a portion other than the sugar chain-trapping functional group is hydrophobic. The above-described method is very useful in building "sugar chain-trapping carrier" or "sugar chain replica" which will be shown below.

As used herein, "matrix molecule" means a molecule which does not have a sugar chain trapping capability, but which is introduced to further stabilize a film formed of the substance which can specifically interact with sugar chains of the present invention. Further, by introducing such a matrix molecule, a space in the lateral direction can be provided between sugar chain-trapping functional groups on a film plane. Furthermore, by changing the molar fraction of the matrix molecule in all molecules forming the film, films having various two-dimensional distributions of the sugar chain-trapping functional groups can be produced without any restriction. As the "matrix molecule" of the present invention, compounds represented by formula (II) are shown.

As used herein, "sugar chain-trapping carrier" includes a carrier for trapping sugar chains. Such carrier includes a portion for trapping sugar chains and a portion which is used as a carrier. For the portion to trap sugar chains, substances which specifically interact with the sugar chains of the present invention may be used. For the carrier, a support may be used. Alternatively, the substance which specifically interacts with sugar chains of the present invention itself may function as a carrier. Such carrier may be a carrier having "X" in formula (I) mentioned above. More specifically, a carrier in which "X", "X—Y", and "X—Y—Z" are bound to a support, and a carrier in which compounds represented by formulae (I) and (II) are polymerized.

As used herein, "insoluble in organic solvents" refers to a property of a substance that does not dissolved or not substantially dissolved in solvents including an organic compound. Such organic solvents may be, for example, alcohol (methanol, ethanol and the like), acetone, alkane (for example, hexane), and the like, but not limited to this. Being insoluble means that, when the substance (solute) is put into an organic solvent, the amount of solvent required for dissolving 1 g or 1 ml of the solute is 1 L, preferably, 10 L or more.

As used herein, "self-closed" film refers to a film, which is closed in a circular shape such as liposome, a single layer, or a plurality of layers. Therefore, such self-closed film (for example, lipid film) may be, for example, a liposome, but not limited to this.

As used herein, to "separate" sugar chains or a sugar chain-containing substance in a sample, refers to substantially removing or purifying the sugar chains or sugar chain-containing substance from the state in which they exist in the sample before separation. Thus, in the sugar chains or the sugar chain-containing substance separated from the sample, at least the contents of substances other than the sugar chains or sugar chain-containing substance, which have been included before the separation, are decreased.

As used herein, "isolation" of a substance (biological agents, for example, sugar chains, nucleic acids, proteins and the like) refers to substantially separating or purifying from other substances in a cell of a living body in which the biological agent naturally exist (for example: when the agent is a sugar chain or a sugar chain-containing substance, agents other than the sugar chains or sugar chain-containing substance, or sugar chains or sugar chain-containing substances other than the target sugar chains or sugar chain-containing substance; when the agent is nucleic acid, agents other than nucleic acid, and nucleic acids including nucleic acid sequences other than the target nucleic acid; when the agent is a protein, agents other than protein and proteins including amino acid sequences other than the target protein). The "isolated" sugar chains or sugar chain-containing substance include sugar chains or sugar chain-containing substance purified by a purification method of the present invention. Thus, the isolated sugar chains or sugar chain-containing substance include chemically synthesized sugar chains or sugar chain-containing substance.

As used herein, "purification" of a substance (biological agents, for example, sugar chains, nucleic acids, proteins, and the like) refers to removing at least a part of agents which are associated to the substance in nature. Thus, purification and separation partially overlap in their forms. Typically, the purity of the purified substance (for example, biological agents such as sugar chains or sugar chain-containing substance), is higher than that of the substance in its usual existing state (i.e., is concentrated), but, as long as the agents associated in nature are reduced, the state in which the substance is not concentrated is within the concept of "purification".

As used herein, "concentration" of a substance (for example, biological agents such as sugar chains or sugar chain-containing substance) refers to an action to raise the concentration of the substance to be higher than the content of the substance included in the sample before concentration. Thus, the concept of concentration also overlaps those of purification and separation. Typically, concentrated substance (for example, biological agents such as sugar chains or sugar chain-containing substance) has reduced contents of impurities compared to those with the substance in its usual existing state. However, as long as the content of the target substance increases, certain impurities may be increased, and not "purified" state is also included within the concept of "concentration".

As used herein, "conditions that a sugar chain-trapping carrier can react with sugar chains or a sugar chain-containing substance" refers to conditions sufficient for the sugar chain-trapping carrier to react (preferably, to form covalent bond) with the sugar chains or sugar chain-containing substance (for example, buffers, polarities of solvents, temperature, pH, salt concentration, pressures, and the like). Setting parameters which are necessary for such conditions is within the range of the skills of those skilled in the art. By considering a variety of parameters which are related to the interaction, such as, type of the interaction, types of the sugar chains or sugar chain-containing substance, type of the sugar chain-trapping carrier (for example, functional group which can react with an aldehyde group in a fluid), those skilled in the art can set the conditions using well-known techniques in the art to perform the interaction reaction. In a preferable embodiment, such conditions may be conditions in which, sugar chains react with aldehyde groups to form specific and stable bond in an equilibrium between the cyclic hemiacetal type and the non-cyclic aldehyde type which are formed by sugar chains in fluids such as an aqueous solution, but not limited to these. Alternatively, it may be a preferable condition that a fluid supplied for reaction includes substantially no keto group. Such a condition may be, for example, to use an acetic acid buffer of pH 5.6 at room temperature and atmospheric pressure (for example, 20° C. and 1 atmosphere).

As used herein, "composite of a sugar chain-trapping carrier and sugar chains or sugar chain-containing substance" refers to the sugar chain-trapping carrier and the sugar chains or sugar chain-containing substance of the present invention interacting with each other to become a composite. Preferably, in such composite, the sugar chain-trapping carrier and the sugar chains or sugar chain-containing substance are covalent-bound to each other. Thus, in the present specification, a substance having two or more portions bound to each other by a covalent bond is also included within the concept of the composite.

As used herein, "conditions that interaction between the sugar chain-trapping carrier and the sugar chains or sugar chain-containing substance is at least partially eliminated" refers to conditions that interaction formed between the sugar chain-trapping carrier and the sugar chains or sugar chain-containing substance of the present invention (for example, covalent bond) is at least partially reduced. Thus, when the above interaction is a covalent bond, "conditions that interaction between the sugar chain-trapping carrier and the sugar chains or sugar chain-containing substance is at least partially eliminated" refer to conditions that covalent bonds formed between the sugar chain-trapping carrier and the sugar chains or sugar chain-containing substance are released at least partially, and preferably, all. Such conditions may be, for example, using physical means (for example, laser and the like), chemical means (acidic condition), or biochemical means (for example, enzymes), but not limited to this. The conditions may be any condition as long as the desired sugar chains and sugar chain-containing substance are separated in a recognizable form. The desired sugar chains or sugar chain-containing substance may be degenerated, but it may be advantageous that, the desired sugar chains or sugar chain-containing substance be separated without being degenerated preferably, and more preferably, separated in a naturally existing state. Such conditions may be, specifically, for example, exposure to an acidic condition, and it may be convenient and advantageous to mix it with a proton type ion exchange resin, and strong cation exchange resin and then separate, preferably. Physically disconnecting bound substance which is separated according to the present invention is not limited in terms of a method for separating sugar chains.

However, it mainly refers to disconnecting a polymer and the sugar chains by appropriately adjusting laser irradiation energy intensity.

As used herein, "conditions that the sugar chain-containing substance is separated into sugar chains and the rest" refers to conditions that the bond formed between the sugar chains and the rest of the substance (for example, peptides, lipids, and the like) in the sugar chain-containing substance (for example, covalent bond) is removed. Such conditions may be provided using physical means (for example, laser and the like), chemical means (acidic condition) or biochemical means (for example, enzymes such as glycosidase), but not limited to this. The conditions may be any condition as long as the desired sugar chains in the sugar chain-containing substance are separated in a recognizable form. The desired sugar chains may be degenerated, but it may be advantageous that, the desired sugar chains or sugar chain-containing substance be separated without being degenerated, and more preferably, separated in a naturally existing state. Such conditions may be, specifically, for example, exposure to an acidic condition, and it may be convenient and advantageous to mix it with a proton type ion exchange resin, and strong cation exchange resin and then separate, preferably. Physically disconnecting bound substance which is separated according to the present invention is not limited in terms of a method for separating sugar chains. However, it mainly refers to disconnecting a polymer and the sugar chains by appropriately adjusting laser irradiation energy intensity. Thus, the "conditions that the sugar chain-containing substance is separated into sugar chains and the rest" may overlap with the "conditions that interaction between the sugar chain-trapping carrier and the sugar chains or sugar chain-containing substance is at least partially eliminated". Furthermore, the "conditions that the sugar chain-containing substance is separated into sugar chains and the rest" may also overlap with conditions for liberating an aldehyde group.

As used herein, "container" refers to any type of container as long as it has a shape to contain fluids. A material of the container may also be any material as long as it can contain fluids, can withstand reactions occur in the present invention, or can be processed as such. Such material is preferably a solid at normal temperature (temperature between 0° C. to 30° C.). More preferably, it can maintain a solid state under circumstances where purification, concentration, separation or analysis take place. Such circumstances may be at a temperature below 0° C., or a temperature of 30° C. or higher. High temperature may be, for example, 100° C. or below, preferably. Such material may be any material which can form a solid surface. However, the material may be, for example, glass, silica, silicon, ceramic, silicon dioxide, plastic, metal (including alloy), natural and synthesized polymer (for example, polystyrene, cellulose, chitosan, dextran, and nylon), paper, and the like, but not limited to these. Such material may be coated, or may not be coated.

As used herein, "coating" refers to a surface treatment performed for giving a certain property to the container or a substance used for the surface treatment. Such coating may be used for giving, for example, water resistance, oil resistance, resistance to organic solvent, acid resistance, and the like. Such coating material may be, for example, a fluorine resin, a silane water-base paint resin, and the like, but not limited to these.

As used herein, "centrifugal separation" can be performed by any technique as long as separation by applying acceleration can be performed. Such centrifugal separation includes centrifugal filtration technique in which filters such as Microcon (available from Millipore) are combined. When the methods of the present invention are performed in one container, the container may be the container used for the centrifugal filtration technique.

As used herein, "liberating an aldehyde group in the sample" refers to exposing aldehyde in sugar chains or sugar chain-containing substance included or expected to be included in the sample, Further, the generation of a galactose residue by galactose oxidase, and the generation of an aldehyde group by periodate acidolysis of 6-aldehyde and diol group are also included. By liberating the aldehyde group in the sample, it becomes easy to proceed to the interaction between the substance which specifically interacts with sugar chains of the present invention and the sugar chains or sugar chain-containing substance thereafter. Alternatively, by exposing the sample to conditions for liberating an aldehyde group in the sample, only the sugar chains in the sugar chain-containing substance can be separated, and concentrated, purified or analyzed. When such a state is desired, it may be advantageous.

The conditions for liberating an aldehyde group in the sample may be, for example, proton-donating reaction by an enzyme treatment and/or chemical method, but not limited to these. Such enzyme treatment may be, for example, a treatment by sugar chain liberation enzymes such as N-glycosidase (for example, enzyme derived from *Flavobacterium meningosepticum* expressed in *E. coli*), glycopeptidase A (almond), and the like, but not limited to this. Such enzymes used in the present invention include glucosidase derived from plants, yeasts, or molds, and preferably, N-glucosidase derived from *Flavobacterium*, but not limited to these. The chemical method may be, for example, a hydrazinolysis (liquid phase or gas phase), but not limited to this. In hydrazinolysis, for example, a sample (for example, a glycoprotein-including sample of 200 to 1000 μg) is lyophilized (using a screw cap vial or a screw cap test tube), and anhydrous hydrazine (for example, 100 to 200 μl) is added to heat at 100° C. for few hours to ten and few hours (for example, dry block heater or oven is used). Thereafter, a few drops of toluene are added, a sample vial is put into a desiccator. Decompression is performed by a vacuum pump having a cold trap for azeotropic distillation of hydrazine. Such azeotropic distillation is repeated for several times and completely distilling hydrazine, to finish, a hydrazinolysis and desired sugar chains are separated.

As used herein, to "introduce a sample" used in an apparatus of the present invention refers to moving the sample to a place where reactions of the present invention should occur. A sample introduction section may have any shape as long as it is suitable for introducing a sample. Further, as a method for introducing a sample may be, for example, a method using an injector, on column method, a method for injecting a sample and flowing into a column by a mobile phase, and a method using a sample valve, and the like, but not limited to these. Means for introducing a sample may be a sample injector, autosampler, microfeeder, and the like, but not limited to these. For examples concerning using chromatography, see "Kosoku ekitai kuromatogurafi (High Performance Liquid Chromatography)", edited by Hiroyuki Hatano, Kagaku no Ryoiki, Extra Edition, No. 102, Nankodo Co., Ltd.; "Kosoku ekitai kuromatogurafi no sochi and fuzoku sochi (Apparatus and auxiliary equipment for high performance liquid chromatography)", Norio Okuyama, Kazuo Seta, pp. 11-40.

As used herein, "can house a fluid phase" means to have volume of a fluid phase used in reactions of the present invention sufficient for the reactions of the present invention to occur. Preferably, a container having a space which can house a fluid phase has the ability to keep a fluid phase with substantially no loss and no degeneration.

As used herein, to be in "fluid communication" is also referred to as "fluid connection", and means that fluid housed in two containers is movable between the two containers at least in one direction, preferably in both directions. Thus, when the container and the sample introduction section are in fluid communication, if a sample is introduced in the sample introduction section, at least part of the sample can be introduced into the container. The state of being in fluid communication may continue all the time, or may be temporary. To be in fluid communication temporarily, it may preferable to provide a controller for controlling such conditions in the apparatus, but it may also be controlled manually.

As used herein, "bond" between the support and the container may be in any form as long as the support is being fixed during the reactions used in the present invention. Preferably, the bond may be a covalent bond, but other interactions such as hydrophobic interaction may be used alone or together.

As used herein, "means for isolating a composite of the sugar chain-trapping carrier and the sugar chains" may be any kind of means as long as it can isolate the composite of the sugar chain-trapping carrier and the sugar chains. Such means may be a centrifugal separation equipment, filter, chromatography apparatus and the like, but not limited to these. When the carrier is magnetic, a separation method utilizing magnetic property may be used. In such cases, means for isolating the composite of the sugar chain-trapping carrier and the sugar chains or sugar chain-containing substance may be a magnet. Alternatively, the composite of a sugar chain-trapping carrier and sugar chains or sugar chain-containing substance may be isolated by exposing the carrier to the conditions of stringency at which the interaction between the carrier and the sugar chains is not separated.

As used herein, "desired stringency (conditions)" refers to conditions where the interaction between the substance which specifically interact with sugar chains and the sugar chains or sugar chain-containing substance does not dissociate. Such conditions can be appropriately selected by those skilled in the art using well-known techniques in the field of art in consideration of various parameters such as, a reagent to be used, carrier, sugar chains or sugar chain-containing substance, substance which specifically interact with the sugar chains, interaction to be formed. For example, when the interaction is a covalent bond, desired stringency may be to rinse in water (for example, ultrapure water) or buffer (for example, acetic acid buffer).

As used herein, "identification of a substance which interacted with a sugar chain-trapping carrier" refers to revealing identity of the interacted substance. Typically, it refers to determining whether the substance is sugar chains or not, and to determine what type of sugar chains they are. For such identification, various measurement methods can be used, for example, physical analysis such as mass spectrum analysis, NMR, X-ray analysis, elemental analysis and the like, chemical analysis by observing chemical specific reactions and the like, biochemical analysis by determining substrate specificity of enzymes and the like, or, biological analysis by determining reactions of living organisms (for example, microorganisms such as bacteria) may be used, but not limited to these.

As used herein, "etiology" refers to agents related to disease, disorder, or condition of a subject (in the present specification, which may also be collectively referred to as "lesion", and may also be referred to as disease damage in the case of plants), and includes, for example, pathogenesis substance (pathogenesis agent), pathogen, lesion cell, pathogenesis virus and the like, which may be the cause, but not limited to these.

Such a disease, disorder or condition may be, for example, a circulatory system disease (anaemia (for example, aplastic anemia (particularly, severe aplastic anemia), renal anaemia, cancerous anaemia, secondary anaemia, refractory anaemia, or the like), cancer or tumor (for example, leukemia, multiple myeloma) and the like); nervous system disease (dementia, cerebral embolism and sequela aftereffects thereof, cerebral tumor, spinal cord injury and the like); immune system disease (T cell defect, leukemia and the like); locomotorium•skeletal system disease (bone fracture, osteoporosis, joint dislocation, subluxation, sprain, ligament injury, osteoarthritis, osteosarcoma, Ewing's sarcoma, dysostosis, achondroplasia, and the like); dermal system disease (atrichia, melanoma, cutaneous malignant lymphoma, angiosarcoma, histiocytosis, hydroa, pustlosis, dermatitis, eczema, and the like); endocrine system disease (hypothalamo-hypophysial disease, glandula thyroidea disease, glandula thyroidea accessoria (glandula parathyroidea) disease, adrenal cortex/medulla disease, sugar metabolic disorder, lipid metabolic disorder, protein metabolic disorder, nucleic acid metabolic disorder, congenital metabolic disorder (phenylketonuria, galactosemia, homocystinuria, maple syrup urine disease), analbuminemia, ascorbic acid synthetic ability absence, hyperbilirubinemia, hyperbilirubinurea, kallikrein deficiency, mast cell defect, diabetes insipidus, vasopressin secretion disorder, dwarfism, Wolman (acid lipase deficiency), mucopolysaccharidosis VI, and the like); respiratory system disease (pulmonary disease (for example, pneumonia, lung cancer, and the like), bronchial disease, lung cancer, bronchial cancer, and the like); alimentary system disease (esophageal disease (for example, esophageal cancer), gastric/duodenal disease (for example, gastric cancer, duodenal cancer), small intestine disease/large intestine disease (for example, colon polyp, colon cancer, rectal cancer and the like), biliary tract disease, liver disease (for example, cirrhosis hepatis, hepatitis (A, B, C, D, E, and the like), fulminant hepatitis, chronic hepatitis, primary hepatic cancer, alcoholic liver disease, drug-induced hepatitis), pancreatic disease (acute pancreatitis, chronic pancreatitis, pancreatic cancer, cystic pancreatic disease), peritoneum/abdominal wall/diaphragma disease (hernia and he like), hirschsprung's disease and the like); urinary system disease (renal disease (renal failure, primary glomerular disease, renovascular disorder, abnormal renal tubular function, interstitial renal disease, renal disorder induced by generalized disease, renal cancer, and the like), bladder disease (cystitis, bladder cancer and the like), and the like); genital organ disease (male genital organ disease (sterilitas virilis, prostate hypertrophy, prostate cancer, testicle cancer and the like), female genital organ disease (sterilitas feminia, ovarian function disorder, uterus myoma, uterine adenomyosis, uterus cancer, endometriosis, ovarian cancer, chorionic disease and the like), and the like); circulatory system disease (cardiac failure, cardiac angina, cardiac infarction, arrhythmia, valvular disease, cardiac muscle/pericardium disease, congenital cardiac disease (for example, interatrial septal defect, interatrial septal defect, patent ductus arteriosus, tetralogy of Fallot), artery disease (for example, arteriosclerosis, aneurysm), veins disease (for example, varix), lymphatic vessel disease (for example, lymphedema) and the like); and the like, but not limited to these.

As used herein, "sample" may be derived from any origin as long as it is aimed to separate, concentrate, purify, or analyze at least one component included therein (preferably, sugar chains or sugar chain-containing substance). Thus, a sample may be taken out from its entirety or part of a living organism, but not limited to these. In another embodiment, a sample may be synthesized using synthesis techniques.

As used herein, the term "biomolecule" refers to a molecule related to living bodies. A sample including such biomolecule may be referred to as a biological sample in the present specification. As used herein, "living body" refers to a biological organic body, and includes animals, plants, fungi, virus and the like, but not limited to these. Therefore, a biomolecule includes a molecule extracted from living bodies. However, it is not limited to this, and any molecule may fall within the definition of the biomolecule as long as it can affect living bodies. Such biomolecules includes protein, polypeptide, olygopeptide, peptide, polynucleotide, olygonucleotide, nucleotide, nucleic acid (including, for example, DNA such as cDNA, genome DNA, RNA such as mRNA), polysaccharide, olygosaccharide, lipid, small molecule (for example, hormone, ligand, signaling substance, organic small molecule and the like), complex molecule thereof, and the like, but not limited to these. As used herein, the biomolecules may be, preferably, complex molecules including sugar chains or sugar chains (for example, glycoprotein, glycolipid and the like).

The source of such a biomolecule is not particularly limited as long it is a material to which sugar chains derived from living organisms are bound or attached. It may be animal, plant, bacterial, or viral. A biological sample derived from an animal is preferable. For example, whole blood, blood plasma, blood serum, sweat, saliva, urine, pancreatic fluid, amnionic fluid, cerebrospinal fluid and the like are preferable. More preferably, it may be blood plasma, blood serum, or urine. The biological sample includes a biological sample which has not not previously been isoloated from a subject. The biological sample may include, for example, mucosal tissue or glandular tissue to which a sample can be attached from the outside, and preferably, the epithelium of ductal tissue attached to the mammary gland, prostate, or pancreas.

(Sugar Chain Array and Sugar Chain Chip)

The term "array" as used herein refers to a fixed pattern of a fixing material onto a substrate or a film or a patterned substrate itself. Amongst arrays, those which are patterned on small substrates (having the size of, for example, 10×10 mm, or the like) are called microarrays. However, in the present specification, microarray and array are used interchangeably. Further, arrays can be grouped into macroarrays and microarrays depending upon the size of the substrate or the density of the biomolecules to be placed thereon. Thus, biomolecules patterned on substrates larger than that described above, may even be called microarrays. For example, an array is formed of a set of desired biomolecules (for example, sugar chains) fixed to a solid phase surface or a film. An array includes at least $10^2$, preferably, at least $10^3$, more preferably, at least $10^4$, and yet more preferably, at least $10^5$ of different desired biomolecules (for example, sugar chains). These desired biomolecules (for example, sugar chains) are placed onto a surface having the area of, preferably, 125×80 mm, more preferably, 10×10 mm. The intended format ranges from the size of a 96 well plate, a 384 well plate and the like, to about the size of a glass slide.

Therefore, "array" or "microarray" can also be explained as a device obtained by arraying and fixing biomolecules (for example, sugar chains, proteins, nucleic acids or the like) on a substrate. In the present specification, array and microarray are interchangeably used unless otherwise noted. The boundary between macro and micro is not specifically defined. However, in general, "macroarray" refers to a high density filter having biomolecules spotted on a membrane, and "microarray" refers to an arrangement of biomolecules placed on a surface of a substrate such as glass, silicon, and the like.

As used herein, "chip" refers to arrays produced by synthesizing a plurality of types of biomolecules such as sugar chains on a substrate at the same time by applying techniques used for semiconductor integrated circuits. If the biomolecules are sugar chains, the chip is specifically called a "sugar chains chip", named after semiconductor chips. If the biomolecules are DNAs, the chip may be called a DNA chip. Such a chip may be GeneChip (TR) (Affimetrix, CA, USA) (See Marshall A et al., (1998) Nat. Biotechnol, 16:27-31 and Ramsay G et al., (1998) Nat. Biotechnol. 16 40-44), techniques involved in utilizing chips may be applied to the sugar chain chips. The definition of the sugar chain chip is as described above in the narrow sense, but it may also represent the entire sugar chain arrays or sugar chain microarrays. Therefore, chips on which sugar chains are placed with high density may also be referred to as sugar chain chips.

On an array, a "spot" of biomolecules may be placed. As used herein, a "spot" refers to a certain set of biomolecules. As used herein, "spotting" refers to producing a certain spot of biomolecules on a certain support. Spotting may be performed by any kind of method, and such methods are well known in the field of art.

The term "address" as used herein refers to a unique position on a substrate, which can be distinguished from other unique positions. An address may have any shape which is appropriate for association with the spot having the address, and which allows a substance on each of the addresses is recognized from substances on other addresses (for example, optically). The shape for defining the address may be, for example, a circle, ellipse, square, rectangle, or irregular shape. Thus, although "address" may be used to for represent an abstract concept, and "spot" may be used to represent a specific concept, "address" and "spot" may be interchangeably used in the present specification when there is no need to differentiate them from each other.

The size which defines the addresses depends upon the size of the substrate, the number of the addresses on a particular substrate, an amount of an analyte and/or a reagent which is available, the size of minute particles and resolution required for any method in which the array is used. The size may be in the range of, for example, 1-2 nm to a few cm, but any size which matches the application of the array may be employed.

The spatial arrangement and shape which define the address is designed to match the specific application for which the microarray is used. The addresses may be densely placed, extensively dispersed, or sub-grouped into a desired pattern suitable for an analyte of a particular type.

In an assay using a sugar chain array, it is possible to detect a fluorescence signal hybridized to a sugar chain array by a fluorescence detector and the like. As such a detector, various types of detectors are available so far. For example, a group at Stanford University has developed an original type scanner. The scanner is a combination of a fluorescence microscope and a movable stage, is used for DNA arrays, and can also be used for sugar chain arrays (see http://cmgm.stanford.edu/pbrown). Conventional type gel fluorescence image analyzers, such as FMBIO (Hitachi Software Engineering Co., Ltd.), Storm (Molecular Dynamics) and the like can also be used to read sugar chain arrays if the density of the spots is not very high. Other available detectors may be ScanArray 4000, ScanArray 5000 (GeneralScanning; scan type (confocal type)), GMS418 Array Scanner (Takara Shuzo Co., Ltd.; scan type (confocal type)), Gene Tip Scanner (Nihon Laser Denshi KK; scan type (non-confocal type)), Gene Tac 2000 (Genomic Solutions; CCD camera type)).

The amount of data obtained from arrays is enormous. Thus, data analysis software for performing management of correspondence between clone and spot and data analysis is important. As such software, software attached to various types of detection systems developed for DNA arrays (Ermolaeva O et al. (1998) Nat. Genet. 20: 19-23) may be used. Further, as a database format, for example, formats developed for DNA chips may be modified for using with sugar chains.

(Sugar Chain Replica)

As used herein, "sugar chain replica" refers to transcripting sugar chains which are on a subject to be a targeted to a certain material (for example, a film, solid foil) in conditions which reflect conditions, contents, places and the like under which they naturally exist, and transcripted matter (for example, a film, solid foil) obtained as such. In the sugar chain replica, since the conditions, content, places and the like under which the sugar chains naturally exist, are reflected conditions of the subject from which the sugar chain replica was derived can be assessed faithfully and conveniently by examining the sugar chain replica.

As used herein, "solid foil" refers to a thin foil of a solid. A solid foil is formed of a material which can produce a sugar chain replica, and can have any shape and be formed of any material as long as it can stand inspection. Such a solid foil may be, for example, glass, silica, silicon, ceramic, silicon dioxide, plastic, metal (including alloy), natural and synthetic polymers (for example, polystyrene, cellulose, chitosan, dextran, and nylon), but is not limited to these. Preferably, it may be advantageous to use a transparent material for the sake of convenience of inspection. It is preferable that a solid foil is made of a material to which a label which can be detected by a certain sensor can be attached.

(Diagnosis)

As used herein, "detection" refers to identifying various parameters related to a disease, disorder, or condition of the subject, As used herein, "diagnosis" refers to identifying various parameters related to a disease, disorder, or condition of the subject, and determining the current staus of such a disease, disorder, or condition. By employing the method, apparatus, and system according to the present invention, sugar chains can be identified, and information on the identified sugar chains can be used to select various parameters related to the disease, disorder, or condition of the subject.

As used herein, differentiation refers to recognizing various parameters related to a disease, disorder, or condition of the subject. Thus, in the present specification, the concepts of "diagnosis" and "differentiation" overlap partially.

(Organic Chemistry)

As used herein, "alkyl" refers to a monovalent group generated when one hydrogen atom is lost from aliphatic hydrocarbon (alkane) such as methane, ethane, propane, and the like, and is represented by $C_nH_{2n+1}$— in general (herein, n is a positive integer). Alkyl may be a straight chain or a branched chain. As used herein, "substituted alkyl" refers to an alkyl having the H of an alkyl substituted by a substituent as defined below. Specific examples of such alkyls may be, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, C1-C11 alkyl or C1-C12 alkyl, C1-C2 substituted alkyl, C1-C3 substituted alkyl, C1-C4 substituted alkyl, C1-C5 substituted alkyl, C1-C6 substituted alkyl, C1-C7 substituted alkyl, C1-C8 substituted alkyl, C1-C9 substituted alkyl, C1-C10 substituted alkyl, C1-C11 substituted alkyl, or C1-C12 substituted alkyl. Herein, for example, C1-C10 alkyl denotes straight chain or branched alkyl having 1-10 carbon atoms, and examples may be methyl ($CH_3$—), ethyl ($C_2H_5$—), n-propyl ($CH_3CH_2CH_2$—), isopropyl (($CH_3)_2CH$—), n-butyl ($CH_3CH_2CH_2CH_2$—), n-pentyl ($CH_3CH_2CH_2CH_2CH_2$—), n-hexyl ($CH_3CH_2CH_2CH_2CH_2CH_2$—), n-heptyl ($CH_3CH_2CH_2CH_2CH_2CH_2CH_2$—), n-octyl ($CH_3CH_2CH_2CH_2CH_2CH_2CH_2CH_2$—) n-nonyl ($CH_3CH_2CH_2CH_2CH_2CH_2CH_2CH_2CH_2$—), n-decyl ($CH_3CH_2CH_2CH_2CH_2CH_2CH_2CH_2CH_2CH_2$—), —$C(CH_3)_2CH_2CH_2CH(CH_3)_2$, —$CH_2CH(CH_3)_2$. Further, for example, C1-C10 substituted alkyl refers to C1-C10 alkyl having one or more hydrogen atoms substituted by substituents.

As used herein, "optionally substituted alkyl" means that either of "alkyl" or "substituted alkyl" as defined above may be used.

As used herein, "alkylene" refers to a bivalent group generated when two hydrogen atoms are lost from an aliphatic hydrocarbon (alkane) such as methylene, ethylene, propylene, and, in general, is represented by —$C_nH_{2n}$— (herein, n is a positive integer). Alkylene may be a straight chain or a branched chain. As used herein, "substituted alkylene" refers to an alkylene having the H of the alkylene substituted by a substituent defined below. Specific examples of such alkylenes may be, C1-C2 alkylene, C1-C3 alkylene, C1-C4 alkylene, C1-C5 alkylene, C1-C6 alkylene, C1-C7 alkylene, C1-C8 alkylene, C1-C9 alkylene, C1-C10 alkylene, C1-C11 alkylene or C1-C12 alkylene, C1-C2 substituted alkylene, C1-C3 substituted alkylene, C1-C4 substituted alkylene, C1-C5 substituted alkylene, C1-C6 substituted alkylene, C1-C7 substituted alkylene, C1-C8 substituted alkylene, C1-C9 substituted alkylene, C1-C10 substituted alkylene, C1-C11 substituted alkylene or C1-C12 substituted alkylene. Herein, for example, C1-C10 alkylene refers to a straight chain or branched alkylene having 1-10 carbon atoms, and examples of such alkylene may be methylene (—$CH_2$—), ethylene (—$C_2H_4$—), n-propylene (—$CH_2CH_2CH_2$—), isopropylene (—$(CH_3)_2C$—), n-butylene (—$CH_2CH_2CH_2CH_2$—), n-pentylene (—$CH_2CH_2CH_2CH_2CH_2$—), n-hexylene (—$CH_2CH_2CH_2CH_2CH_2CH_2$—), n-heptylene (—$CH_2CH_2CH_2CH_2CH_2CH_2CH_2$—), n-octylene (—$CH_2CH_2CH_2CH_2CH_2CH_2CH_2CH_2$—), n-nonylene (—$CH_2CH_2CH_2CH_2CH_2CH_2CH_2CH_2CH_2$—), n-decylene (—$CH_2CH_2CH_2CH_2CH_2CH_2CH_2CH_2CH_2CH_2$—), —$CH_2C(CH_3)_2$—, and the like. Further, for example, C1-C10 substituted alkylene refers to C1-C10 alkylene which has one or more hydrogen atoms substituted by substituents. As used herein, "alkylene" may include one or more atoms selected from oxygen atoms and sulfur atoms.

As used herein, "optionally substituted alkylene" means that either "alkylene or "substituted alkylene" as defined above may be used.

As used herein, "cycloalkyl" refers to an alkyl having a cyclic structure. The term "substituted cycloalkyl" refers to a cycloalkyl having the H of the cycloalkyl substituted by a substituent defined below. Specific examples of cycloalkyls may be C3-C4 cycloalkyl, C3-C5 cycloalkyl, C3-C6 cycloalkyl, C3-C7 cycloalkyl, C3-C8 cycloalkyl, C3-C9 cycloalkyl, C3-C10 cycloalkyl, C3-C11 cycloalkyl, C3-C12 cycloalkyl, C3-C4 substituted cycloalkyl, C3-C5 substituted cycloalkyl, C3-C6 substituted cycloalkyl, C3-C7 substituted cycloalkyl, C3-C8 substituted cycloalkyl, C3-C9 substituted cycloalkyl, C3-C10 substituted cycloalkyl, C3-C11 substituted cycloalkyl or C3-C12 substituted cycloalkyl. For example, cycloalkyl may be cyclopropyl, cyclohexyl, or the like.

As used herein, "optionally substituted cycloalkyl" means that either "cycloalkyl" or "substituted cycloalkyl" as defined above may be used.

As used herein, "alkenyl" refers to a monovalent group generated when one hydrogen atom is lost from an aliphatic hydrocarbon having one double bond in a molecule, and, in general, is represented by $C_nH_{2n-1}$— (herein, n is a positive integer of 2 or higher). The term "substituted alkenyl" refers to an alkenyl having the H of the alkenyl substituted by a substituent as defined below. Specific examples of alkenyls may be C2-C3 alkenyl, C2-C4 alkenyl, C2-C5 alkenyl, C2-C6 alkenyl, C2-C7 alkenyl, C2-C8 alkenyl, C2-C9 alkenyl, C2-C10 alkenyl, C2-C11 alkenyl or C2-C12 alkenyl, C2-C3 substituted alkenyl, C2-C4 substituted alkenyl, C2-C5 substituted alkenyl, C2-C6 substituted alkenyl, C2-C7 substituted alkenyl, C2-C8 substituted alkenyl, C2-C9 substituted alkenyl, C2-C10 substituted alkenyl, C2-C11 substituted alkenyl or C2-C12 substituted alkenyl. Herein, for example, C2-C10 alkyl refers to a straight chain or branched alkenyl including 2-10 carbon atoms, and examples of alkyls include vinyl ($CH_2$—CH—), allyl ($CH_2$=$CHCH_2$—), $CH_3CH$=CH— and the like. Further, for example, C2-C10 substituted alkenyl refers to C2-C10 alkenyl which has 1 or more hydrogen atoms substituted by substituents.

As used herein, "optionally substituted alkenyl" means that either "alkenyl" or "substituted alkenyl" as defined above may be used.

As used herein, "alkenylene" refers to a bivalent group generated when two hydrogen atoms are lost from an aliphatic hydrocarbon having a double bond in a molecule, and, in general, is represented by —$C_nH_{2n-2}$— (herein, n is a positive integer of 2 or higher). The term substituted alkenylene" refers to an alkenylene having the H of the alkenylene substituted by a substituent defined as below. Specific examples may be C2-C25 alkenylene or C2-C25 substituted alkenylene. Particularly, C2-C3 alkenylene, C2-C4 alkenylene, C2-C5 alkenylene, C2-C6 alkenylene, C2-C7 alkenylene, C2-C8 alkenylene, C2-C9 alkenylene, C2-C10 alkenylene, C2-C11 alkenylene or C2-C12 alkenylene, C2-C3 substituted alkenylene, C2-C4 substituted alkenylene, C2-C5 substituted alkenylene, CZ-C6 substituted alkenylene, C2-C7 substituted alkenylene, C2-C8 substituted alkenylene, C2-C9 substituted alkenylene, C2-C10 substituted alkenylene, C2-C11 substituted alkenylene and C2-C12 substituted alkenylene are prefered. Herein, for example, C2-C10 alkyl refers to a straight chain or branched alkenylene including 2-10 carbon atoms, and examples of alkyl may be —CH=CH—, —CH=$CHCH_2$—, —($CH_3$)C=CH—, or the like. Further, for example, C2-C10 substituted alkenylene is C2-C10 alkenylene which has one or more hydrogen atoms substituted by substituents. As used herein, "alkenylene" may include one or more atoms selected from oxygen atoms and sulfur atoms.

As used herein, "optionally substituted alkenylene" means that either "alkenylene" or "substituted alkenylene" as defined above may be used.

As used herein, "cycloalkenyl" refers to an alkenyl having a cyclic structure. The term "substituted cycloalkenyl" refers to a cycloalkenyl having the H of a cycloalkenyl substituted by a substituent as defined below. Specific examples of cycloalkenyl may be C3-C4 cycloalkenyl, C3-C5 cycloalkenyl, C3-C6 cycloalkenyl, C3-C7 cycloalkenyl, C3-C8 cycloalkenyl, C3-C9 cycloalkenyl, C3-C10 cycloalkenyl, C3-C11 cycloalkenyl, C3-C12 cycloalkenyl, C3-C4 substituted cycloalkenyl, C3-C5 substituted cycloalkenyl, C3-C6 substituted cycloalkenyl, C3-C7 substituted cycloalkenyl, C3-C8 substituted cycloalkenyl, C3-C9 substituted cycloalkenyl, C3-C10 substituted cycloalkenyl, C3-C11 substituted cycloalkenyl or C3-C12 substituted cycloalkenyl. For example, preferable examples of cycloalkenyl include 1-cyclopentenyl, 2-cyclohexenyl or the like.

As used herein, "optionally substituted cycloalkenyl" means that either "cycloalkenyl" or "substituted cycloalkenyl" as defined above may be used.

As used herein, "alkynyl" refers to a monovalent group generated when one hydrogen atom is lost from an aliphatic hydrocarbon having one triple bond in a molecule, such as acetylene, and, in general, is represented by $C_nH_{2n-3}$— (herein, n is a positive integer of 2 or higher). The term "substituted alkynyl" refers to alkynyl having the H of the alkynyl substituted by a substituent as defined below. Specific examples of alkynyls may be C2-C3 alkynyl, C2-C4 alkynyl, C2-C5 alkynyl, C2-C6 alkynyl, C2-C7 alkynyl, C2-C8 alkynyl, C2-C9 alkynyl, C2-C10 alkynyl, C2-C11 alkynyl, C2-C12 alkynyl, C2-C3 substituted alkynyl, C2-C4 substituted alkynyl, C2-C5 substituted alkynyl, C2-C6 substituted alkynyl, C2-C7 substituted alkynyl, C2-C8 substituted alkynyl, C2-C9 substituted alkynyl, C2-C10 substituted alkynyl, C2-C11 substituted alkynyl or C2-C12 substituted alkynyl. Herein, for example, C2-C10 alkynyl refers to, for example, a straight chain or branched alkynyl including 2-10 carbon atoms, and examples of alkynyl may be ethynyl (CH≡C—), 1-propynyl ($CH_3$C≡C—) or the like. Further, for example, C2-C10 substituted alkynyl refers to C2-C10 alkynyl having 1 or more hydrogen atoms substituted by substituents.

As used herein, "optionally substituted alkynyl" means that either "alkynyl" or "substituted alkynyl" as defined above may be used.

As used herein, "alkoxy" refers to a monovalent group generated when a hydrogen atom of a hydroxy group of an alcohol is lost, and in general, is represented by $C_nH_{2n+1}$O— (herein, n is an integer of 1 or higher). The term "substituted alkoxy" refers to alkoxy having H of the alkoxy substituted by a substituent as defined below. Specific examples of alkoxys may be C1-C2 alkoxy, C1-C3 alkoxy, C1-C4 alkoxy, C1-C5 alkoxy, C1-C6 alkoxy, C1-C7 alkoxy, C1-C8 alkoxy, C1-C9 alkoxy, C1-C10 alkoxy, C1-C11 alkoxy, C1-C12 alkoxy, C1-C2 substituted alkoxy, C1-C3 substituted alkoxy, C1-C4 substituted alkoxy, C1-C5 substituted alkoxy, C1-C6 substituted alkoxy, C1-C7 substituted alkoxy, C1-C8 substituted alkoxy, C1-C9 substituted alkoxy, C1-C10 substituted alkoxy, C1-C11 substituted alkoxy or C1-C12 substituted alkoxy. Herein, for example, C1-C10 alkoxy refers to a straight chain or branched alkoxy including 1-10 carbon atoms, and examples of alkoxys may be methoxy ($CH_3$O—), ethoxy ($C_2H_5$O—), n-propoxy ($CH_3CH_2CH_2$O—), and the like.

As used herein, "alkoxy which may be substituted" means that either "alkoxy" or "substituted alkoxy" as defined above may be used.

As used herein, "heterocycle (group)" refers to a group having a cyclic structure including carbon and hetero atoms. Herein, hetero atoms may be selected from a group consisting O, S and N, may be the same or different from each other, and one or more of them may be included. A heterocyclic group may be aromatic or nonaromatic, and may be monocyclic or polycyclic. The heterocyclic group may be substituted.

As used herein, "heterocycle (group) which may be substituted" means that either "heterocycle (group)" or "substituted heterocycle (group)" as defined above may be used.

As used herein, "alcohol" refers to an organic compound having 1 or more hydrogen atoms of an aliphatic hydrocarbon substituted by a hydroxyl group. It is also represented as ROH in the present specification. Herein, R is an alkyl group.

Preferably, R may be C1-C6 alkyl. Alcohol may be, for example, methanol, ethanol, 1-propanol, 2-propanol and the like, but is not limited to these.

As used herein, "carbocyclic group" refers to a group which includes a cyclic structure including only carbons, and which is a group other than the above-mentioned "cycloalkyl", "substituted cycloalkyl" "cycloalkenyl", and "substituted cycloalkenyl". A carbocyclic group may be aromatic or nonaromatic, and may be monocyclic or polycyclic. The term "substituted carbocyclic group" refers to a carbocyclic group having the H of the carbocyclic group substituted by a substituent as defined below. Specific examples of carbocyclic groups may be C3-C4 carbocyclic group, C3-C5 carbocyclic group, C3-C6 carbocyclic group, C3-C7 carbocyclic group, C3-C8 carbocyclic group, C3-C9 carbocyclic group, C3-C10 carbocyclic group, C3-C11 carbocyclic group, C3-C12 carbocyclic group, C3-C4 substituted carbocyclic group, C3-C5 substituted carbocyclic group, C3-C6 substituted carbocyclic group, C3-C7 substituted carbocyclic group, C3-C8 substituted carbocyclic group, C3-C9 substituted carbocyclic group, C3-C10 substituted carbocyclic group, C3-C11 substituted carbocyclic group, or C3-C12 substituted carbocyclic group. The carbocyclic group may also be C4-C7 carbocyclic group or C4-C7 substituted carbocyclic group. The examples of carbocyclic group may be a phenyl group having one hydrogen atom deleted. The deletion site of the hydrogen may be any site which is chemically possible, and it may be on an aromatic ring or on a nonaromatic ring.

As used herein, "carbocyclic group which may be substituted" means that either "carbocyclic group" or "substituted carbocyclic group" as defined above may be used.

As used herein, "heterocyclic group" refers to a group having a cyclic structure including carbon and hetero atoms. Herein, hetero atoms may be selected from a group consisting of O, S and N, may be the same or different from each other, and one or more atoms may be included. A heterocyclic group may be aromatic or nonaromatic, and may be monocyclic or polycyclic. The term "substituted heterocyclic group" refers to a heterocyclic group having the H of the heterocyclic group substituted by a substituent as defined below. Specific examples of heterocyclic group may be C3-C4 carbocyclic group, C3-C5 carbocyclic group, C3-C6 carbocyclic group, C3-C7 carbocyclic group, C3-C8 carbocyclic group, C3-C9 carbocyclic group, C3-C10 carbocyclic group, C3-C11 carbocyclic group, C3-C12 carbocyclic group, C3-C4 substituted carbocyclic group, C3-C5 substituted carbocyclic group, C3-C6 substituted carbocyclic group, C3-C7 substituted carbocyclic group, C3-C8 substituted carbocyclic group, C3-C9 substituted carbocyclic group, C3-C10 substituted carbocyclic group, C3-C11 substituted carbocyclic group, or C3-C12 substituted carbocyclic group, which has one or more carbon atoms substituted by heteroatoms. The heterocyclic group may also be a C4-C7 carbocyclic group or C4-C7 substituted carbocyclic group, which has one or more carbon atoms substituted with hetero atoms. The examples of heterocyclic groups may be a thienyl group, pyrrolyl group, furyl group, imidazolyl group, pyridyl group, or the like. The deletion site of the hydrogen may be any site which is chemically possible, and it may be on an aromatic ring or on a nonaromatic ring.

As used herein, carbocyclic group or heterocyclic group may be substituted by a bivalent substituent in addition to being able to be substituted by a monovalent substituent as defined below. Such a bivalent substitution may be oxo substitution (=O) or thioxo substitution (=S).

As used herein, "halogen" refers to a monovalent group of elements such as fluorine (F), chlorine (Cl), bromine (Br), iodine (I) and the like which belong to group 7B of the periodic table.

As used herein, "hydroxy" refers to a group represented by —OH. The term "substituted hydroxy" refers to hydroxy having the H of the hydroxy substituted by a substituent as defined below.

As used herein, "thiol" (mercapto group) is a group having the oxygen atom of a hydroxy group substituted by a sulfur atom, and is represented by —SH. The term "substituted thiol" refers to a group having the H of a mercapto group substituted by a substituent as defined below.

As used herein, "cyano" refers to a group represented by —CN, and "nitro" refers to a group represented by —NO$_2$. The term "amino" refers to a group represented by —NH$_2$. The term "substituted amino" refers to amino having an H substituted by a substituent defined below.

As used herein, "carboxy" refers to a group represented by —COOH. The term "substituted carboxy" is carboxy having an H substituted by a substituent as defined below.

As used herein, "thiocarboxy" refers to a group having an oxygen atom of carboxy group substituted with a sulfur atom, and can be represented by —C(=S)OH, —C(=O)SH or —CSSH. The term "substituted thiocarboxy" is thiocarboxy having the H substituted by a substituent as defined below.

As used herein, "acyl" refers to a monovalent group generated by removing OH from carboxylic acid. Representative examples of acyl groups may be, acetyl (CH$_3$CO—), benzoyl (C$_6$H$_5$CO—), and the like. The term "substituted acyl" refers to acyl having hydrogen substituted by a substituent as defined below.

As used herein, "amide" refers to a group having a hydrogen of ammonia substituted with an acid group (acyl group), and, preferably, represented by —CONH$_2$. The term "substituted amide" refers to amide which is substituted by a substituent as defined below.

As used herein, "carbonyl" refers to a generic term for a substance including —(C=O)—, which is a specific group of aldehydes and ketones. The term "substituted carbonyl" refers to a carbonyl group substituted by a substituent selected as described below.

As used herein, "thiocarbonyl" refers to a group having the oxygen atom of carbonyl substituted by a sulfur atom, and includes a specific group —(C=S)—. The thiocarbonyl includes thioketone and thioaldehyde. The term "substituted thiocarbonyl" refers to a thiocarbonyl substituted by a substituent selected as described below.

As used herein, "sulfonyl" is a generic term for a substance including a specific group, —SO$_2$—. The term "substituted sulfonyl" refers to a sulfonyl substituted by a substituent selected as described below.

As used herein, "sulfinyl" is a generic term for a substance including a specific group, —SO—. The term "substituted sulfinyl" refers to a sulfinyl substituted by a substituent selected as described below.

As used herein, "aryl" refers to a group generated when one hydrogen atom linked to a ring of aromatic hydrocarbons is disengaged, and included in a carbocyclic group in the present specification.

As used herein, unless otherwise noted, the term "substitution" refers to substituting one ore more hydrogen atoms in an organic compound or a substituent by another atom or atomic group. It is possible to remove one hydrogen atom and substitute with a monovalent substituent, and remove two hydrogen atoms and substitute with a bivalent substituent.

As used herein, unless otherwise noted, the term "substitution" refers to substituting one ore more hydrogen atoms in an organic compound or a substituent by another atom or atomic group. It is possible to remove one hydrogen atom and substitute with a monovalent substituent, and remove two hydrogen atoms and substitute with a bivalent substituent.

The substituent in the present invention may be alkyl, cycloalkyl, alkenyl, cycloalkenyl, alkynyl, alkoxy, carbocyclic group, heterocyclic group, halogen, hydroxy, thiol, cyano, nitro, amino, carboxy, carbamoyl, acyl, acylamino, thiocarboxy, amide, substituted carbonyl, substituted thiocarbonyl, substituted sulfonyl or substituted sulfinyl, but is not limited to these.

Preferably, when there is a plurality of substituents, they may be independently hydrogen atoms or alkyls, but not all the plurality of substituents are hydrogen atoms. More preferably, when there is a plurality of substituents, they may be independently selected from the group consisting of hydrogens and C1-C6 alkyls. The substituents may include substituents which are all not hydrogens, but preferably, may include at least one hydrogen, and more preferably, 2–n (herein, n is the number of substituents) hydrogens. Substituents having a large number of hydrogens may be preferable. This is because large substituents or substituents with polarity may prove to be obstacles to effects of the present invention (particularly, interaction with aldehyde groups). Thus, substituents other than hydrogens may be, preferably, C1-C6 alkyl, C1-C5 alkyl, C1-C4 alkyl, C1-C3 alkyl, C1-C2 alkyl, methyl, or the like. However, it may also be preferable to have large substituents since they sometime improve the effects of the present invention.

As used herein, C1, C2, . . . Cn represents the number of carbons. Thus, C1 is used to represent a substituent with one carbon.

As used herein, "enantiomer" refers to one of a pair of compounds which cannot be superimposed since the structure of their crystals or molecules are mirror images of one another, or the pair itself. Enantiomers are a type of stereoisomer, and all of their properties, other than optical rotation, are same.

As used herein, "protection reaction" refers to a reaction to add a protecting group such as Boc to a functional group which is desired to be protected. By protecting a functional group with a protecting group, the reaction of a functional group having high reactivity can be suppressed, and only a functional group having lower reactivity reacts.

As used herein, "deprotection reaction" refers to a reaction to disengage a protecting group such as Boc. The deprotection reaction may be a reaction such as a reduction reaction using Pd/C.

In the methods of the present invention, intended products may be isolated by removing foreign substances (unreacted raw material, by-product, solvent and the like) from a reaction solution using a method commonly used in the field of art (for example, extraction, distillation, washing, concentration, precipitation, filtration, drying or the like), and then combining after treatment methods commonly used in the field of art (for example, adsorption, dissolution, elution, distillation, precipitation, deposition, chromatography, or the like).

(General Techniques Used in the Present Specification)

The techniques used in the present specification are, unless otherwise noted specifically, well-known commonly used techniques in microfluidics, microfabrication, organic chemistry, biochemistry, genetic engineering, molecular biology, microbiology, genetics and related fields within the technical range of the field of art. Such techniques are sufficiently disclosed in, for example, documents which will be listed below and documents cited in other parts of the present specification.

Microfabrication is described in, for example: Campbell, S. A. (1996) The Science and Engineering of Microelectronic Fabrication, Oxford University Press; Zaut, P. V. (1996) Micromicroarray Fabrication: a Practical Guide to Semiconductor Processing, Semiconductor Services; Madou, M. J. (1997) Fundamentals of Microfabrication, CRC1 5 Press; Rai-Choudhury, P. (1997) Handbook of Microlithography, Micromachining, & Microfabrication: Microlithography; and the like. The relevant portions of these documents are herein incorporated.

Molecular biological methods, biochemical methods, microbiological methods used in the present specification are those well-known and commonly used in the art, and are disclosed in, for example: Maniatis, T. et al. (1989) Molecular Cloning: A Laboratory Manual, Cold Spring Harbor and 3rd Ed. Thereof (2001); Ausubel, F. M., at al. eds, Current Protocols in Molecular Biology, John Wiley & Sons Inc., NY, 10158 (2000); Innis, M. A. (1990). PCR Protocols: A Guide to Methods and Applications, Academic Press: Innis, M. A. et al. (1995) PCR Strategies, Academic Press; Sninsky, J. J. et al. (1999) PCR Applications: Protocols for Functional Genomics, Academic Press; Gait, M. J. (1985) Oligonucleotide Synthesis: A Practical Approach, IRL Press; Gait, M. J. (1990) Oligonucleotide Synthesis: A Practical Approach, IRL Press; Eckstein, F. (1991) Oligonucleotides and Analogues: A Practical Approach, IRL Press; Adams, R. L. et al. (1992) The Biochemistry of the Nucleic Acids, Chapman & Hall; Shabarova, Z. et al. (1994) Advanced Organic Chemistry of Nucleic Acids, Weinheim; Blackburn, G. M. et al. (1996) Nucleic Acids in Chemistry and Biology, Oxford University Press; Hermanson, G. T. (1996) Bioconjugate Techniques, Academic Press; Method in Enzymology 230, 242, 247, Academic Press, 1994; Bessatsu Jikkenn Igaku (Separate volume of Experimental Medicine) "Idenshidonyu & Hatsugen Kaiseki Jikkenho (Gene Introduction & Expression Analysis Experimental Method)", Yodosha Co. Ltd., 1997; Hatanaka, Nishimura, et. al., "Toshitsu no Kagaku to Kogaku (Science and engineering of Glucids)", Kodansha Scientific KK, 1997; Tosabunshi no Sekkei to Seirikino (Design and Physiology of Sugar Chain Molecules) Chemical Society of Japan ed., Japan Scientific Societies Press, 2001; and the like. The relevant portions (these may be the entirety) of these documents are herein incorporated.

(Screening)

As used herein, "screening" refers to selecting a substance or living organism having a specific property which is a target by a specific operation and/or evaluation method, from a large number of candidates. In the present specification, screening can be performed by using an apparatus, system, sugar chain array or the like of the present invention. For screening, a system using actual substances such as in vitro systems, in vivo systems and the like may be used, or a library produced by using an in silico system (a system using a computer) may be used. It should be understood that, in the present invention, compounds obtained by screening having desired activities are also within the scope of the present invention. Furthermore, the present invention intends that a medicine obtained by a computer modeling is provided, based on the disclosure of the present invention.

(Measurement of Sugar Chains)

The sugar chains separated, purified, or concentrated by a method, apparatus and system of the present invention can be identified by various physical methods (mass spectroscopy analysts, NMR, X-ray analysis, elemental analysis and the like), chemical methods (observation of specific chemical reactions and the like), biochemical methods (determining the substrate specificity and the like of enzymes), or biological methods (reactions of living organisms (for example, micro organisms such as bacteria)).

Techniques of mass spectroscopy analysis, NMR analysis which are used as physical methods are well-known in the art, and, reference can be made to, for example: Niwa, Saishin no Masusupekutorometori (Latest Mass spectroscopy), Kagakudojin Publishing Company, Ltd., 1995; Modern NMR Spectroscopy: A guide for Chemists, J. K. M. Sanders and B. K. Hunter (2nd Ed., Oxford University Press, New York, 1993); Spectrometric Identification of organic Compounds, R. M. Silverstein, G. Clayton Bassler, and Terrence C. Morill (5th Ed., John Wiley & Sons, New York, 1991); and the like.

(Probe Used for Quantitative or Qualitative Analysis of Sugar Chains)

In another embodiment, sugar chains separated by the method of the present invention can be analyzed using biochemical methods.

In such biochemical methods, test probes used for sugar chain analysis in the present specification may be any kind of test probes as long as they can specifically bind to sugar chains, and are labeled so as to enable detection. Such probes may be, for example, a substance which specifically interacts with sugar chains of the present invention, lectin, sugar chain recognition antibodies, or the like, which are labeled, but are not limited to these.

The quantitative determination of sugar chains may be absolute or relative. Absolute quantitative determination can be performed by, for example, creating a standard curve using one or more target sugar chains of known concentration as a standard. Alternatively, relative quantitative determination can be achieved by comparing the signal intensities of two ore more types of sugar chains of a transcription material. Such an analysis can be performed by a computer system. A software for performing such an analysis may be, for example, ArrayGauge Ver. 1.2, or ImageGauge Ver. 3.45 (both available from Fuji Photo Film Co., Ltd.), but is not limited to these.

The terms "label" and "mark" are used to have the same meanings in the present specification, and refer to entity (for example, substance, energy, electromagnetic wave, or the like) for distinguishing the target molecule or substance from others. Such labeling methods may be a radioisotope (RI) method, fluorescence method, biotin method, chemiluminescence method or the like.

(Medicines, Cosmetics, etc. and Treatment, Prevention, etc. Using the Same)

In another aspect, the present invention relates to medicines (for example, medicines such as vaccines and the like, healthy foods, medicines having reduced antigenicity of a residual protein or lipid) and cosmetics. The medicines and cosmetics may further include pharmaceutically acceptable carriers and the like. The pharmaceutically acceptable carriers included in the medicines of the present invention may be any substance known in the field of art.

Such appropriate prescription materials or pharmaceutically acceptable carriers may be antioxidant agents, preservatives, colorants, flavoring, diluents, emulsifiers, suspending agents, solvents, fillers, extending agents, buffers, delivery vehicles, diluents, excipiens and/or pharmaceutical adjuvants, but are not limited to these. Typically, medicines of the present invention are administered in the form of compositions including an isolated pluripotent stem cell, or modification or derivative thereof, together with one or more physiologically acceptable carriers, excipients or diluents.

Appropriate vehicles may be, for example, injection solvents, physiological solutions, or artificial cerebrospinal fluid. Other substances common in compositions for parenteral delivery may be complemented thereto.

The acceptable carriers, excipient or stabilizing agents are nontoxic to recipients, and, preferably, inactive at the dosage and concentration used. They may be: phosphate, citrate, or other organic acids; ascorbic acid, α-tocopherol; low molecular weight polypeptides; proteins (for example, serum albumin, gelatin or immunoglobulin); hydrophilic polymers (for example, polyvinylpyrrolidone); amino acids (for example, glycine, glutamine, asparagine, arginine or lysine); monosaccharides, disaccharides and other carbohydrates (including glucose, mannose, or dextrin); chelators (for example, EDTA); sugar alcohols (for example, mannitol or sorbitol); salt-forming counterions (for example, sodium); and/or nonionic surfactants (for example, Tween, pluronic or polyethylene glycol (PEG)).

Exemplary appropriate carriers may be, neutral buffered saline, or saline mixed with serum albumin. Preferably, products thereof are prepared as a lyophilization agent by using appropriate excipients (for example, sucrose). Other normal carriers, diluents and excipients may be included when desired. Other exemplary compositions include Tris buffer pH 7.0-8.5 or acetic acid buffer of pH 4.0-5.5, and may further include sorbitol or appropriate alternatives thereof.

The medicines of the present invention may administered orally or parenterally. Alternatively, the medicines of the present invention may be administered intravenously or subcutaneously. For systemic administration, medicines of the present invention may be in the form of pharmaceutically acceptable aqueous solutions which do not include pyrogenic substances. Preparation of such pharmaceutically acceptable compositions can be readily performed by those skilled in the art, taking pH, isotonicity, stability and the like into consideration. In the present specification, administration methods may be oral administration, parenteral administration (for example, intravenous administration, intramuscular administration, subcutaneous administration, intradermal administration, mucosal administration, intrarectal administration, intravaginal administration, local administration to affected parts, percutaneous administration and the like). Formulations for such administrations may be provided in any form of drug. Such a form of drug may be, for example, a liquid preparation, an injection, or a sustained-released preparation.

The medicines of the present invention may be prepared and preserved in the form of a lyophilized cake or an aqueous solution by mixing physiologically acceptable carriers, excipients or stabilizing agents (see Pharmacopeia of Japan, 14th edition or the latest edition, Remington's Pharmaceutical Sciences, 18th Edition, A. R. Gennaro, ed., Mack Publishing Company, 1990, and the like) with a sugar chain composition having a desired purity as necessary.

The amount of the sugar chain compositions used in the treatment methods of the present invention can be readily determined by those skilled in the art taking the object of use, target disease (type, severity and the like), age, weight, sex, past history of the patient, forms or types of cells, and the like into consideration. Frequency of applying the treatment methods of the present invention to a subject (or patient) can also be readily determined by those skilled in the art taking the object of use, target disease (type, severity and the like), age, weight, sex, past history of the patient, and therapeutic course into consideration. Frequency of administration may be, for example, once a day to once every few months (for example, once a week to once a month). It is preferable to provide administration of once in a week to once in a month while observing the course.

When the present invention is applied to cosmetics, the cosmetics may be prepared in conformity to regulations defined by authorities.

(Agricultural Chemical)

The composition of the present invention can be used as a component of agricultural chemicals. When the composition is prescribed as agricultural chemical composition, it may include agriculturally acceptable carriers, excipients or stabilizing agents as necessary.

When the composition of the present invention is used as an agricultural chemical, herbicide (pyrazolate and the like), insecticide/miticide (diazinon and the like), bactericide (probezanol and the like), plant growth regulator (e.g., paclobutrazol and the like), nematicide (e.g., benomyl and the like), synergist (e.g., piperonyl butoxide and the like), attractant (e.g., eugenol and the like), rejectant (e.g., creosote and the like), colorant (e.g., edible dye Blue No. 1 and the like), fertilizer (e.g., urea and the like) may be mixed as necessary.

(Healthcare/Food)

The present invention can also be used in the field of healthcare and food. In such cases, things to bear in mind when preparing oral medicines, as described above, should be considered as necessary. Particularly, when used for functional food or healthy food such as food for specified health use, handling which conforms to that for medicines is preferable. Preferably, a sugar chain composition of the present invention may also be used for low allergen foods.

As described above, the present invention may be applied to, besides medical care, anything which requires biomolecular testing in the fields of food inspection, quarantine, medicine inspection, forensic medicine, agriculture, animal industry, fishery, forestry and the like. In particular the present invention is intended to be used to secure the safety of food (for example, BSE inspection).

(Inspection)

The method, apparatus, system of the present invention can be used for detecting various sugar chains, and can be used for various inspections, diagnoses, determination, and differentiation since the type of sugar chains to be detected is not specifically limited. The sugar chains detected as such may be sugar chains specific to, for example: genes of virual pathogenic agents (including, for example, hepatitis virus (Type A, B, C, D, E, F, or G), HIV, influenza virus, herpes virus, adenovirus, human polyomavirus, human papillomavirus, human parvovirus, mumps virus, human rotavirus, enterovirus, Japanese encephalitis virus, dengue virus, rubella virus, and HTLV, but not limited to these); genes of bacterial pathogenic agents (including, for example, *Staphylococcus aureus, Streptococcus haemolyticus, Escherichia coliform bacillus, Vibrio parahaemolyticus, Helicobacter pylori, Campylobacter, Vibrio cholerae, Bacillus dysenteriae, Salmonella typhimurium, Yersinia, Neisseria gonorrhoeae, Listeria monocytogenes, Leptospira, Legionella, Spirochaeta, Mycoplasma pneumonia, rickettsia*, and *Chlamydia*, but not limited to these), malaria, *Entamoeba histolytica*, pathogenesis fungus, parasite, fungus, and the like.

Alternatively, the present invention may also be used for detecting biochemical inspection data. Targets for such biochemical inspection may be sugar chains such as, cholinesterase, alkaline phosphatase, leucine aminopeptidase, γ-glutamyl transpeptidase, creatinine phoskinase, lactate dehydrogenase, amylase and the like are related, but are not limited to these.

(Polymeric Material)

The present invention can also be applied in fields which are not related to biomolecules. In such a case, materials can be prepared, taking advantage of the properties that the present invention has achieved, i.e., interacting with all sugar chains to essentially the same degree, and being able to perform separation, purification, concentration and analysis. Particularly, in the case where sugar chains or a sugar chain-containing substance are used as a material such as a biodegradable polymer, the present invention may be advantageous, if it is desired to maintain the same sugar chain ratio as the original, in a sample. Alternatively, in the case where sugar chains or sugar chain-containing substances are synthesized in a bulk, if it is preferable to purify the sugar chains and sugar chain-containing substance while maintaining the same composite ratio as that at the time of synthesis, the substance, method, apparatus and system of the present invention may be advantageous.

As described above, the method, apparatus and system of the present invention may be used in, for example, diagnosis, forensic medicine, drug discovery (screening medicines) and development, molecular biological analysis (for example, array-based sugar chains analysis), sugar chains property and function analysis, pharmacology, Glycomics, environmental assessment, and further biological and chemical analysis.

(Description of Preferable Embodiments)

Hereinafter, preferable embodiments of the present invention will be described.

In one aspect, the present invention provides a substance which can specifically interact with sugar chains. The substance preferably has the property that it has specificity to sugar chains higher than it's specificity to substantially all substances which does not include sugar chains. In the conventional art, a number of substances which preferentially bind to sugar chains or sugar chain-containing substances are known. However, such substances may also have specificities to substances other than sugar chains and sugar chain-containing substances. The present invention has the effect of improving such specificity.

The substance which specifically interacts with sugar chains of the present invention can be represented by the schematic figure of (A)-(B). Herein, (A) denotes a portion having a functional group which specifically interacts with sugar chains (for example, a portion including a functional group which can react with an aldehyde group in a fluid), (B) denotes a portion which has nothing to do with a functional group which specifically interacts with sugar chains (for example, lipid). Preferably, (B) may be a portion which can bind to a support or a portion which can be used as a support. Specific examples of the portion which is represented by (A) may be compounds represented by formula (I), and specific examples of the portion represented by (B) are compounds represented by formula (II). (A)-(B) may be further substituted by the substituents as defined above. The number of the substituents may vary depending on the structure of (A)-(B), and may be the same as the number of existing hydrogens.

The interaction of the present invention preferably includes a covalent bond. This is because a covalent bond allows features of the present invention such as purification, separation, concentration and analysis to be performed more advantageously and conveniently. More preferably, such a covalent bond includes a bond selected from the group consisting of oxime bonding, hydrazone bonding, thiosemihydrazone bonding, perhydrothiazine ring formation and thiazolidine ring formation. Such bonds have high specificity to sugar chains. Thus they act advantageously for securing specificity.

Particularly, a substance which can specifically interact with sugar chains which can bind to a support (particularly, a solid support), or which can be used as a support itself is not known in the conventional art, nor has there been any attempt to prepare such substance. Thus, the present invention shows a significant effect in providing such substance. Herein, the substance which can specifically interact with sugar chains of the present invention preferably has the property that phase transition of at least a part of a support and the substance may occur. Preferably, such support and substance may have the property that phase transition of all of them occurs. In use as a support, when a reaction takes place in a fluid, it phase transition has not occurred, it returns to equilibrium state and bonds are released, and thus, the desired reaction and/or assay cannot be performed, or becomes inefficient. Such a support is, typically, solid at a normal temperature. However, as long as it can be used for concentration, purification, separation or analysis, it may be a fluid such as liquid or gas.

In the preferred embodiment, the substance which can specifically interact with sugar chains of the present invention may specifically interact with any sugar chains at a predetermined level or higher. Herein, the predetermined level refers to a level sufficient for determining whether the substance performs an interaction specific to sugar chains. The property to specifically react with any sugar chain at a predetermined level or higher can achieve significant effects as described below, compared to the property of specifically interacting with a specific sugar chain. For example, by interacting with any sugar chains with no discrimination, sugar chains and sugar chain-containing substances can be concentrated, purified, or separated while maintaining the content ratio when it naturally exists, or the content ration can be analyzed. Since the natural state can be reflected, the state of the subject which can be determined based on the sugar chains can be readily determined from a sample taken from the subject.

Specifically, the level of interaction between the above-described substance and the sugar chains can be determined by the dissociation energy required when laser irradiation is performed during MALDI-TOF. In such a state, necessary dissociation energy is at least about 5 eV, preferably at least about 10 eV, and more preferably at least about 15 eV.

Alternatively, the level of interaction can be determined by other physical methods. Examples of physical methods may be a method for estimating the bonding amount of sugar chains by a surface plasmon resonance method, and a level determination of such based on NMR proton signal intensity derived from oxime bonding between sugar chain-trapping carriers.

Alternatively, the level of interaction can be determined by a chemical method. An example of a chemical method may be estimating the level of interaction based on the separation pattern of thin layer chromatography (TLC).

Alternatively, level of interaction may be determined by a biochemical method. An example of a biochemical method may be determining the level of interaction by an ELISA method using sugar chain-specific antibodies.

Preferably, when the substance of the present invention is exposed to conditions that dissociate nonspecific interaction with substances other than sugar chains, at least a certain amount of specific interaction with sugar chains remains. Since at least a certain amount of specific interaction with sugar chains remains, the substance of the present invention can be used for purification, concentration, separation and analysis of the sugar chains and sugar chain-containing substance. Particularly, the property that even when the substance is exposed to conditions that dissociate nonspecific interactions with substances other than sugar chains, at least a certain amount of specific interaction with sugar chains remain, enableing substances other than sugar chains to be reduced or removed.

In a preferable embodiment, it is preferable that the substance which can specifically interact with sugar chains of the present invention has a specificity to a sugar chain within a certain level between the maximum and minimum. The substance may interact specifically at a level within the range having the maximum value of, for example, normally about ten times that of the minimum value, preferably about five times, more preferably about three times, yet preferably about two times, or about 1.5 times. The above-mentioned range may vary depending upon the measurement methods for the level of interaction. However, in one embodiment, it may be determined by the dissociation energy required when laser irradiation is performed during MALDI-TOF.

In a preferable embodiment, sugar chains which are the target of the substance which can specifically interact with sugar chains of the present invention may include oxidized sugar chains and sugar chains which are not oxidized. Since the substance of the present invention has such a property, not only can it specifically interact with oxidized sugar chains, but it can also interact with any kind of sugar chains equally, and can be advantageously used for purification, concentration, separation, and analysis of sugar chains and sugar chain-containing substances. Thus, sugar chains and sugar chain-containing substance can be concentrated, purified, or separated while the content ratio is maintained as that of the natural state, or the content ratio can be analyzed. In the case where a percentage of oxidized sugar chains and sugar chains in the same group which are not oxidized particularly reflects a specific condition since the natural state can be reflected, such a condition of the subject can be readily determined from a sample taken from the subject. Such an effect cannot be achieved by a substance which interacts only with oxidized sugar chains.

The substance which specifically interacts with sugar chains of the present invention normally includes a functional group which can react with an aldehyde group in a fluid. Herein, the fluid preferably includes substantially no substances that include a keto group (carbonyl group). In particular, fluid selected from the group consisting of an aqueous solution, an organic solvent and the mixture thereof may be advantageous. More preferably, the fluid is an aqueous solution. The sugar chains generally have carbonyl groups such as aldehyde groups in aldehyde type or ketone group in ketose type, and an equilibrium relationship between cyclic hemiacetal type and acyclic aldehyde type is established therein. Thus, by having specificity under such conditions, specific interactions with sugar chains becomes possible. Therefore, as long as it can react with an aldehyde group, the fluid can be anything (organic solvent, gas, and the like).

In a preferred embodiment, the functional group used in the present invention may be selected from the group consisting of hydroxylamino group, N-alkylhydroxylamino group, hydrazide group, thiosemicarbazide group and cysteine residue, but is not limited to these. The linkage between a hydroxylamino group and sugar (oxime bonding) is especially weak to acid. Thus, there is an advantage that sugar chains can easily be cleaved from the sugar chain-trapping carriers.

The substance which specifically interacts with sugar chains of the present invention can be produced by binding a functional group which gives a specific interaction with sugar chains such as a functional group which can react with an aldehyde group in a fluid, to another substance. Such another substance may be a substance which can bind to a support (preferably, phase transition may occur).

Synthesis of such a substance may be performed by, for example, a method in which a reaction intermediate having a functional group which confers a specific interaction with sugar chains, such as functional group which can react with an aldehyde group in a fluid is produced, and then brought into reaction with another substance material which is not related to the specific interaction (for example, 10,12-pentacosadiinoic acid or the like), or, a method in which another substance material which is not related to the specific interaction and the reaction intermediate material (for example, 2,2'-ethylene dioxy)bis(ethylamine)) are mixed, and then another above-mentioned reaction intermediate material (for example, 1-ethyl-3(3'-diethylaminopropyl)carbodiimide hydrochloride) is added to the mixture, but is not limited to these.

Those skilled in the art can understand a functional group having the property that it can react with an aldehyde group and form specific and stable bonding, and can understand a substance having such a functional group. Furthermore, those skilled in the art can produce such a substance having functional group by using techniques well known in the art, alone or in combination.

In another aspect, the present invention provides a lipid including a functional group which can react with an aldehyde group in a fluid. Conventionally, there has been no attempt to produce a substance having properties of lipids, and including a functional group which can react with an aldehyde group in a fluid. This is because a purpose to produce such a substance has not been found yet. In the present invention, an application for a substance which can bind to a support or can be used as a support, and which can specifically bind to sugar chains (particularly, equally, i.e., with specificity of a similar level with any of the sugar chains) has been found for the first time, and thus, production of the lipid as described above has been achieved.

Such a lipid can be represented by a schematic figure (A')-(B'). Herein, (A') denotes a portion having a functional group which can specifically interact with sugar chains (for example, a portion including a functional group which can react with an aldehyde group in a fluid), and (B') denotes a lipid. Specific examples of portion represented by (A') are compounds represented by the above-mentioned formula (I), and specific examples of portions represented by (B') are compounds represented by formula (II). (A')-(B') may be further substituted by substituents as defined above. The number of the substituents varies depending upon the structure of (A')-(B'), and may be the same as the number of existing hydrogens.

(A') may be portions including, for example, a hydroxylamino group, N-alkylhydroxylamino group, hydrazide group, thiosemicarbazide group and a cysteine residue. A portion including a hydroxylamino group may be more preferable. Such a portion may be portions derived from, for example, O-(4-aminomethyl-benzyl)-hydroxylamine; O-(3-aminopropyl)-hydroxylamine; O-[2-(2-aminoethoxy)-ethyl]-hydroxylamine, and the like, but is not limited to these.

(B') may be any type of portion as long as it is derived from a normal lipid. For example, (B') may be penta-10,12-cosadiynoic acid; penta-10,12-cosadiynoic acid {2-[2-(2-aminoethoxy)-ethoxy]-ethyl}-amide palmitic acid; stearic acid; and the like, but is not limited to these.

The lipids of the present invention may be, for example, octadecanoic acid (3-aminooxy-propyl)-amide; octadecanoic acid [2-(2-aminooxy-ethoxy)-ethyl]-amide; octadecanoic acid 4-aminooxymethyl-benzylamide; penta-10,12-cosadiinoic acid (2-(2-[2-(2-aminooxy-acetylamino)-ethoxy]-ethoxy)-ethyl)-amide, and the like, but is not limited to these.

In more preferable embodiments, the substance of the present invention may be described as having the following structure.

(Sugar Chain-Trapping Functional Group)-(Spacer)-(Polymeric Functional Group)

Herein, the sugar chain-trapping functional group may be described as, for example, a functional group which can react with an aldehyde group of sugar chains in a fluid, and has a structure as shown in FIG. 1. R in FIG. 1 refers to a substituent as defined above, but those which do not have a band influence on polymeric reactions and interaction with sugar chains are preferable. More specifically, the substance which can specifically interact with sugar chains of the present invention is a compound which can be represented as follows:

X—Y—Z, Formula (I):

And X in formula is a group represented by the formulae:

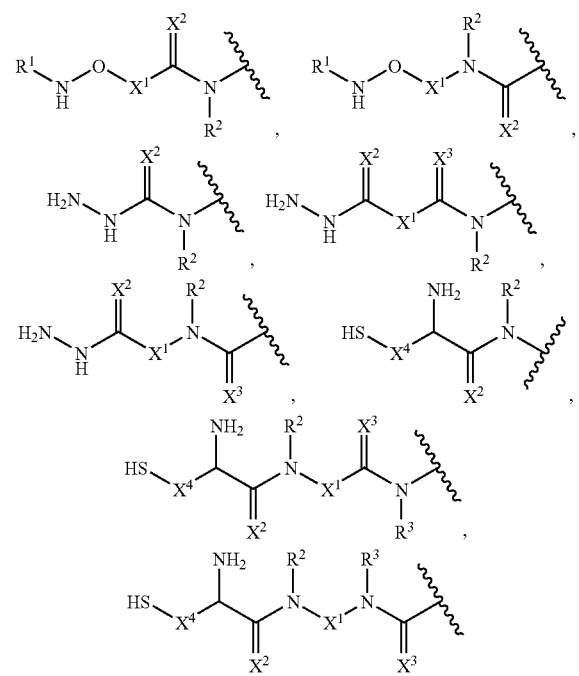

(herein, $X^1$ is alkylene which may be substituted or alkenylene which may be substituted, $X^2$ is an oxygen atom or a sulfur atom, $X^3$ is an oxygen atom or a sulfur atom, $X^4$ is methylene or ethylene, $R^1$ is a hydrogen atom or alkyl, and $R^2$ and $R^3$ are independently a hydrogen atom or alkyl);

Y (the length of Y corresponds to C0-C25) is a single bond; alkylene in which at least one group selected from the group consisting of —O—, —S—, —S—S—, —N($R^a$)—C(=O)—, —C(O)—N($R^b$)—, and phenylene which may be substituted, may intervene or may be substituted; or alkenylene in which at least one group selected from the group consisting of —O—, —S—, —S—S—, —N($R^a$)—C(=O)—, —C(=O)—N($R^b$)—, and phenylene which may be substituted, may intervene or may be substituted (herein, $R^a$ and $R^b$ are independently a hydrogen atom or alkyl);

Z is a group represented by formulae:

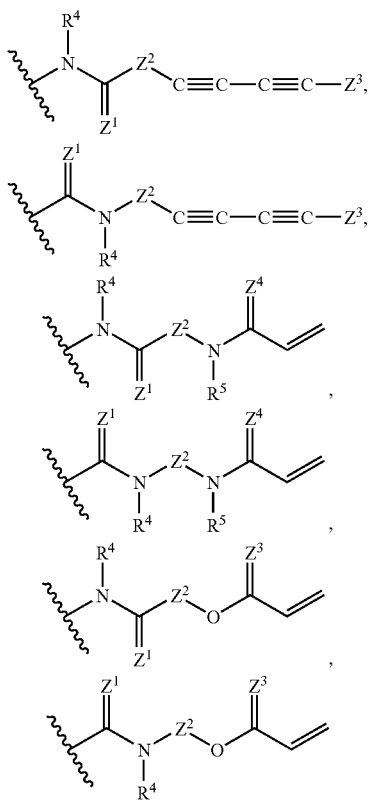

(herein, $Z^1$ is an oxygen atom or sulfur atom, $Z^2$ and $Z^3$ are independently alkylenes in which phenylene may intervene or may be substituted, or alkenylenes in which phenylene may intervene or may be substituted, $Z^4$ is an oxygen atom or a sulfur atom, $R^4$ and $R^5$ are independently a hydrogen atom or alkyl)]. In the compound of formula (I) of the present invention, $X^1$ is preferably C1-C10 alkylene or C2-C10 alkenylene, and the chain length of Y is preferably a chain length corresponding to C1-C25 alkyl. Further preferable examples of Y may be $-(CH_2CH_2-O)_n-CH_2CH_2-$ (herein, n=1-8 is preferable, and particularly n=1-6 is preferable). It is preferable that $Z^2$ and $Z^3$ are independently C1-C10 alkylene or C2-C10 alkenylene. Further, a specific example of phenylene which may be substituted may be as follows:

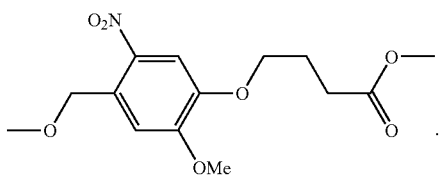

In a preferred embodiment, a polymer obtained by polymerizing the compounds of formula (I) is used. This results in the effect that, when various films are formed of the substance which can specifically interact with sugar chains of the present invention, the strength and stability of the film themselves increase, and can be fixed to a support such as a substrate. For fixing the films to the support, a method of polymerizing monolayers obtained by physically adsorbing z sites of the compounds represented by formula (I) to the support is preferable. In this way, the support to which the film is fixed can be used as the sugar chain-trapping carrier of the present invention, as it is. The above polymerization may be heat polymerization, or may be photopolymerization. However, in view of the advantages that radical polymerization between diacetylene groups or vinyl groups in sites Z can be proceeded smoothly, and an operation for polymerization is relatively convenient, photopolymerization by UV-irradiation at a wavelength around 254 nm which is the absorption wavelength of diacetylene groups or vinyl groups, is preferably employed. Further, a substance in which "X" in formula (I) and the support are directly bound to each other, and a substance in which "X—Y" and "support" are directly bound, are employed. Substituents of "alkylene which may be substituted" and "alkenylene which may be substituted" in $X^1$ are preferably not substituted. Substituents of "alkylene which may be substituted" and "alkenylene which may be substituted" in Y are preferably not substituted. Substituents of "alkylene which may be substituted" and "alkenylene which may be substituted" in $Z^2$ and $Z^3$ are preferably not substituted.

In another preferable embodiment, the substance which can specifically interact with sugar chains of the present invention is a copolymer obtained by polymerizing a compound represented by formula (I): X—Y—Z (I)

[herein, X is a group represented by the formulae:

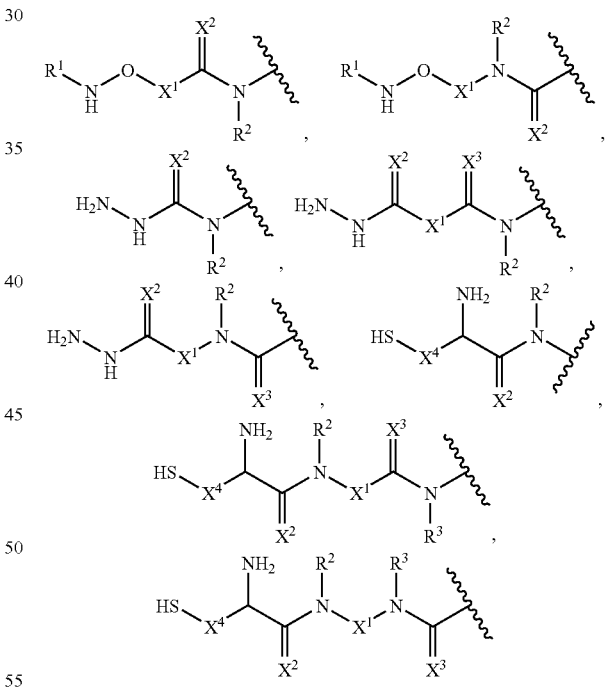

(herein, $X^1$ is alkylene which may be substituted or an alkenylene which may be substituted, $X^2$ is an oxygen atom or a sulfur atom, $X^3$ is an oxygen atom or a sulfur atom, $X^4$ is methylene or ethylene, $R^1$ is a hydrogen atom or an alkyl, and $R^2$ and $R^3$ are independently a hydrogen atom or an alkyl);

Y (the length of Y corresponds to C0-C25) is a single bond; alkylene in which at least one group is selected from the group consisting $-O-$, $-S-$, $-S-S-$, $-N(R^a)-C(O)-$, $-C(=O)-N(R^b)-$, and phenylene which may be substituted, may intervene or may be substituted, or alkenylene in which at least one group selected from the group consisting —O—, —S—, —S—S—, —N(R$^a$)—C(=O)—, —C(O)—N(R$^b$)—, and phenylene which may be substituted, may intervene or may be substituted (herein, R$^a$ and R$^b$ are independently a hydrogen atom or an alkyl);

Z is a group represented by the formulae:

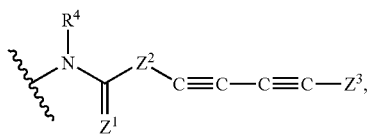

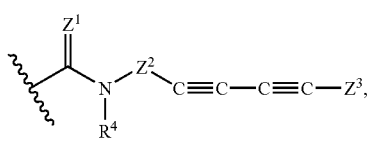

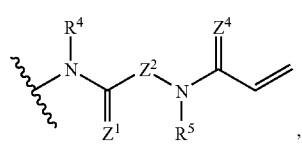

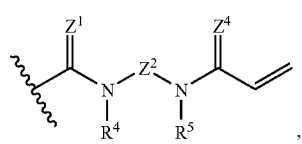

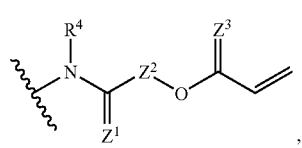

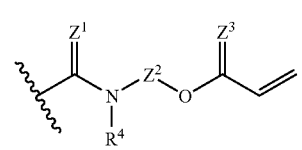

(herein, $Z^1$ is an oxygen atom or sulfur atom, $Z^2$ and $Z^3$ are independently alkylenes in which phenylene may intervene or may be substituted, or alkenylenes in which phenylene may intervene or may be substituted, $Z^4$ is an oxygen atom or a sulfur atom, $R^4$ and $R^5$ are independently a hydrogen atom or alkyl)]; and a compound represented by formula (II): $A^1$-$A^2$(II)

[herein, $A^1$ is H(OCH$_2$CH$_2$)$_n$O— (n is an integer from 1 to 5) or a group represented by the formula:

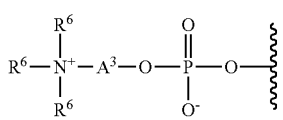

(herein, $A^3$ is alkylene, and $R^6$ is alkyl); and $A^2$ is a group represented by the formulae:

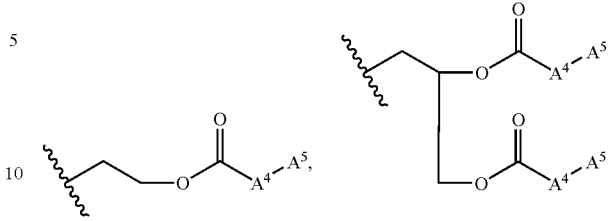

(herein, $A^4$ is alkylene, and $A^5$ is represented by the formulae:

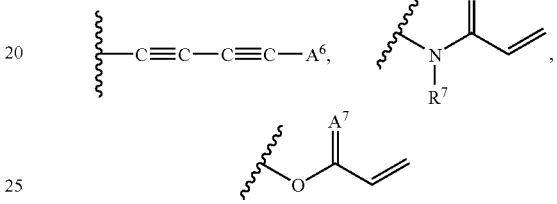

($A^6$ is an alkylene, $A^7$ is an oxygen atom or a sulfur atom, and $R^7$ is a hydrogen atom or alkyl)]. In the copolymer of the compounds of formulae (I) and (II) of the present invention, $X^1$ is preferably C1-C10 alkylene or C2-C10 alkenylene, and the chain length of Y is preferably a chain length corresponding to C1-C25 alkyl. Further preferable examples of Y may be —(CH$_2$CH$_2$—O)$_n$—CH$_2$CH$_2$— (herein, n=1-8 is preferable, and particularly n=1-6 is preferable). It is preferable that $Z^2$ and $Z^3$ are independently C1-C10 alkylene or C2-C10 alkenylene. $A^3$ is preferably C1-C5 alkylene, and in particular, C2 alkylene. It is preferable that $A^4$ and $A^6$ are independently C1-C10 alkylene. Further, a specific example of a phenylene which may be substituted may be as follows:

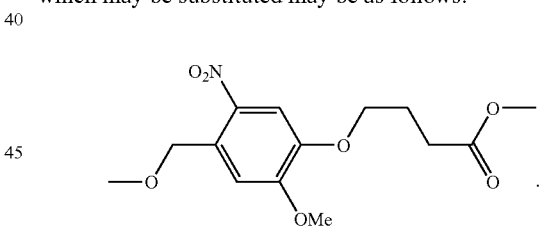

The polymerization may be heat polymerization or may be photopolymerization. However, as described above, photopolymerization by UV-irradiation at a wavelength around 254 nm, which is the absorption wavelength of diacetylene groups or vinyl groups is preferable.

When various films are formed of the substance which can specifically interact with sugar chains of the present invention, regardless of the form of the films (for example, monolayers, LB films, cast films, liposomes and the like), film stability can be enhanced by combining the compound represented by formula (II) which is a matrix molecule and the compound represented by formula (I). Advantageously, if the film is stable, polymerization of the film proceeds smoothly regardless of its forms, and the film becomes easy to transfer (or fix) monolayers, and the like. In view of stabilizing the films, the molar fraction of the compound of formula (II) with respect to the total mixture of the compound of formula (I) and the compound of formula (II) is 0.1-0.9. For fixing the films to the support, a method of polymerizing monolayers obtained by physically adsorbing z sites of the compound represented by formula (I) and $A^2$ site of the compound represented by formula (II) to the support is preferable. In this way, the support to which the film is fixed can be used as the sugar chain-trapping carrier of the present invention, as it is.

In another aspect, the present invention provides a sugar chain-trapping carrier including a substance which can specifically interact with sugar chains. The sugar chain-trapping carrier may further include a support. Such a support can be used for, for example, separating, concentrating, purifying, or analyzing the sugar chains or sugar chain-containing substances in a sample. Since the sugar chain-trapping carrier of the present invention interact with any sugar chains with no discrimination, sugar chains and sugar chain-containing substances can be concentrated, purified, or separated while maintaining the naturally exisiting content ratio, or the content ratio can be analyzed. Since the state of the sugar chains or sugar chain-containing substances substantially reflects the natural state, a condition of the subject which can be determined based on the sugar chains can be readily determined from a sample taken from the subject.

The sugar chain-trapping carrier of the present invention can be produced by interacting (preferably binding) the substance which can specifically interact with sugar chains and the support using techniques well known in the art. For example, when a lipid film is used as the support, as the substance which can specifically interact with sugar chains, by including photopolymerizable portions in a lipid having a functional group which can react with an aldehyde group in a fluid and a lipid which does not include such a functional group, and photopolymerizing them, a lipid can be made to function as a film support.

Therefore, in a preferable embodiment, the support used in the sugar chain-trapping carrier of the present invention may be a cross-linked polymer or lipid film. By using a cross-linked polymer or lipid film, two-dimensional extension becomes possible. Thus, it can be advantageously used in an embodiment which requires planarity, such as sugar chain chips.

In another preferable embodiment, the support used in the sugar chain-trapping carrier of the present invention includes a photopolymerizable lipid derivative. Since it includes the photopolymerizable lipid derivative, it is easily formed into a desired shape, such as a film, by irradiating with light and polymerizing. Such photopolymerizable lipid derivatives may be, for example, a compound having a diacetylene represented by formula (III) —C≡C—C≡C—, and photopolymerizable monomers other than diacetylene such as acrylate, epoxide, vinylether, and the like, but is not limited to these. As long as it has such a structure, the length of the lipid is not particularly limited. However, the length of, for example, C=20-30 may be normally employed. Thus, in the preferred embodiment, the photopolymerizable lipid derivative of the sugar chain-trapping carrier of the present invention is polymerized by ultraviolet ray.

The methods for polymerizing a mixture of the compound represented by formula (I) and the compound represented by formula (II) in the present invention may be categorized into the following three groups depending on the shape of the film formed of monomer components before polymerization.

i) Polymerization of Water Dispersion (or Liposome)

First, a mixture of the compound represented by formula (I) and the compound represented by formula (II) is dissolved in an appropriate organic solvent (for example, chloroform). The organic solvent may be either a single solvent or a mixture of solvents as long as it is an organic solvent which can dissolve the above-mentioned mixture completely and which is volatile, and is not particularly limited. The solvent is completely removed under depressurization by evaporation, ultrapure water is added to the residue, and then, for example, ultrasonic dispersion is performed for 10-20 minutes, Such ultrasonic dispersion forms water dispersion of the above-mentioned mixture (typically, as a liposome such as a bilayer membrane, but is not limited to this) in an aqueous solution. Then, it is preferable to raise the temperature of the aqueous solution to a temperature higher than the crystal-liquid crystal phase transition temperature (Tc) by a few degrees Celsius, and to leave the aqueous solution for a few minutes for aging the water dispersion. Such aging has the effect of enhancing stability and the order of the film formed in water by ultrasonic dispersion. Such effect can be further enhanced by repeating aging. Thereafter, the aqueous solution is rapidly cooled to a temperature sufficiently lower than the crystal-liquid crystal phase transition temperature (Tc), i.e., the temperature where the film becomes crystalline condition, and air is removed from the aqueous solution using an aspirator or the like. Removal of air is effective since it removes dissolved oxygen, which is a free radical, and thus may inhbit polymerization. The aqueous solution is kept at a temperature well below Tc (i.e., the temperature at which the film can maintain a crystalline condition), and light is irradiated using an ultraviolet ray lamp (for example, a low-pressure mercury lamp and the like) while an inert gas (for example, argon gas or nitrogen gas) is bubbled through the solution. Tracking of the polymerization reaction process and confirmation of reaction saturation are usually performed spectroscopically using the UV-visible absorption spectrum. Purification of the polymerization film is performed using a filter membrane of few hundred microns. The shape of the polymerization film can be confirmed using an electron microscope or the like.

ii) Polymerization of Cast Film

First, a mixture of the compound represented by formula (I) and the compound represented by formula (II) is dissolved in a similar, appropriate organic solvent (for example, chloroform). The solution is poured onto a substrate, and dried well. Then, aging is performed in water by a method similar to that described in section i), and the film is rapidly cooled to a temperature to crystallize. Photopolymerization of the cast film may be performed while it is immersed into water kept to a temperature well below Tc, or may be performed in air kept to a temperature well below Tc by an incubator or the like. Tracking of the polymerization reaction process and confirmation of reaction saturation are performed as described in section i).

iii) Polymerization of Monolayer or LB Film

First, a monolayer is prepared as follows. A mixture of the compound represented by formula (I) and the compound represented by formula (II) is completely dissolved in an appropriate organic solvent (an organic solvent which is water-soluble and volatile, for example, chloroform) at an appropriate concentration (for example, 10 mg/10 ml). The solution is spread onto the surface of water in a thermostatted trough (for example, a Langmuir trough, but is not limited to this) to prepare a monolayer of the mixture of (I) and (II). A polymer of the LB film of (I) and (II) may be obtained by either of a method in which the monolayer is exposed to UV-irradiation, and then brought into horizontal contact with to the support such as a solid substrate and physically adsorbed, or a method in which the monolayer is brought into horizontal contact with the support and physically adsorbed, and then exposed to UV-irradiation.

Preferably, the support used in the sugar chain-trapping carrier of the present invention may be insoluble in organic solvents.

In another embodiment, the support used in the sugar chain-trapping carrier of the present invention may be a self-closed lipid film. Alternatively, the support may be two dimensionally extended. When the support is a self-closed lipid film, it can be advantageously used for separation and purification of the sugar chains using a filter and the like. When a two-dimensionally extended support is used, it can be advantageously used for sugar chain replicas and sugar chain chips. The sugar chain-trapping carrier of the present invention may have similar properties to normal lipids. Thus, those skilled in the art can apply production techniques of, for example, liposomes, microspheres and the like to produce the sugar chain-trapping carrier of the present invention having the form of self-closed type. Two-dimensionally extension can also be performed by applying methods well known in the art.

Preferably, it may be advantageous that the two-dimensionally extended support used in the present invention is a cast film or monolayer. Such a film is useful in techniques which requires a reaction on a plate such as mass spectroscopy, a method for producing a sugar chain replica, and in the production of a sugar chain chip. In such listed techniques, it is advantageous or necessary to trap sugar chains on a support having a film form. The techniques for producing a cast film and monolayer are well-known in the art, and may be, for example, LB monolayer methods, methods for casting in a mold and subjecting to natural evaporation, and a method in which a lipid material is floated on the surface of water to mold a support, but is not limited to these. Specifically, when such a method is used in, for example, MALDI-TOF MS, sugar chains or sugar chain-containing substance or a sample including thereof is added to a solution of sugar chain-trapping carrier (preferably, buffer such as acetic acid buffer) as necessary, then alcohol such as methanol is added, and poured onto a plate of MALDI-TOF MS, and subjected to natural evaporation for interaction.

Figure 10:
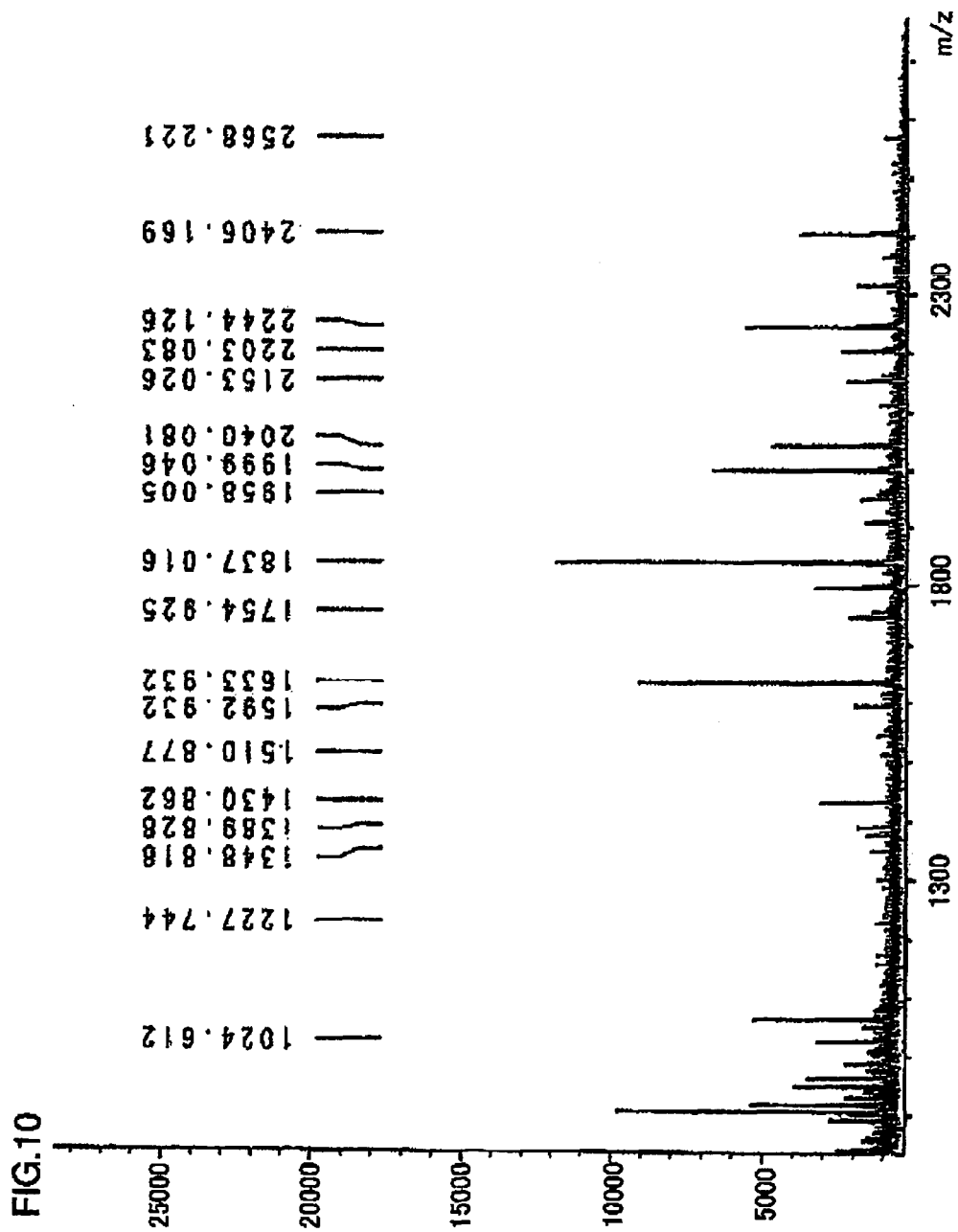
FIG. 10 is a diagram showing MALDI-TOF spectrum after a sample of FIG. 9 is treated with Girard T reagent. m/z of main peaks of FIG. 10 are 1024.612, 1227.744, 1348.818, 1389.828, 1430.862, 1510.877, 1592.932, 1633.932, 1754.925, 1837.016, 1958.005, 1999.046, 2040.081, 2153.026, 2203.083, 2244.126, 2406.169 and 2568.221 in an ascending order.

In another aspect, a method for synthesizing a substance which can specifically interact with sugar chains is provided. This method includes the steps of: A) providing a functional group which can react with an aldehyde group in a fluid; and B) binding the functional group to a desired substance. Since the substance which can specifically interact with sugar chains itself is a novel substance which does not conventionally exist, such a method achieves a significant effect that it provides techniques for producing such a novel substance. Particularly, when the substance which can specifically interact with sugar chains has any of the preferable embodiments described above, this method can be modified and used by those skilled in the art in accordance with the properties of the preferred embodiments. For example, when the functional group which may react with aldehyde in a fluid is selected from the group consisting of a hydroxylamino group, N-alkylhydroxylamino group, hydrazide group, thiosemicarbazide group and a cysteine residue, the method includes the step of providing a substance having such a functional group (for example, see above (A')), or providing a substance in which such a functional group is protected, and the step of binding the substance to another substance (for example, the substance which may interact with a support or the substance which can be used as a support such as lipid described in above (B')). In a preferred embodiment, binding to a desired substance is achieved by ester bonding or amide bonding. Thus, it is preferable that either or both of the substance provided in A) and the desired substance provided in B) has a hydroxyl group or amino group, or carboxyl group (or vice versa). An example of such a synthesis method may be, for example, the scheme as shown in FIG. 10, but is not limited to that.

In another aspect, the present invention provides a method for separating, concentrating, or purifying the sugar chains or sugar chain-containing substance in a sample. The method includes: a) contacting a sugar chain-trapping carrier comprising a substance which can specifically interact with sugar chains with the sample in a fluid phase under conditions that the sugar chain-trapping carrier can react with the sugar chains or sugar chain-containing substance; b) isolating a composite of the sugar chain-trapping carrier and the sugar chains or sugar chain-containing substance from the fluid phase; and c) exposing the composite to conditions under which the interaction between the sugar chain-trapping carrier and the sugar chains or sugar chain-containing substance is at least partially eliminated. The sugar chain-trapping carrier may further include a support. In this method, the sugar chain-trapping carrier including the substance which can specifically interact with sugar chains and support of the present invention is used, the substance interacts with any sugar chains with no discrimination. Thus, the effect that the sugar chains and sugar chain-containing substance can be concentrated, purified, or separated with a content ratio in the natural state being maintained, which has been impossible in the conventional art, can achieved. Alternatively, the method of the present invention can provide a sample for analyzing the content ratio. Since the natural state can be reflected, the state of the subject which can be determined based on the sugar chains can be readily determined from a sample taken from the subject. Alternatively, since the sugar chains which reflect the state in nature are concentrated, it becomes possible to provide a sugar chain composition which can be advantageously used in fields where biomolecules are involved, such as medicine, agriculture, healthcare, food, cosmetics and the like. Such a sugar chain composition can be distinguished from conventional biodegradable products on the point that the sugar chain composition has a composition ratio substantially the same as that in the original sugar chain binding state, and has a significant effect in various aspects in which it is necessary to reflect original sugar chains.

The step a) of contacting a sugar chain-trapping carrier comprising a substance which can specifically interact with sugar chains with the sample in a fluid phase under conditions that the sugar chain-trapping carrier can react with the sugar chains or sugar chain-containing substance in the present invention may be achieved by mixing the sugar chain-trapping carrier and the sample, and exposing the mixture to the conditions that the sugar chain-trapping carrier can react with the sugar chains or sugar chain-containing substance. The sugar chain-trapping carrier may further include a support. The sample can be prepared from a desired living organism or synthetic material using techniques well known in the art. When it is desired to asess a disease, disorder or condition, it can be prepared by obtaining a sample (for example, blood, urine, or the like) from the living body which is an object of asessment. Such a sample may be used as it is, or may be used after being subjected to a reaction for liberating the sugar chains from the sugar chain-containing substance. The conditions in which the sugar chain-trapping carrier can react with the sugar chains or sugar chain-containing substance is as defined in the present specification, and can be adjusted by those skilled in the art as appropriate by taking the properties, amounts and the like of the substance to be used into consideration and using techniques well known in the art. Herein, preferably, it may be advantageous that the fluid is selected from a group consisting of an aqueous solution, organic solvent and the mixture thereof in the step b) isolating a composite of the sugar chain-trapping carrier and the sugar chains or sugar chain-containing substance from the fluid phase in the present invention. More preferably, the fluid used herein is an aqueous solution. Particularly, it is preferable that the fluid used herein is a buffer which does not destroy the composite (for example, buffer having pH value around neutral). In step b), preferably, centrifugal separation can be performed.

The step c) exposing the composite to the conditions under which the interaction between the sugar chain-trapping carrier and the sugar chains or sugar chain-containing substance is at least partially eliminated may be performed by those skilled in the art as appropriate by taking the properties of the formed composite (particularly, forms of interaction) into an account, and using techniques well known in the art. Such conditions may be, for example, the presence of a strong acid, and the like, but is not limited to these. However, in such conditions, it is preferable that the sugar chains themselves are not destroyed. When it is desirable that the sugar chains be maintained in their natural state, such a condition may be particularly preferable. However, conditions such that the sugar chains may be destroyed can also be used, depending upon the purpose after purification, separation or concentration. Preferably, the sugar chains may be eliminated entirely.

In the above method, steps a), b) and c) may be preferably performed in the same container, but in another embodiment, it may be preferable to perform the steps in different containers. By performing the steps in the same container, purification, concentration, and separation of the sugar chains and sugar chain-containing substance can be performed in a streamlined manner, and automation becomes possible. However, when the reaction conditions, fluids and the like to be used are different, it may be advantageous to perform the steps in different containers.

In the method for separating, concentrating, or purifying the sugar chains or sugar chain-containing substance in the sample of the present invention, it may be preferable to have a step of liberating an aldehyde group in the sample before the step a). This is because, for example, when an aldehyde group of the sugar chains is protected, the substance which can specifically interact with sugar chains of the present invention can advantageously interact. Such a step of liberating an aldehyde group preferably includes a proton-donating reaction by an enzyme treatment and/or a chemical method. The enzyme treatment may be, for example, a treatment by glycosidase, and the treatment by a chemical method may be hydrazinolysis. In the method of the present invention, the enzyme treatment and the chemical method can be used separately or in combination. One type of enzyme or a plurality of types of enzymes may be used. The enzymes may be anything, for example, glucosidase derived from plants, yeasts, molds, and the like. The enzymes may preferably be N-glucosidase derived from *Flavobacterium*, but not limited to this. Hydrazinolysis is preferable. Only N-type sugar chains are separated when the enzymes are used, but in hydrazinolysis, both N-type sugar chains and O-type sugar chains may be separated and analyzed. Hydrazinolysis may be in a gas phase, or a liquid phase. Hydrazinolysis in a liquid phase is easy to be operated, but is not good for treating a number of samples, and there is a problem in safety because there is possibility of contacting a reagent. Another drawback is that it takes time to remove hydrazine. Necessary equipment may be a block heater, screw cap vial, vacuum pump and the like. When the sugar chain-containing substance is a glycopeptide, the peptide itself is decomposed into amino acid hydrazide. Gas phase hydrazinolysis is easy to be use, and can process a number of samples at the same time. Necessary equipment may be a gas phase hydrazinolysis apparatus, vacuum pump and the like. Gas phase hydrazinolysis is suitable for high throughput process such as searching for a disease marker from a lot of specimens, proteome analysis (modification after translation), and the like. Thus, in the present invention, it is possible to use such separation techniques separately, or in combination.

It may be preferable that the method for separating, concentrating, or purifying the sugar chains or sugar chain-containing substance in the sample of the present invention further includes the step of d) subjecting the sample to the conditions that the sugar chain-containing substance is separated into sugar chains and the rest. By isolating the sugar chain portions of sugar chain-containing substance included in the sample, it becomes advantageous because analysis of sugar chains becomes easy and the sugar chains themselves can be used for other purposes.

The conditions that the sugar chain-containing substance is separated into sugar chains and the rest are as defined in the present specification. Such conditions may be using, for example, physical means (for example, laser and the like), chemical means (acidic condition) or biochemical means (for example, enzymes such as glycosidase), but are not limited to these. Preferably, enzyme treatments by hydrazinolysis or glycosidase may be used, but are not limited to these.

In another aspect, the present invention provides an apparatus for separating, concentrating, or purifying sugar chains or a sugar chain-containing substances in a sample. The apparatus comprises: a) a sample introduction section; b) a container having a space which can house a fluid phase; and c) a sugar chain-trapping carrier comprising a substance which can specifically interact with sugar chains, the container being in fluid communication with the sample introduction section. The sugar chain-trapping carrier may further include a support. This apparatus utilizes a sugar chain-trapping carrier including a substance which can specifically interact with sugar chains of the present invention onto separate, concentrate, or purify the sugar chains or sugar chain-containing substances in the sample. Thus, for example, due to the property that the suger chain-trapping carrier interacts with any sugar chains with no discrimination, the apparatus can concentrate, purify, or separate the sugar chains and sugar chain-containing substances while maintaining the content ratio in the natural state. Further, a sample which allows analysis of the content ratio reflecting the state in nature can be provided. By using the apparatus of the present invention, the natural state can be reflected. Thus, the condition of the subject which can be determined by sugar chains can be readily determined by a sample taken out of the subject. The apparatus having such advantages can be used to provide sugar chain composition which can be effectively used in fields where biomolecules are involved, such as medicines, agriculture, healthcare, food, cosmetics and the like. The apparatus of the present invention provides advantages which are not observed in conventional apparatuses in that it can provide a novel sugar chain composition, which is the sugar chain composition substantially the same as the original sugar chain binding state, but the substances other than the sugar chains are reduced.

The a) sample introduction section used in the apparatus of the present invention may have any form as long as it is a portion which allows a sample to be introduced. Since separation, concentration or purification is intended, it is preferable that the sample introduction section is not contaminated. However, as long as it is not contaminated with sugar chains, or sugar chain-containing substances, it may be contaminated with other substances (simple proteins or the like).

The b) container having a space which can house a fluid phase used in the apparatus of the present invention may be any kind of container as long as it does not completely remove interaction between the sugar chains and the sugar chain-trapping carrier of the present invention. Preferably, the container may be the one which does not affect such interaction. More preferably, it may be advantageous that the sugar chain-trapping carrier is bound. It is preferable that such a binding to carrier may be performed via the support in the carrier. Further, in the sugar chain-trapping carrier, it is preferable that substances which can specifically interact with sugar chains and the support are bound to each other (preferably, by covalent bonds). Such a container can be readily fabricated by those skilled in the art taking the expected reactions and objective of use of the apparatus into consideration and using techniques well known in the art.

The c) sugar chain-trapping carrier including a substance which can specifically interact with sugar chains used in the apparatus of the present invention may be any of the sugar chain-trapping carriers of the present invention. The sugar chain-trapping carrier may further include a support. Thus, such a sugar chain-trapping carrier may be any kind of carrier as long as it is related to embodiments described in the present specification, and those skilled in the art can modify the carrier as necessary in order to apply it to the apparatus. Of course, such a modification is also within the scope of the present invention. An example of such modification may be modifying the sugar chain-trapping carrier of the present invention so as to be suitable to be fixed to the container, but is not limited to this. Such modification may be, for example, further adding a reactive functional group, locating a functional group which reacts with such a reactive functional group on a container, and bringing them into reaction, but is not limited to these.

In another aspect, the present invention provides a system for separating, concentrating, or purifying sugar chains or a sugar chain-containing substances in a sample. The system comprises: A) an apparatus comprising: a) a sample introduction section; b) a container having a space which can house a fluid phase; and c) a sugar chain-trapping carrier comprising a substance which can specifically interact with sugar chains, the container being in fluid communication with the sample introduction section; B) means for isolating a composite of the sugar chain-trapping carrier and the sugar chains in the fluid phase; and C) means for exposing the composite to the conditions that the interaction between the sugar chain-trapping carrier and the sugar chains is at least partially eliminated. The sugar chain-trapping carrier may further include a support. By providing such a system, the present invention can be used for providing a sugar chain composition which can be advantageously used in fields where biomolecules are involved, such as medicines, agriculture, healthcare, food, cosmetics and the like.

The A) apparatus which is used in the system of the present invention may be the above-described apparatus of the present invention. However, the apparatus is preferably modified to a shape so as to house or couple B) means for isolating a composite of the sugar chain-trapping carrier and the sugar chains in the fluid phase; and C) means for exposing the composite to the conditions such that the interaction between the sugar chain-trapping carrier and the sugar chains is at least partially eliminated, or to be provided with those means.

In the preferred embodiment, the above means C) is means for liberating aldehyde. Preferably, this means C) may be enzymes which liberate aldehyde (enzymes such as glycosidase) or a chemical substance (for example, a reagent used for hydrazone decomposition).

The B) means for isolating a composite of the sugar chain-trapping carrier and the sugar chains from the fluid phase used in the system of the present invention may be any kind of means as long as it can isolate the composite. Those skilled in the art can choose appropriate composite isolating means by taking various parameters such as the properties of the composite, structure of the apparatus and the like, and techniques well known in the art into consideration. Preferable examples of such means are centrifugal separator, filter, and chromatography apparatus, but are not limited to these. More preferably, a filter may be used. Such a filter may preferably have structure which leaves the composite and passes the components which do not become a composite. As a filter having such a structure, for example, the particle size of the composite and the particle size of the components which are expected to exist are calculated, and a filter having a pore size which is intermediate between the particle sizes can be used.

The C) means for exposing the composite to the conditions such that the interaction between the sugar chain-trapping carrier and the sugar chains is at least partially eliminated used in the system of the present invention may be any kind of means as long as it can provide such conditions. If such conditions can be provided by exchanging solutions, a container which houses the solutions may be appropriate. If such conditions can be fulfilled by adding new components (solid or liquid), the means may be a container which houses the additional solutions. Such means or such a container can be readily produced and handled by those skilled in the art by taking the conditions to be provided into consideration and using techniques well known in the art.

In a preferred embodiment, the system of the present invention further includes D) subjecting the sample to the conditions that the sugar chain-containing substance is separated into sugar chains and the rest. Such means may be any kind of means as long as it can present conditions that such separation is achieved. If such conditions can be provided by exchanging solutions, a container which houses the solutions may be appropriate. If such conditions can be fulfilled by adding new components (solid or liquid), the means may be a container which houses the additional solutions. Such means or such a container can be readily produced and handled by those skilled in the art by taking the conditions to be provided into consideration and using techniques well known in the art.

In another aspect, the present invention provides a method for manufacturing an apparatus for separating, concentrating, or purifying sugar chains or a sugar chain-containing substance in a sample. The method comprises the steps of: a) providing a substance and a support which can specifically interact with sugar chains; b) causing the substance which can specifically interact with sugar chains to interact with the support to produce a sugar chain-trapping carrier; and c) fixing the sugar chain-trapping carrier to a container. This method uses the sugar chain-trapping carrier of the present invention. Since the sugar chain-trapping carrier interacts with any chains with no discrimination, an apparatus which can concentrate, purify, and separate the sugar chains and sugar chain-containing substances while the content ratio is maintained in the natural state can be produced by the above method.

In the step of a) providing a substance and a support which can specifically interact with sugar chains performed in the method of the present invention, the substances which can specifically interact with sugar chains described in the present specification may be used. The support may also be the ones described in the present specification. The preferred embodiment as the substance which can specifically interact with sugar chains is also described in the present specification, and the preferred embodiment can also be used in the above method. The preferred embodiment as a support is also described in the present specification, and can also be used in the above method.

The step of b) causing the substance which can specifically interact with sugar chains to interact with the support to produce a sugar chain-trapping carrier, which is performed in the method of the present invention, can also be carried out by combining techniques well known in the art. Such production of sugar chain-trapping carriers is achieved by exposing both the substances which can specifically interact with sugar chains and the support to conditions sufficient for interaction (for example, buffer, polarity of solvent, temperature, pH, salt concentration, pressure and the like). Setting of parameters required for setting such conditions is within the technical scope of those skilled in the art. Those skilled in the art can perform interaction reactions by setting such conditions using techniques well known in the art taking various parameters related to interaction such as the type of interaction, the type of sugar chains, substances which can specifically interact with sugar chains (for example, the substance having a functional group which can react with an aldehyde group in a fluid), and the type of the support (lipid) into consideration.

The step of c) fixing the sugar chain-trapping carrier to a container, which is performed in the method of the present invention, can be also carried out by combining techniques well known in the art. Such fixing is achieved by exposing both the sugar chain-trapping carrier and the container to conditions sufficient for interaction (for example, buffer, polarity of solvent, temperature, pH, salt concentration, pressure and the like). Setting of parameters required for setting such conditions is within the technical scope of those skilled in the art. Those skilled in the art can perform fixing by setting such conditions using techniques well known in the art taking various parameters related to interaction such as the type of interaction, the type of sugar chain-trapping carrier, and the material of the container into consideration.

In another aspect, the present invention provides a method for analyzing sugar chains or a sugar chain-containing substance in a sample. The method comprises the steps of: a) contacting a sugar chain-trapping carrier comprising a substance which can specifically interact with sugar chains with the sample in a fluid phase under the conditions that the sugar chain-trapping carrier can react with the sugar chains; b) exposing the sugar chain-trapping carrier and the sample to the conditions of desired stringency; and c) identifying a substance which interacted with the sugar chain-trapping carrier. The sugar chain-trapping carrier may further include a support. In this method, the sugar chain-trapping carrier of the present invention is used. Due to a property that the sugar chain-trapping carrier interacts with any sugar chains with no discrimination, the content ratio of the sugar chains and sugar chain-containing substances can be analyzed while the content ratio is maintained in the natural state. As such, the natural state can be reflected. Thus, for example, the condition of the subject, which can be determined by sugar chains, can be readily determined by a sample taken out of the subject. Alternatively, the sugar chains which reflect the state in nature are concentrated. Thus, it is possible to provide analysis values which can be effectively used in fields where biomolecules are involved, such as medicines, agriculture, healthcare, food, cosmetics and the like. Such analysis values have significant effects in various aspects which require the faithful reflection of the types of original sugar chains since the sugar chain composition of the sample which forms a basis of data has substantially same composition ratio as the original sugar chain binding state.

In a preferred embodiment, the object of analysis by the method of the present invention may be a sample derived from a subject which includes or is expected to include etiology. Such a sample may be directly used, or a treatment which does not affect sugar chain analysts may be performed. The sample analyzed by the method of the present invention may derived from animals, plants, bacteria, virus, fungi, or the like, and preferably derived from human or living organisms related to human life (for example, pathogenic agent, domestic animal, agricultural crops and the like).

In a preferred embodiment, in an analysis method of the present invention, the steps a)-c) are performed on a chip supporting the sugar chain-trapping carrier. The chip is as described in a different portion of the present specification, and those skilled in the art can appropriately construct a structure suitable for performing the above-mentioned steps in accordance with the disclosure of the present specification by combining techniques well known in the art.

The sugar chain-trapping carrier used in the analysis method of the present invention is preferably arranged in an array on the chip. The analysis apparatus (device) arranged in an array shape may also be referred to as the sugar chain array in the present specification.

In another embodiment, the identifying step c) in the analysis method of the present invention may include a physical method (mass spectrum analysis, NMR, X-ray analysis, elemental analysis and the like), chemical method (observation of chemical specific reaction), biochemical method (determining substrate specificity of enzymes and the like), or biological method (reaction of living organisms (for example, microorganism such as bacteria)). In a preferred embodiment, the identifying step c) in the analysis method of the present invention includes mass spectrum analysis. Such mass spectrum analysis may be, for example, MALDI-TOF MS, but is not limited to this. Alternatively, NMR may be used.

In another aspect, the present invention provides a method for producing a sugar chain replica of a sample comprising or expected to comprise sugar chains. The method comprises the steps of: a) locating a substance which can specifically interact with sugar chains on a surface of a two-dimensionally extended support, and contacting a surface on which the substance is not being located with a solid foil; and b) contacting the sample comprising or expected to comprise sugar chains with the solid foil. Since such a sugar chain replica reflects the state, content ratio, places and the like when the sugar chains exist in nature, an advantage that the state of the subject from which the sugar chain replica derived can be inspected faithfully and conveniently by inspecting the sugar chain replica can be provided. Conventionally, even the idea of such a sugar chain replica has not existed. Thus, the usefulness as means for direct diagnosis is enormous. Such a sugar chain replica can be produced by adsorbing a surface (preferably a hydrophobic surface) of a two-dimensionally extended support (for example, lipid film) in the sugar chain-trapping carrier of the present invention to a solid foil (preferably, transparent one) such as glass, and adhering to a biological sample to transfer a two-dimensional image of the sugar chains derived from the biological sample plane on the solid foil. Therefore, the support in which hydrophobic interaction readily occurs may be preferably used as the support herein.

In a preferred embodiment, it may be advantageous to include the step of marking a desired character of the sample in a solid foil when the sugar chain replica is produced. Herein, the desired characteristic may be the one which can be observed with naked eyes such as a lesion, or may be one which can be observed by other means. By marking the desired character such as a lesion, and correlating the mark and the identified sugar chains, the relationships between the sugar chains and certain characteristics which have been conventionally unknown can be studied. Alternatively, if the relationship is known, by only identifying the sugar chains, the state of the desired character such as a lesion can be inspected in a qualitative or quantitative manner.

In another aspect, the present invention provides a sugar chain replica of a sample comprising or expected to comprise sugar chains. The sugar chain replica comprises: a) solid foil; b) a two-dimensionally extended support on which a substance which can specifically interact with sugar chains is located, the support for interacting with the solid foil; and c) a component derived from the sample comprising or expected to comprise sugar chains, the component being trapped by the substance which can specifically interact with sugar chains. Since such a sugar chain replica reflects the state, content ratio, places and the like of when the sugar chains exist in nature, an advantage that the state of the subject from which the sugar chain replica was derived can be inspected faithfully and conveniently by inspecting the sugar chain replica can be provided. Such a sugar chain replica can be produced by adsorbing a surface (preferably a hydrophobic surface) of a two-dimensionally extended support (for example, a lipid film) in the sugar chain-trapping carrier of the present invention to a solid foil (preferably, a transparent one) such as glass, and adhering to a biological sample to transfer a two-dimensional image of the sugar chains derived from the biological sample plane on the solid foil. The materials which can be used as a solid foil may be preferably materials which can conform to a planar shape such as biological tissue or pieces of tissue. Thus, plastic may be preferable rather than hard materials such as glass. When observations are performed with visible rays, it is preferable to be transparent. When ultraviolet rays are used for observation, a property to transmit ultraviolet rays is preferable.

In a preferred embodiment, a mark related to a desired character of the sample (for example, a lesion or disease damage and the like) is attached to the solid foil in the sugar chain replica of the present invention. Thus, correlation with the desired character becomes easy.

In one aspect, the present invention provides a method for analyzing sugar chains on a sample comprising or expected to comprise sugar chains. The method comprises the steps of: a) locating a substance which can specifically interact with sugar chains on a surface of a two-dimensionally extended support, and contacting the surface on which the substance is not located with a solid foil; b) contacting the sample comprising or expected to comprise sugar chains with the solid foil; and c) analyzing sugar chains existing on a surface of the solid foil. Such a solid foil is the same as for the above-described sugar chain replica, and the method can be referred to as an analysis method using the sugar chain replica. The analysis method using the sugar chain replica can analyze the sugar chains while having the sample as two dimensional images as it is. Thus, the analysis method using the sugar chain replica of the present invention has usefulness in providing a two-dimensional analysis method which cannot be achieved by the conventional art. Herein, in the steps a) and b), the techniques are similar to production methods for the sugar chain replica as described above. For the sugar chain analysts in the above step c), as described in the present specification, various methods (for example, physical methods such as a physiological method such as mass spectrum, chemical method, biochemical method, biological method and the like) may be used. For example, such an analysis step may include ionizing the surface of the solid foil, and then performing mass spectrum analysis.

Preferably, such an analysis method further includes the steps of: marking the desired character of the sample; and correlating the mark and the sugar chains identified by the mass spectrum analysis. By including such steps, the desired character can be analyzed immediately and as a two-dimensional image.

In another aspect, the present invention provides an apparatus for analyzing sugar chains or a sugar chain-containing substance in a sample. The apparatus comprises: a) sugar chain-trapping carrier comprising a substance which can specifically interact with sugar chains; and b) means for identifying the sugar chains. The sugar chain-trapping carrier may further include a support. Such an apparatus can identify the sugar chains conveniently and reliably. Conveniently, a sample including any kind of sugar chains can be an object. Thus, the apparatus can be also produced as an automated apparatus. Such automation can be performed using techniques well-known in the art.

The sugar chain-trapping carrier included herein is as described in the present specification, and the preferred embodiments thereof can be appropriately used when they are suitable for the apparatus. The means for identifying the sugar chains can be any means using various methods (for example, physical method such as mass spectrum, chemical methods, biochemical methods, biological methods and the like). For miniaturizing the apparatus, it may be advantageous to use, for example, biochemical means (antibody, lectin or the like which specifically binds to sugar chains), or use enzymes such as glycosidase.

In another aspect, the present invention provides a device for analyzing sugar chains or a sugar chain-containing substance in a sample, comprising a support on which a substance which can specifically interact with sugar chains is located. Such a device may be in any shape or may have any size. Preferably, in this device, the substance which can specifically interact with sugar chains is arranged on the support in an array. More preferably, the device has a chip shape. When a device of chip shape is used, for example, a material with relatively low hardness such as nylon film or a material with high hardness such as glass may be used. When a nylon film or the like is used, results can be analyzed using a convenient analysis system. For analyzing a high density substance, it is preferable to use a material with hardness such as glass. Therefore, when it is desired to use the device as a sugar chain chip, it is genrally preferable to use a hard material such as glass as the support (or substrate).

In another aspect, the present invention provides a method for diagnosing or differentiating a subject. The method comprises the step of: a) analyzing sugar chains or a sugar chain-containing substance in a sample derived from the subject using the device according to the present invention. The device is the above-described device, preferably, the sugar chain-trapping carrier is arranged in an array, and more preferably, the device has a chip shape.

In a preferred embodiment, an analysis step performed in the method of diagnosis or determination of the present invention includes detecting a presence of an antibody and/or lectin to the sugar chains or sugar chain-containing substance.

In another aspect, the present invention provides a system for analyzing sugar chains or a sugar chain-containing substance in a sample. The system comprises: a) sugar chain-trapping carrier comprising a substance which can specifically interact with sugar chains; b) means for exposing the sugar chain-trapping carrier and the sample to the conditions of desired stringency; and c) means for identifying the sugar chains. The sugar chain-trapping carrier may further include a support. This system uses the sugar chain-trapping carrier of the present invention. Due to a property that the sugar chain-trapping carrier interacts with any sugar chains with no discrimination, the content ratio of the sugar chains and sugar chain-containing substance can be analyzed while the content ratio is maintained in the natural state by the above system. As such, the natural state can be reflected. Thus, for example, the condition of the subject, which can be determined by sugar chains, can be readily determined by a sample taken out of the subject. Alternatively, the sugar chains which reflect the state in nature are concentrated. Thus, it is possible to provide analysis values which can be effectively used in fields where biomolecules are involved, such as, medicines, agriculture, healthcare, food, cosmetics and the like. Such analysis values have significant effects in various aspects which require to faithfully reflect the types of original sugar chains since the sugar chain composition of the sample which forms a basis of data has substantially the same composition ratio as the original sugar chain binding state.

The a) sugar chain-trapping carrier comprising a substance which can specifically interact with sugar chains used in the system of the present invention is as described in the present specification, and its preferred embodiment can also be used in this system. The sugar chain-trapping carrier may further include a support.

For the b) means for exposing the sugar chain-trapping carrier and the sample to the conditions of desired stringency used in the present invention, techniques as described in the present specification can also be used, and its preferred embodiment can also be used in this system.

The c) means for identifying the sugar chains used in the system of the present invention may also be any kind of means, but may be means using various methods (for example, physical method such as mass spectrum, chemical, biochemical method, biological method and the like). For miniaturizing the apparatus, it may be advantageous to use, for example, biochemical means (antibody, lectin or the like which specifically binds to sugar chains), or enzymes such as glycosidase. Alternatively, when the system can have a large size, the means for identifying the sugar chains may be a mass spectrum analyzer.

In another aspect, the present invention provides a method for manufacturing an apparatus for analyzing sugar chains or a sugar chain-containing substance in a sample.

The method comprises the steps of: a) providing a substance which can specifically interact with sugar chains; and b) causing the substance which can specifically interact with sugar chains to interact with the support to produce a sugar chain-trapping carrier. Such a method has usefulness in that it provides an apparatus for analyzing sugar chains or sugar chain-containing substances in the sample, which has not existed conventionally. Preferably, the production method further includes the step of locating the sugar chain-trapping carrier to a container for housing.

In another aspect, the present invention provides a method for producing a sugar chain array. The method comprises the steps of: a) providing a support; b) locating a substance which can specifically interact with sugar chains in a desired arrangement. As the support, the support as described in the present specification can be used. The desired arrangement in this method may be a regular arrangement (for example, a grid), or it may be an irregular arrangement. Preferably, a regular arrangement may be used.

In another aspect, the present invention provides a method for analyzing a substance specifically binding to sugar chains or a sugar chain-containing substance in a sample. The method comprises the steps of: a) causing a sugar chain-trapping carrier comprising a substance which can specifically interact with sugar chains to interact with the sugar chains or sugar chain-containing substance in a fluid phase to fix; b) contacting the sugar chain-trapping carrier with the sample under the conditions expected that the substance specifically binding to sugar chains or a sugar chain-containing substance can react with the sugar chains; c) exposing a mixture of the sugar chain-trapping carrier and the sample to the conditions of desired stringency; and d) identifying the substance specifically binding to sugar chains or a sugar chain-containing substance. The sugar chain-trapping carrier may further include a support. In this method, contrary to the above-described method, unknown substances which specifically bind to the sugar chains or sugar chain-containing substances, which are expected to be included in the sample, can be analyzed. Such a substance specifically binding to sugar chains or a sugar chain-containing substance may be an antibody or lectin, but is not limited to these. When it is an antibody, the presence of sugar chains which are the target of the antibody is assumed in the subject. Thus, when it is determined by this method that such an antibody exists, it may be determined that the specific sugar chains exist within said subject. If it is known that such a sugar chain is related to a specific disease, disorder or condition, it is possible to diagnose such a disease, disorder or condition by the presence of the antibody. Therefore, the sample as used herein may derived from the subject expected to have a lesion. The techniques related to interactions of antibodies and lectin are also well known in the art, and those skilled in the art can readily perform the above determination and the like by combining such well-known techniques appropriately. A novel substance binding to sugar chains or sugar chain-containing substances, which is identified by this method of the present invention is also within the scope of the present invention. By using such a novel substance, the method, apparatus, system of the present invention can be implemented.

Therefore, in a preferred embodiment, the method of the present invention further includes the step of e) correlating the antibody or lectin and a disease, disorder, disease damage or condition related to its presence. Techniques for performing such a step are well-known in the art, and those skilled in the art can appropriately select and use such techniques.

In another aspect, the present invention provides a device for analyzing a substance specifically binding to sugar chains or a sugar chain-containing substance in a sample. The device comprises: a sugar chain-trapping carrier comprising a substance which can specifically interact with sugar chains in which the sugar chains or sugar chain-containing substance is fixed to the carrier by specific interaction. The sugar chain-trapping carrier may further include a support. Such a device can analyze an unknown substance specifically binding to sugar chains or sugar chain-containing substances, which is expected to be included in the sample. Such a method for fixing can be achieved by, for example, selecting covalent bonds as interaction.

In another aspect, the present invention provides a system for analyzing a substance specifically binding to sugar chains or a sugar chain-containing substance in a sample. The system comprises: a) a device comprising a sugar chain-trapping carrier comprising a substance which can specifically interact with sugar chains, in which the sugar chains or sugar chain-containing substances are fixed to the carrier by specific interaction; b) a sample introduction section; c) means for exposing a mixture of the sugar chain-trapping carrier and the sample to the conditions of desired stringency: and d) means for identifying the substance specifically binding to sugar chains or a sugar chain-containing substance. The sugar chain-trapping carrier may further include a support. Such a device can analyze an unknown substance specifically binding to sugar chains or sugar chain-containing substances, which are expected to be included in the sample.

The a) a device comprising a sugar chain-trapping carrier comprising a substance which can specifically interact with sugar chains, in which the sugar chains or sugar chain-containing substances are fixed to the carrier by specific interaction used in this system of the present invention can be produced as described above in the present specification. The sugar chain-trapping carrier may further include a support.

The b) sample introduction section used in this system of the present invention is as described in the present specification, and can be produced using techniques well known in the art.

The c) means for exposing a mixture of the sugar chain-trapping carrier and the sample to the conditions of desired stringency used in this system of the present invention is as described in the present specification, and can be produced using techniques well known in the art.

The d) means for identifying the substance specifically binding to sugar chains or a sugar chain-containing substance used in this system of the present invention is as described in the present specification, and can be produced using techniques well known in the art.

In another aspect, the present invention provides a sugar chain composition having an increased sugar chain content, obtained by contacting a sample comprising sugar chains with a substance which can specifically interact with sugar chains, and then separating sugar chains in the interacted sample. In such a sugar chain composition, sugar chains and/or sugar chain-containing substances which naturally exist are maintained, but substances other than sugar chains and sugar chain-containing substances are reduced. Thus, a composition which has a composition ratio which cannot be achieved by the conventional art such as through the use of lectin, antibodies and the like can be provided.

In a preferred embodiment, the substance which can specifically interact with sugar chains can specifically interact with any sugar chain at a certain level or higher. Thus, in such a sugar chain composition, sugar chains and/or the content ratio of sugar chain-containing substances which naturally exist is reflected, but substances other than sugar chains and sugar chain-containing substance are reduced. Thus, a composition which has a composition ratio that cannot be achieved by the conventional art such as through the use of lectin, antibodies and the like can be provided.

Such a sugar chain composition can be used as medicine. Such a sugar chain composition may also be used as food, healthcare food, cosmetics, polymeric material (biodegradable polymer and the like) or the like. Alternatively, such a sugar chain composition can be used as a surgical material (graft) or the like. As described in the present specification, forms for being used as medicines can be produced and used by using techniques well known in the art.

Further, in another aspect, the present invention provides an assay kit including the sugar chain composition of the present invention. Such an assay kit can provide convenient and precise results since the sugar chain composition faithfully reflect the sugar chain composition ratio of a source when the sugar chain is derived from said sample source.

Reference such as scientific documents, patents, and patent applications cited in the present specification are hereby incorporated by as if the entirety thereof are specifically described in the present specification.

The present invention has been illustrated with reference to the preferred embodiments of the present invention. However, the present invention should not be construed to be limited to such embodiments. It is noted that the scope of the present invention should be construed only by the scope of the claims. It is understood that those skilled in the art can carry out equivalent scope from the disclosure of the specific preferred embodiments of the present invention and based on the common technical knowledge. It is noted that patents, patent applications and documents cited in the present specification are herein incorporated by reference as if the contents themselves are specifically described in the present specification.

EXAMPLES

Hereinafter, the structure of the present invention will be described in more detail with reference to examples. However, the present invention is not limited to such examples.

Example 1

Synthesis of Photopolymerizable Hydroxyl Aminolipid 4

Figure 2:
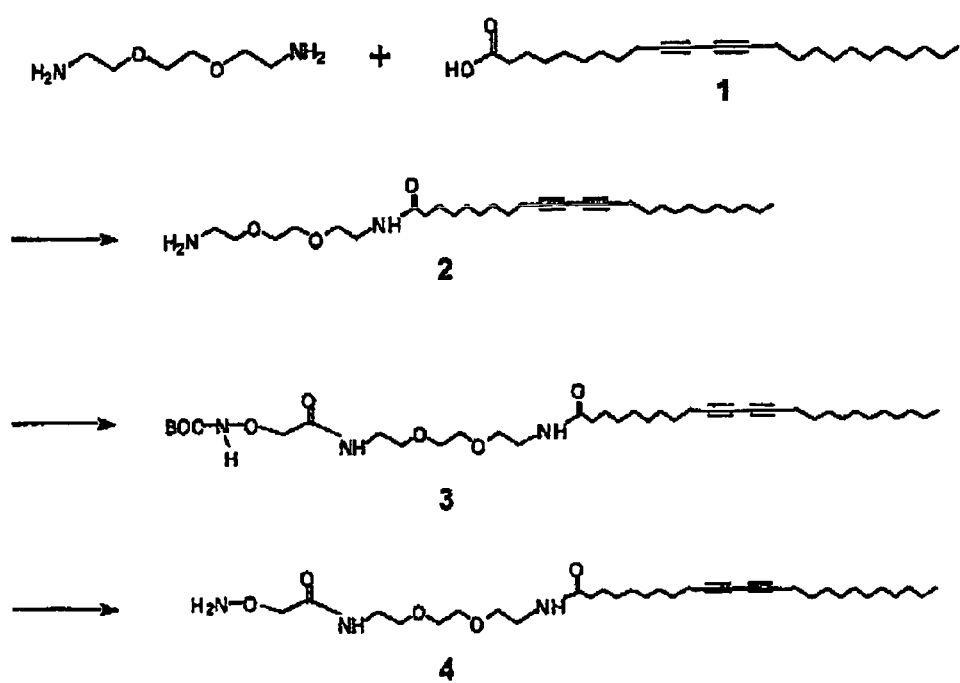
FIG. 2 is a diagram showing a synthetic pathway of the photopolymerizable hydroxyl aminolipid of the present invention.

Photopolymerizable hydroxyl aminolipid 4 of the present invention is synthesized following the synthesis path shown in FIG. 2.

(1.1 Synthesis of Compound 2)

10,12-pentacosadiynoic acid 1 (available from Lancaster, 1.6 g) and 2,2'-(ethylene dioxy)bis(ethylamine) (available from Aldrich, 5 ml) were dissolved in 300 ml of chloroform. 1-ethyl-3(3'-diethylaminopropyl)carbodiimide hydrochloride (available from Calbiochem, 3.3 g) was added at a temperature of 0° C. The reaction mixture was stirred at 0° C. for 1 hour, and then stirred at room temperature for 8 hours. The reaction solution was washed with water and saturated salt solution, and was dried by sodium sulphate. After the sodium sulphate was removed by filtration, the solvent was distilled away, and the residue was purified on a silica gel column (chloroform:methanol=7:3) to obtain object 2. The yield was 70%.

(1.2 Synthesis of Compound 3)

The compound 2 (1 g, 1.98 mmol) and Boc-amino-oxy-acetic acid (available from Calbiochem, 0.9 g) were dissolved in chloroform containing 5% of methanol. 1-ethyl-3(3'-diethylaminopropyl)carbodiimide hydrochloride (2.0 g, 10.4 mmol) was added to the solution at a temperature of 0° C.° and was then stirred at room temperature for 12 hours. The solution was washed with water and saturated salt solution, and dried on sodium sulphate. After the solvent was distilled away, purification on a silica gel column (chloroform:methanol=9:1) was performed and object 3 was obtained. The yield was 94%.

(1.3 Synthesis of Compound 4)

The compound 3 (0.5 g) was dissolved in dichloromethane (50 ml) at a temperature of 0° C., and trifluoroacetic acid (10 ml) was added. The solution was stirred at 0° C. for 5 hours, and then, toluene (10 ml) was added and all the solvent was distilled away. Quantitatively, object 4 was obtained. Identification of the compound was performed by NMR and Mass spectroscopy. $^1$H-NMR(500 MHz, CDCl$_3$) 6.456(s,1H), 4.41 (s,2H), 3.62-3.56(m,6H), 3.56-3.48(m,4H), 3.46-3.41(m, 2H), 2.214(t,J=6.94 Hz, 4H), 1.6-1.2(m,36H), 0.857(t,J=7.25 Hz, 3H); $^{13}$C-NMR(125 MHz, CDCl$_3$) 175.69, 157.90, 114.44, 77.633, 77.441, 72.465, 70.046, 70.011, 69.825, 69.212, 65.313, 65.233, 39.526, 39.0312, 36.334, 31.917, 29.644, 29.624, 29.608, 29.478, 29.338, 29.134, 29.097, 29.076, 28.893, 28.873, 28.762, 28.375, 28.303, 25.744, 22.685, 19.199, 19.156, 14.100; calculated value of ESI-Mass(pos)[M+H]+$C_{33}H_{60}N_3O_5$: 578.45, observed value 578.42.

Example 2

Production Method of Sugar Chain-Trapping Polymer

Figure 3:
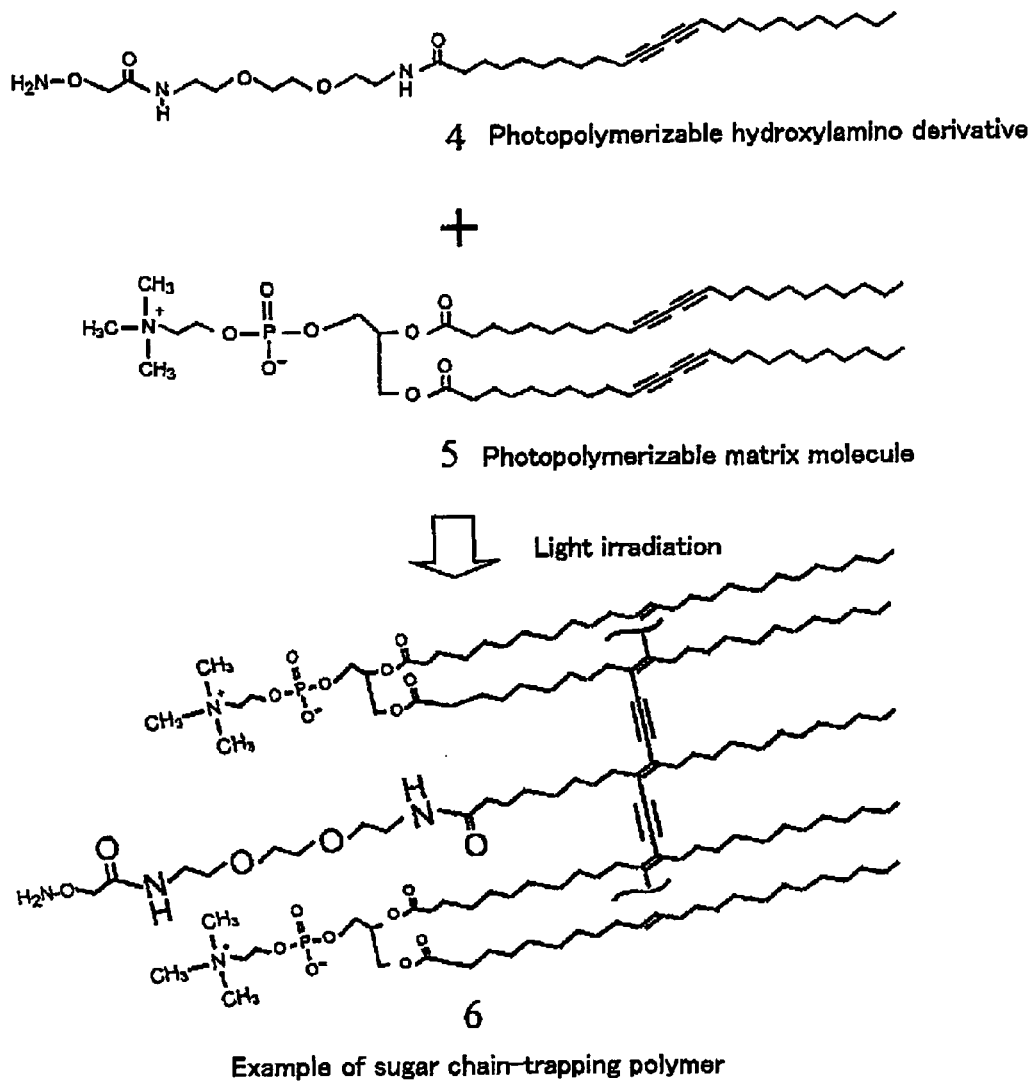
FIG. 3 is a diagram showing a preparation method of the sugar chain-trapping polymer of the present invention.
Figure 4:
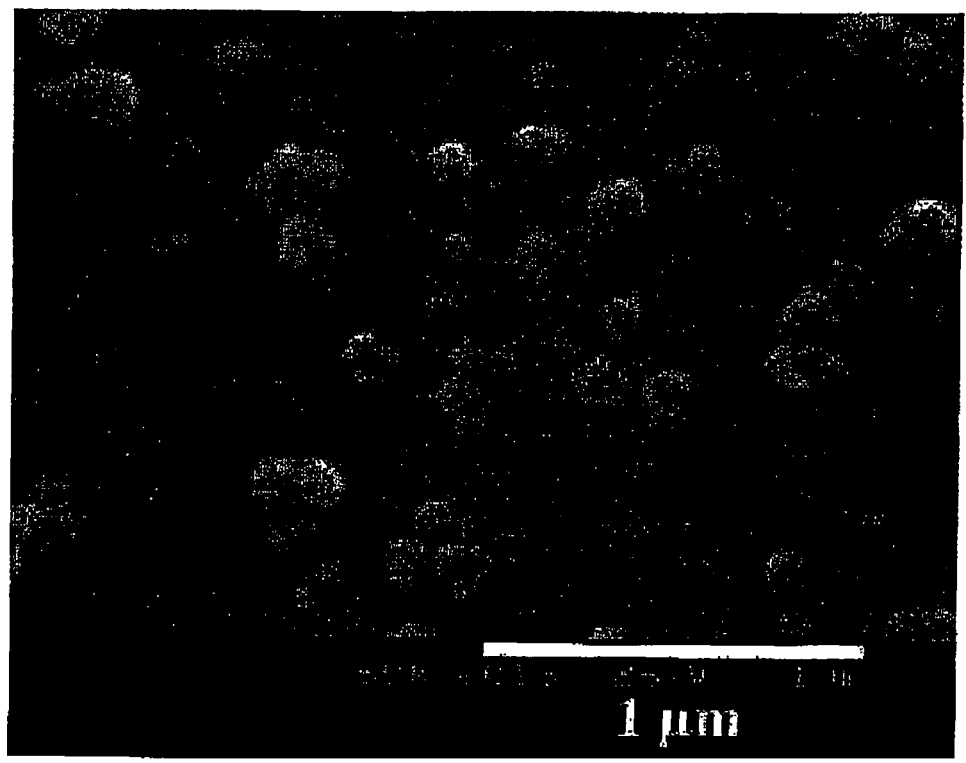
FIG. 4 is an electron micrograph of sugar chain-trapping polymer nanoparticles of the present invention.

The photopolymerizable hydroxyl aminolipid 4 synthesized in Example 1 (7 mg) and dipenta cosadiynoylphosphatidylcholine which is photopolymerizable matrix molecule 5 (30 mg) were dissolved in 10 ml of chloroform, and put into a recovery flask of 200 ml. The chloroform was distilled away by an evaporator, and 30 ml of ultrapure water was added to the lipid mixture which is a residue. After the mixture was heated at 70° C. for 10 minutes, it is subjected to an ultrasonic treatment for 15 minutes using an ultrasonic apparatus of a probe type, after which the solution is clear. The solution was rapidly cooled to 4° C., and the solution was degassed well by an aspirator. Then, the solution was transferred to a quartz conical flask, and irradiated with light by bringing an ultraviolet ray lamp (8 W, 100V) to a distance of 10 cm while being slowly bubbled with argon. Irradiation was performed for 30 minutes during which time the solution was maintained at 4° C. in a water bath. The solution, now having changed color from red to orange, was purified by passing it through a 450 micron filter, and the sugar chain-trapping polymer of ball shape was obtained (FIG. 3). The shape of the sugar chain-trapping polymer was confirmed by an electron microscope. The result of electron microscopy is shown in FIG. 4.

Example 3

Purification and Separation of a Sugar Chain-Trapping Polymer with Sugar Chains of Glycoprotein Liberated by Enzymes (3.1 Sugar Chain Pattern Analysis of Purified Human-Derived Immunoglobulin)
[Liberation of Sugar Chains]

Purified human-derived immunoglobulin (available from Sigma) was dissolved in 0.01 N hydrochloric acid aqueous solution, adjusted to pH 2 by using 0.1 N hydrochloric acid, and was subjected to heat treatment at 90° C. for 60 minutes. After the heat treatment, the solution was neutralized by an ammonium bicarbonate solution, and lyophilized. The lyophilized product was dissolved in an ammonium bicarbonate solution of 50 mM, trypsin of one-hundredths by the weight with respect to immunoglobulin was added thereto, and reaction was continued at 37° C. for 24 hours. Then, the mixture was heated at 90° C. for 15 minutes and cooled to room temperature. Then, N-glycosidase (enzyme derived from *Flavobacterium* is expressed at *E. coli*. available from Roche) of one unit per 1 mg of immunoglobulin was added, and the reaction continued at 37° C. for 24 hours. Then, the mixture is heated at 90° C. for 15 minutes to stop the reaction. 5 mg of immunoglobulin from the mixture was used for a sugar chain purification test.

[Sugar Chain Trapping and Separation and Purification]

Figure 5:
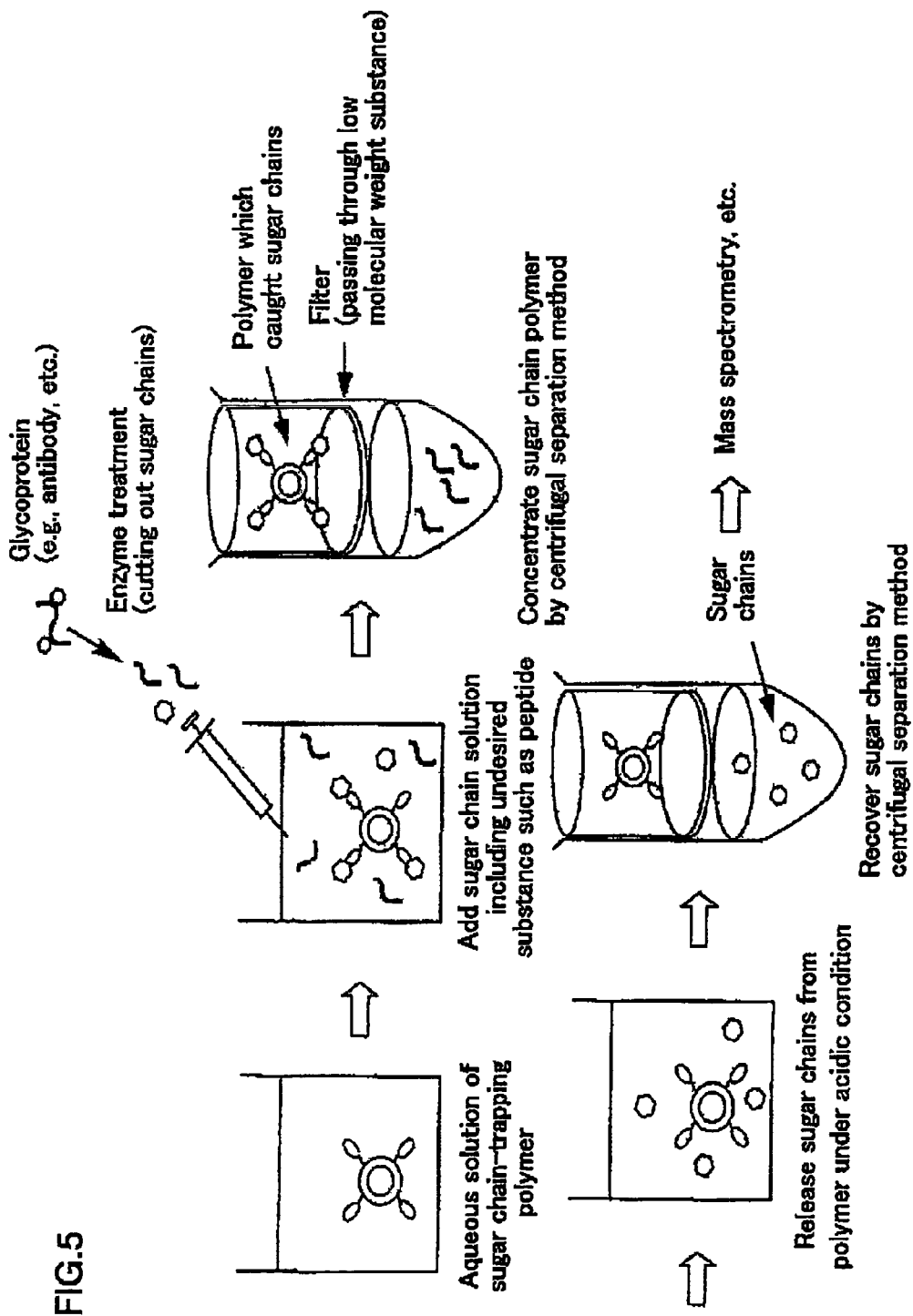
FIG. 5 is a schematic diagram of a separation and purification process using a sugar chain-trapping polymer.

FIG. 5 shows a schematic figure of a specific separation and purification process using the sugar chain-trapping polymer. To 800 μl of the sugar chain-trapping polymer solution prepared in Example 2, 10 μl of 3 N acetic acid buffer (pH 5.6) was added. Then, 200 μl of the solution of sugar chain mixture derived from immunoglobulin as described above (5 mg of human-derived immunoglobulin is dissolved in 1 ml of ammonium bicarbonate solution) was added thereto, 200 μl of methanol was added thereto, and the solution was left at 37° C. for 12 hours. Centrifugal filtration was performed for 40 minutes under the condition of 10,000 rotations/minute and temperature of 10° C. using a Microcon (available from Millipore). 200 μl of ultrapure water was added to the polymer concentrate, centrifugal filtration was again performed under the same conditions. 100 μl of ultrapure water was added to the concentrate (a few μl) to obtain a polymer concentrate.

[Release Process of Sugar Chains]

A proton type ion exchange resin (available from Aldrich, Amberlite IR-120) was added to the obtained polymer concentrate, and the mixture was stirred at 37° C. for 1 hour. The solution was subjected to centrifugal filtration for 30 minutes under the condition of 10,000 rotations/minute and temperature of 10° C. using a Microcon (available from Millipore), and the filtrate was recovered.

[Mass Spectrometry of Sugar Chains]

By performing mass spectrometry of the filtrate by using MALDI-TOF MS (available from Bruker, Biflex), six signals were obtained (not shown). As a matrix reagent for measurement, 2,5-dihydroxy benzoic acid (available from Fluka) is used. The structure of the sugar chains derived from an antibody used is known (N-binding type sugar chains), and the six mass spectrum signals are determined that they are all derived from sugar chains. Signals of MALDI-TOF MS before purification by sugar chain-trapping polymer are very complicated. Thus, it can be confirmed that sugar chains are selectively separated and purified.

[Comparison with HPLC]

Figure 6:
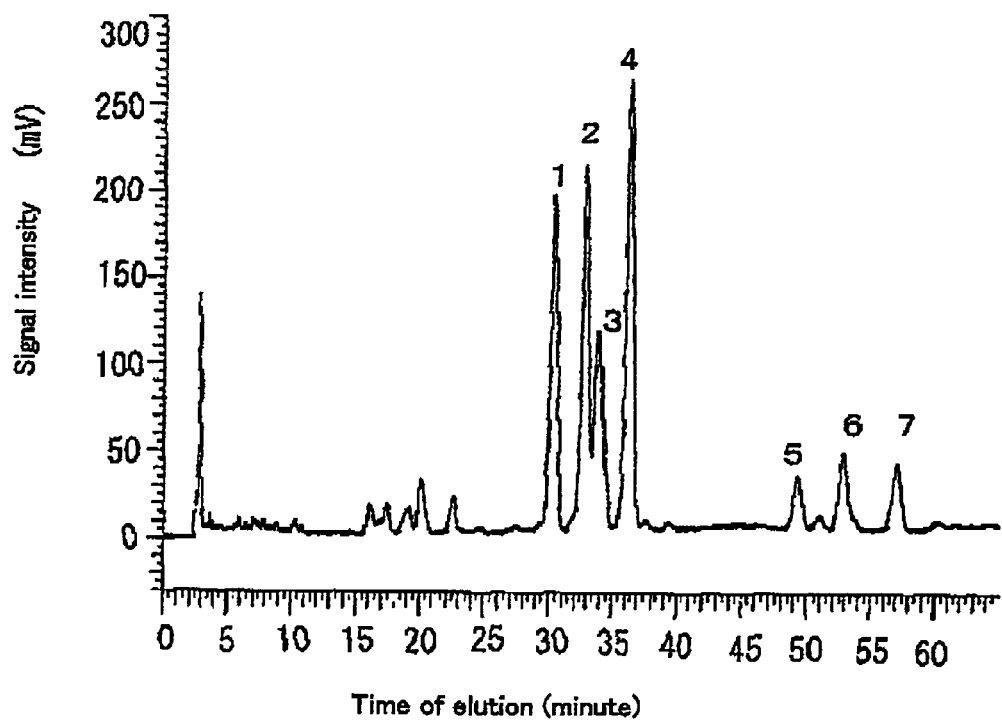
FIG. 6 is a diagram showing an analysis result by a reverse-phase system high performance liquid chromatography (HPLC) regarding sugar chains of purified human-derived immunoglobulin.
Figure 8:
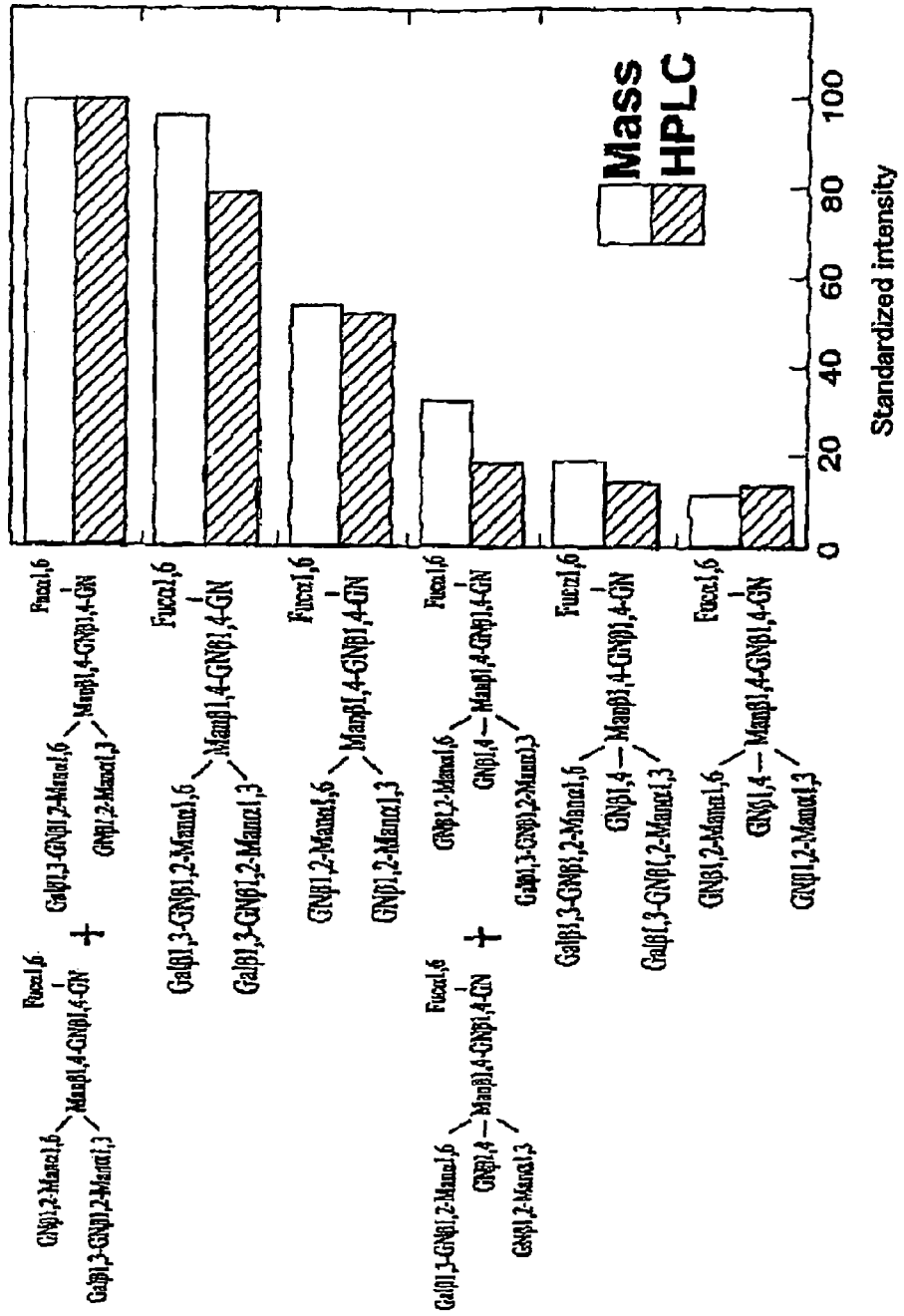
FIG. 8 is a diagram showing comparison of standardize intensity obtained by Mass method (MALDI-TOF MS) and HPLC method for each of the sugar chains of the purified human-derived immunoglobulin.

On the other hand, to 5 mg of immunoglobulin from the samples which are subjected to N-glycosidase treatment, 50 μg of pronase (available from Calbiochem) was added, and the reaction continued at 37° C. for 16 hours. Then, the mixture was heated at 90° C. for 15 minutes, to stop the reaction. The reactant was purified by gel filtration using bio gel (available from Bio-rad), sugar chains were bound to pyridylamine derivatives using 2-aminopyridine hydrochloric solution and sodium cyanotrihydroborate, and unreacted 2-aminopyridine were removed using Sephadex (available from Amersham Biotech). The sugar chains were analyzed by reverse-phase system column high performance liquid chromatography (FIG. 6). As already reported (Anal. Biochemistry, 163, 489-499, 1987), the composition of the sugar chains derived from immunoglobulin is considered to be as shown in FIG. 7, and it can be confirmed to match the mass spectrometry results mentioned above (FIG. 8).

(3.2 Sugar Chain Pattern Analysis of Ovalbumin)
[Liberation of Sugar Chains]

Ovalbumin (2 mg, available from Sigma) was dissolved in 0.5 ml of Tris buffer (pH 8.0), Chymotrypsine (0.2 mg) was added, and the mixture was left at 37° C. for 12 hours. After being incubated at 90° C. for 10 minutes, 20 units of N-Glycosidase P were added, and the mixture was left at 37° C. for 12 hours. Again, the mixture was left at 90° C. for 10 minutes, and then lyophillized to obtain a mixture of Ovalbumin and liberated sugar chains.

[Sugar Chain Trapping and Separation and Purification]

To the lyophilized Ovalbumin mixture, 1 ml of sugar chain-trapping particle aqueous solution (produced by photopolymerization from photopolymerizable hydroxyl aminolipid 4 (2.0 mg), photopolymerizable phosphoric acid type lipid 5 (8.5 mg)), 5 μl of acetic acid buffer (3M) of pH 5.2, and 200 μl of MeOH were added. After being stirred by a Vortex, insoluble components were removed by centrifugation (7000 rpm, 24° C., 10 minutes). A supernatant was left at 40° C. for 15 hours, and components which are not trapped by nanoparticles were removed by Spinfiltration (molecular weight fraction: 30,000).

[Release Process of Sugar Chains]

0.5 ml of pure water is added to concentrated sugar chain-trapping particles, then, 20 mg of ion exchange resin Amberlite (H+) and 0.1 ml of acetone were added, and the mixture was stirred for 12 hours. Sugar chains liberated from nanoparticles were recovered by Spinfiltration (molecular weight fraction: 30,000).

[Mass Spectrometry of Sugar Chains]

Figure 9:
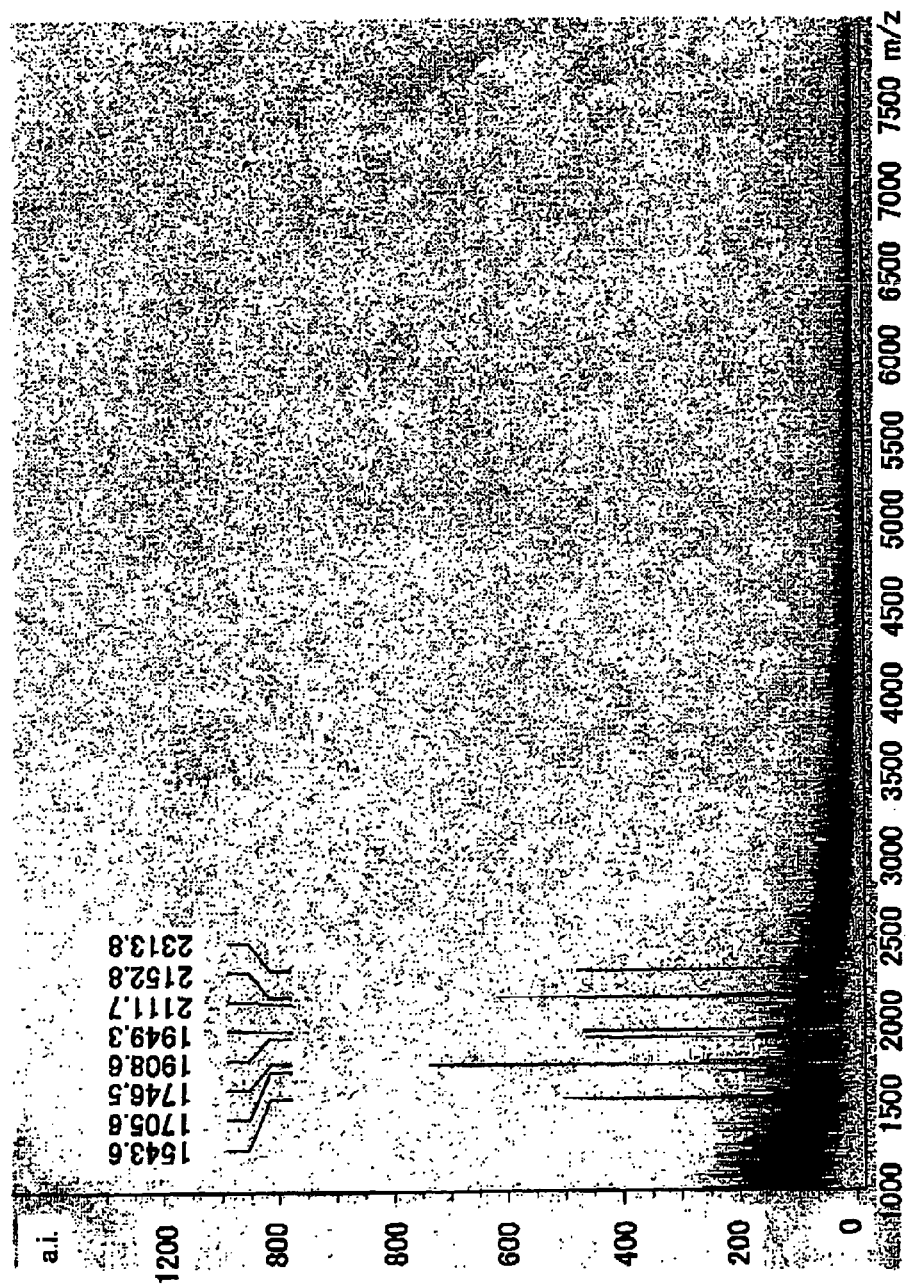
FIG. 9 is a diagram showing a sugar chain pattern of Ovalbumin purified by sugar chain-trapping nanoparticles. m/z of main peaks of FIG. 9 are 1543.6, 1705.6, 1746.5, 1908.6, 1949.3, 2111.7, 2152.8 and 2313.8 in an ascending order.

The filtrate was analyzed by MALDI-TOF mass spectrometry (FIG. 9). A signal derived from peptide is not observed, and only the signals derived from the sugar chains are observed (FIG. 9).

To the obtained purified sugar chains, Girard T (available from Sigma, a reagent for adding quaternary amine to sugar chains and commercially provided for improving signal sensitivity of sugar chains in MALDI-TOF) is added. 5 µl of pure water and 10 µl of 20 mM Girard T (80% MeOH Solution) were added to a sample (10 µl), and left at 90° C. for 1 hour. The obtained MALDI-TOF spectrum is shown in FIG. 10. In FIG. 10, more obvious signals of sugar chain pattern can be observed.

(3.3 Sugar Chain Pattern Analysis of Transferrin)

Figure 11:
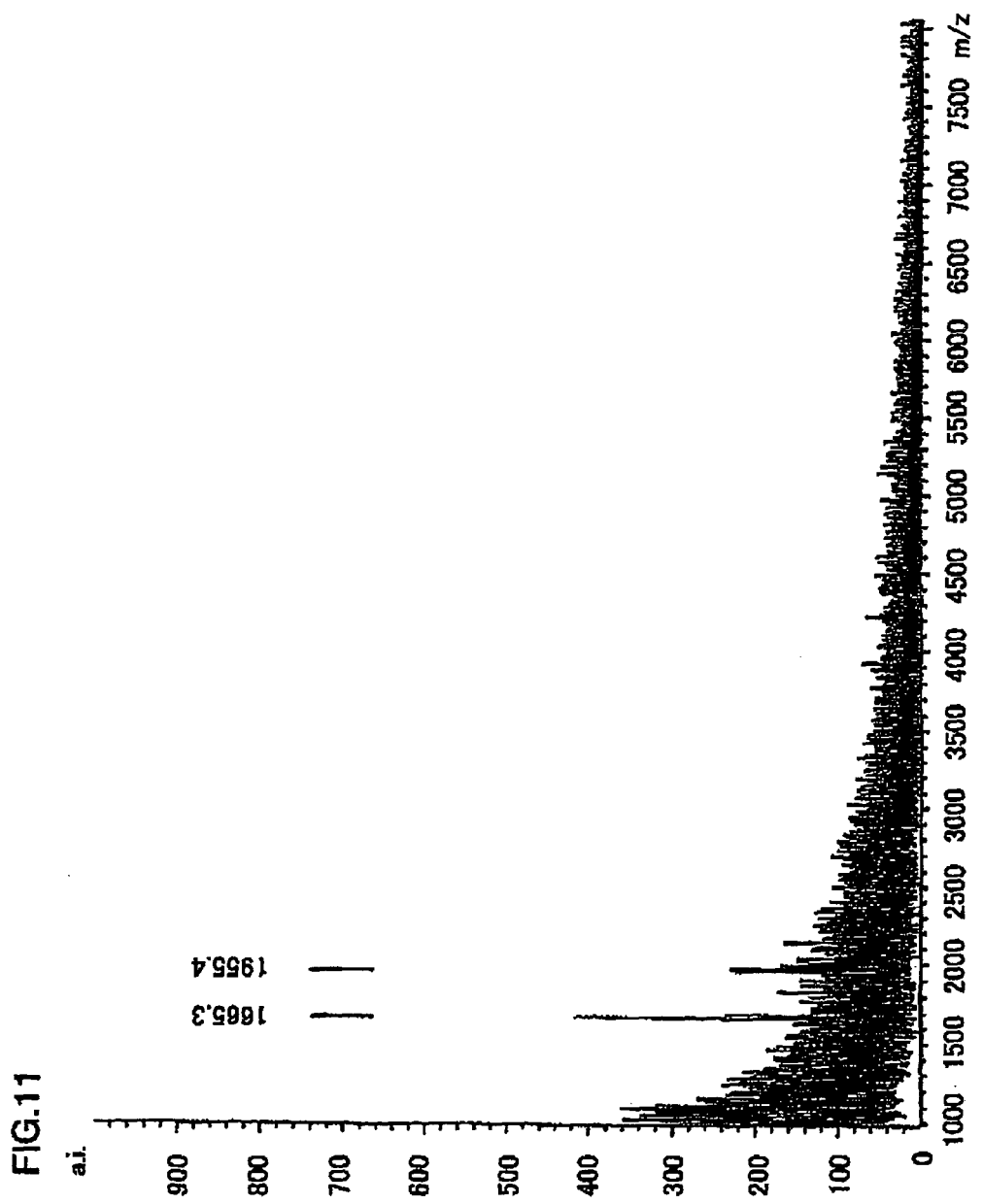
FIG. 11 is a diagram showing sugar chain pattern of Transferrin purified by sugar chain-trapping nanoparticles. m/z of main peaks of FIG. 11 are 1665.3 and 1955.4 in an ascending order.
Figure 12:
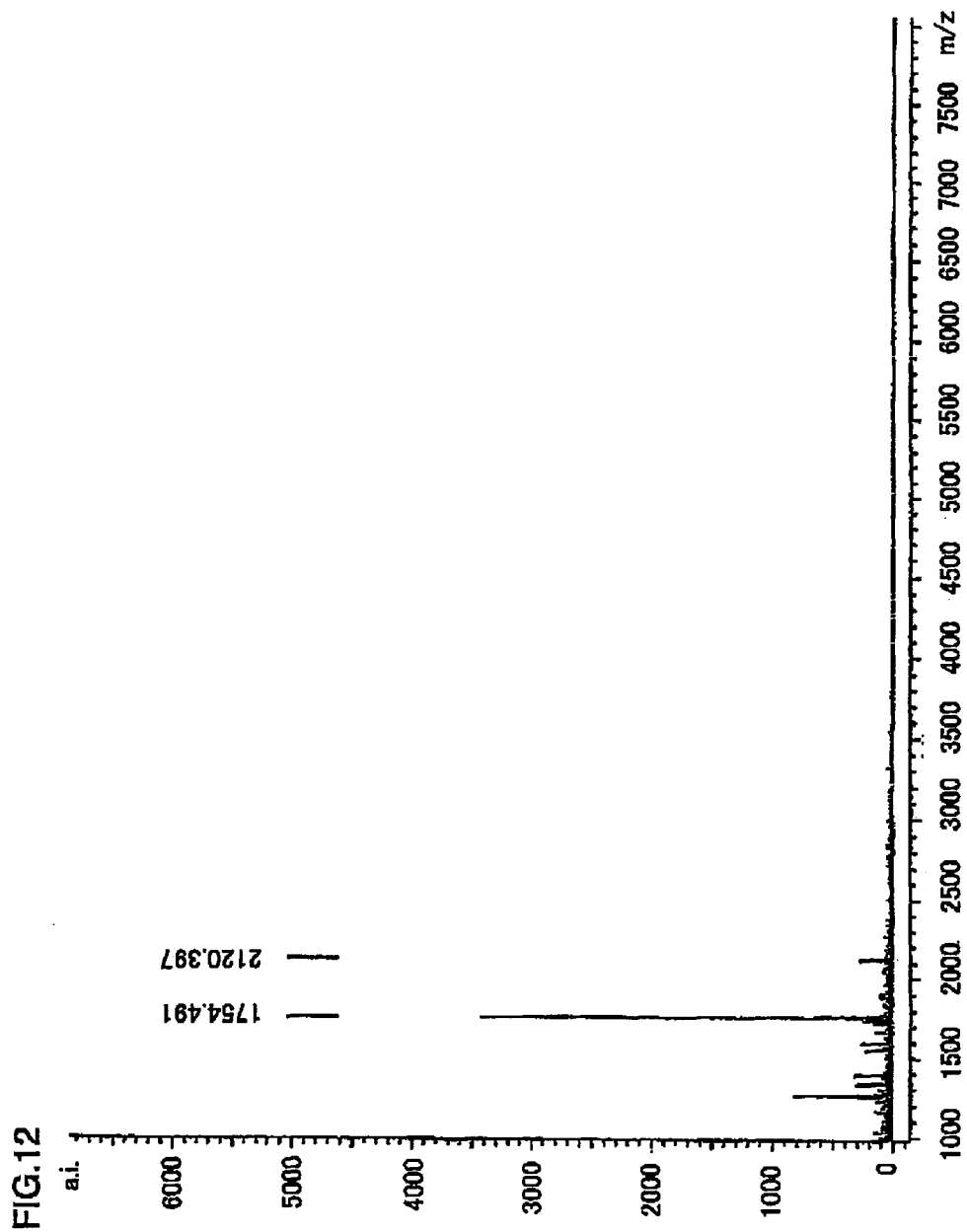
FIG. 12 is a diagram showing MALDI-TOF spectrum after a sample of FIG. 11 is treated with Girard T reagent. m/z of main peaks of FIG. 12 are 1754.491 and 2120.397 in an ascending order.

A similar experiment is performed for Transferrin, and signals of the sugar chain pattern were obtained (FIG. 11). Similarly to the case described in the above section 3.2, MALDI-TOF MS spectrum after the sample of FIG. 11 is treated by the Girard T reagent is shown in FIG. 12. In FIG. 12, more obvious signals of sugar chain pattern can be observed.

(3.4 Sugar Chain Pattern Analysis of Glycoprotein Included in Human Blood Serum)

Figure 13:
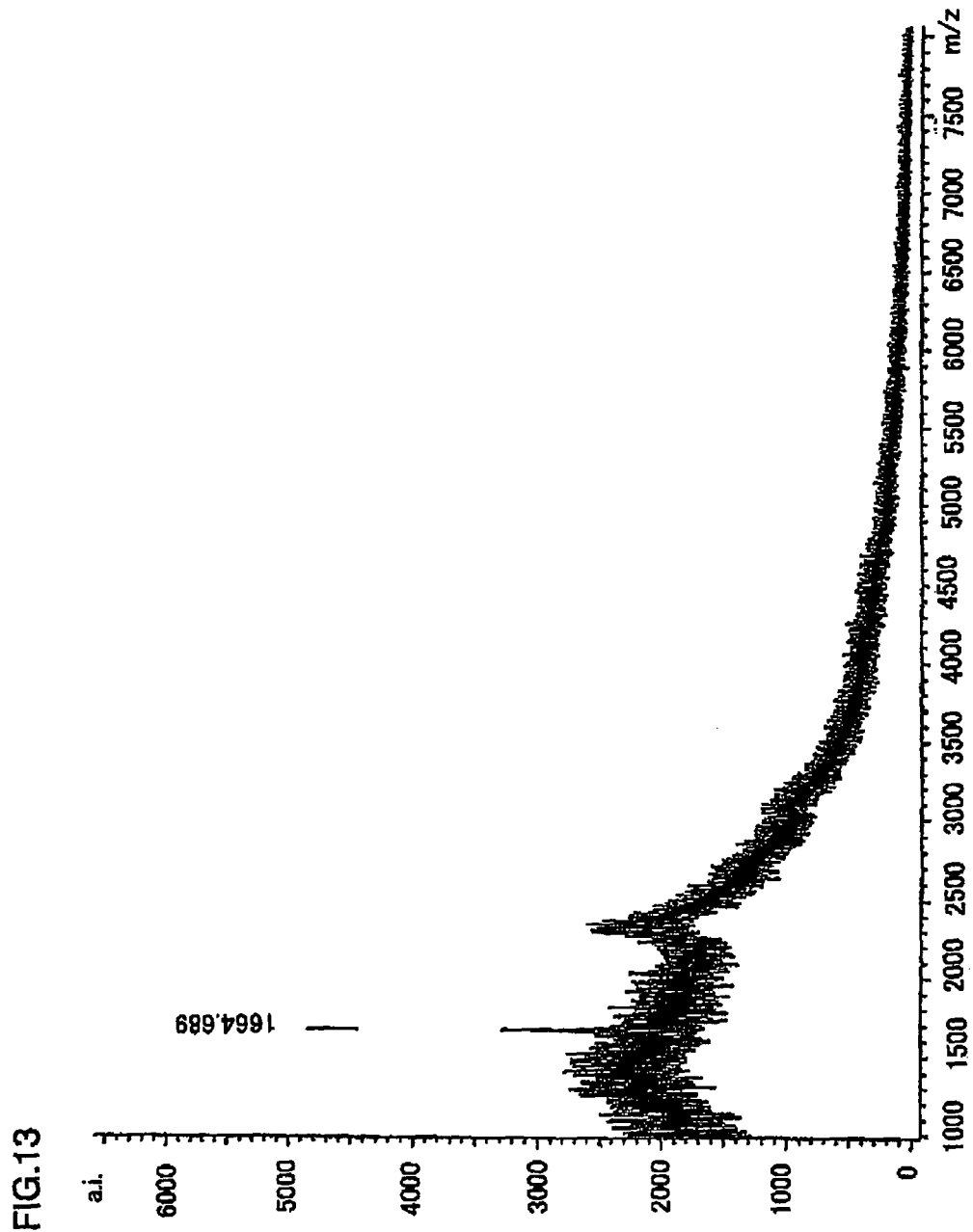
FIG. 13 is a diagram showing a sugar chain pattern obtained by purifying human blood serum by sugar chain-trapping nanoparticles. m/z of main peak of FIG. 13 is 1664.689.
Figure 14:
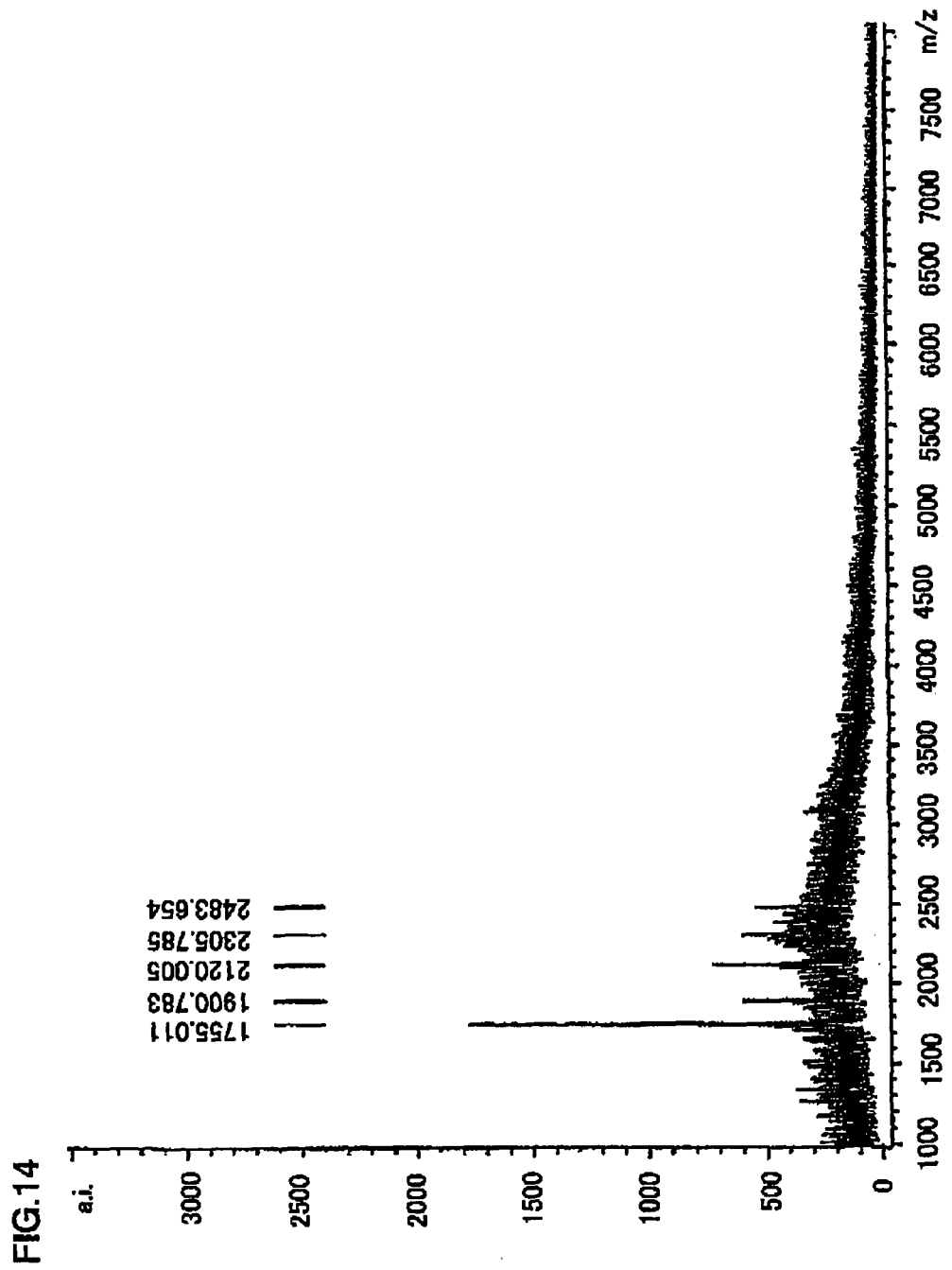
FIG. 14 is a diagram showing spectrum indicating that MALDI-TOF sugar chain-trapping polymer after treating the sample of FIG. 13 by Girard T reagent, can specifically bind to sugar chains. m/z of main peaks of FIG. 14 are 1755.011, 1900.783, 2120.005, 2305.785 and 2483.654 in an ascending order.

Lyophilized human blood serum was bought from Sigma. Since blood serum includes liberated glucose, dried blood serum (193 mg) was dissolved in 10 ml of Acetate buffer (pH 5.2, 20 mM). Then, 1.82 mg of glucose oxidase is added thereto, and the mixture was stirred for 30 minutes at 35° C. while being bubbled with air. The following operations are the same as those for the above-described glycoprotein. The pattern of the obtained human blood serum glycoprotein sugar chains is shown in FIG. 13. Similarly to the case described in the above section 3.2, MALDI-TOF MS spectrum after the sample of FIG. 13 is treated by the Girard T reagent is shown in FIG. 14. In FIG. 14, more obvious signals of sugar chain pattern can be observed.

Example 4

Confirmation of Recovery Specific to Sugar Chains Using Sugar Chain-Trapping Polymer

[Sugar Chains Trapping Process]

To 1 ml of acetic acid buffer (1 mg/ml) of sugar chain-trapping polymer 6, a mixture of alpha 1-3, alpha 1-6 mannotriose (available from Dextran laboratories, 300 micrograms) and alpha 1-3, alpha 1-6 mannotriose having a reducing terminal methylated (available from Dextran laboratories, 200 micrograms) was added, and left at 25° C. for 12 hours. The solution was divided to two Microcons (available from Millipore) (500 µl each), and centrifugal filtration was performed under the condition of 10,000 rotations/minute and temperature of 10° C. for 40 minutes. 200 µl of ultrapure water was added to the polymer concentrate, and centrifugal filtration was performed again under the same conditions. This operation was repeated twice. 100 µl of ultrapure water was added to the concentrate (a few µl) to obtain a polymer concentrate which traps the sugar chains.

[Sugar Chain Release Process]

A proton type ion exchange resin (available from Aldrich, Amberlite IR-120) was added to the obtained polymer concentrate, and the mixture was stirred at 37° C. for 1 hour. The solution was subjected to centrifugal filtration for 30 minutes under the condition of 10,000 rotations/minute and temperature of 10° C. using a Microcon (available from Millipore), and the filtrate was recovered.

[Mass Spectrometry]

Figure 15:
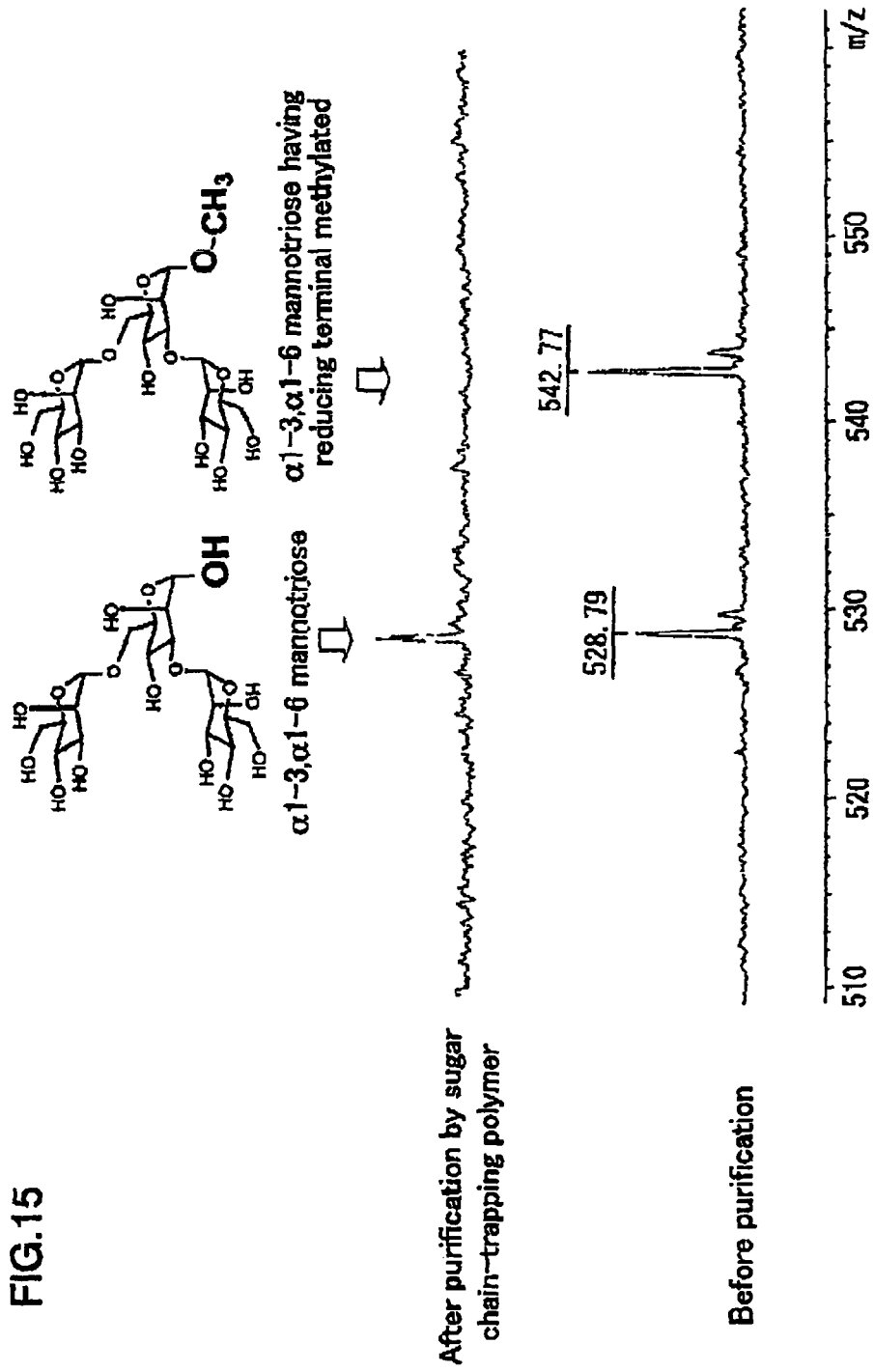
FIG. 15 shows mass spectrometry results indicating that the sugar chain-trapping polymer can specifically bind to sugar chains.

As a matrix reagent, 2,5-dihydroxy benzoic acid (10 mg/ml, available from Fluka) is used, and a filtrate was subjected to mass spectrometry by MALDI-TOF MS (available from Bruker, Biflex). The result is shown in FIG. 15. A signal derived from "alpha 1-3, alpha 1-6 mannotriose having a reducing terminal methylated" which cannot bind to sugar chain-trapping polymer because it is protected by methyl group is not observed. This results shows that the sugar chain-trapping polymer can specifically bind to sugar chains.

Example 5

Figure 16:
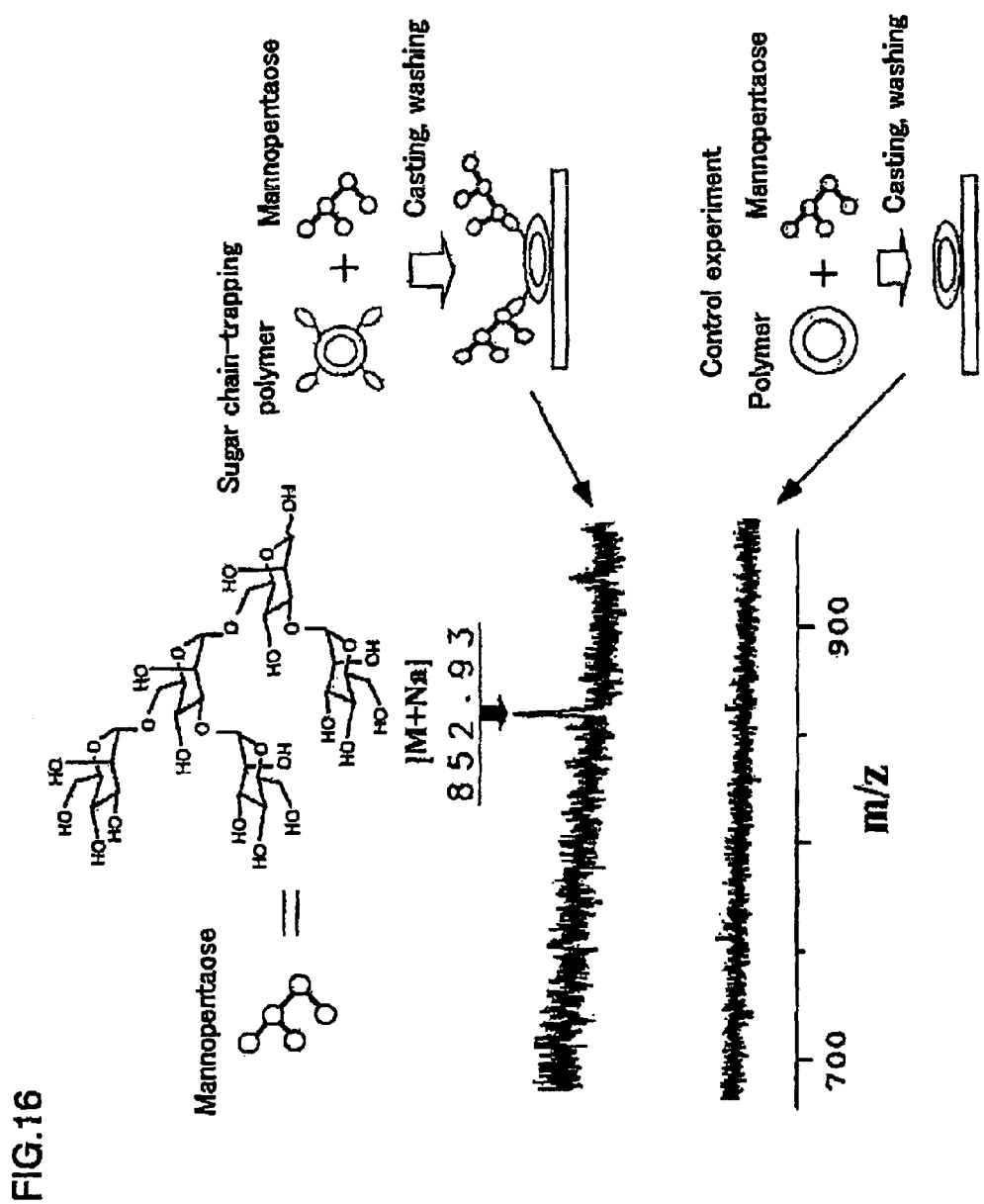
FIG. 16 is a diagram showing reduction in the separation and purification process for sugar chains by a cast method.

Reduction of Separation and Purification Process for Sugar Chains by Cast Method Mannopentaose (Available from Funakoshi Co., Ltd., 1 mg) was added to 5001 µl of acetic acid buffer (1 mg/ml) of sugar chain-trapping polymer 6. 100 µl of methanol is added thereto, and the mixture is left at 25° C. for 12 hours. An aqueous solution was casted to a plate of a MALDI-TOF MS, and a solvent was evaporated naturally. The plate casted with the polymer is rinsed well in water to remove unreacted sugar chains. As a matrix reagent, 10% trifluoro acetic acid aqueous solution (necessary for liberating sugar chains from the polymer), including 2,5-dihydroxybenzoic acid (10 mg/ml), is mounted to the cast film. After all the solvent was evaporated naturally, mass spectrometry measurement was performed. Signals derived from mannopentaose were obtained (FIG. 16). As a control experiment, a polymer which is photopolymerized with lipid 5, which does not have a sugar chain trapping capability, is subjected to the same experiment. In the control experiment, signals derived from mannopentaose were not obtained (FIG. 16). It is found that, by using a sugar chain-trapping polymer as a cast film, the separation and purification process for the sugar chains can be reduced to only washing with water.

Example 6

Production Method of Replica Production Plate Having Sugar Chain-Trapping Polymer Coated on Surface A replica production plate is produced by using a Langmuir-Blodgett (LB) method which is a standard method. Amphiphilic film-forming molecules in which hydrophilic groups and hydrophobic groups are balanced forms a stable monolayer on a surface of water. The monolayer is transferred to a surface of the substrate to produce a replica production plate. Specifically, photopolymerizable hydroxylamino derivative 4 (7 mg) and dipenta cosadiynoylphosphatidylcholine which is photopolymerizable matrix molecule 5 (30 mg) were dissolved in 10 ml of chloroform. A monolayer was developed as follows: a development solution is dissolved in a chloroform solvent, and the solution is dropped little by little (the volume of the drops of the solution is 40-200 μl) and developed using a microsyringe (100 μm) inside a frame produced by diagonally cutting edges of 4 straws (made of polypropylene, external diameter of 6 mm), arranging the straws into a rhombic shape with the pointed side of the ends adjacent to each other inside, and also coupling with Teflon (Trademark) tape such that straws deform flexibly, in a clean bath at 10-25° C. Then, an ultraviolet ray lamp (8 W, 100V) is brought to a distance of 10 cm for irradiating light and polymerization. Then, a cover glass for microscopic observation was contacted with the monolayer, and dried to obtain the replica production plate.

Example 7

Sugar Chain Replica Production Method Using Replica Production Plate

A breast cancer specimen, extracted and frozen during microscopic observation surgery, was cut to have thickness of 4 microns using a freezing microtome at −25° C., and hematoxylin eosin staining was performed using a normal method. After drying, a monolayer surface of the replica production plate produced in Example X1 is laid on a tissue section side so as to cover the tissue section and is fixed by an attachment adhering tape. By using a microscope, an observation lesion site is appropriately marked with super-fine oil-base felt pen or the like. A microsyringe is used to inject a hydrazine solution or glycosidase solution into a gap between the replica production plate and a slide glass, and the specimen brought into reaction in a temperature-controlled room at 25-38° C. The sugar chains of the surface of the tissue section is transcribed on the replica production plate. The sugar chains obtained by transcription is subjected to mass spectrometry by irradiated laser to the previously marked site using the method of Example 4.

Example 8

Sugar Chain Array

Detection of antibody by sugar chain fixed array.
Ovarian cancer-derived cells including sugar chains (patients which have already been differentiated whether malignant or benign according to the following document by Chien et al. are isolated, D X Chien, P E. Schwartz, CA125 Assay for detecting malignant uteres cancer. Gynecology, 75(4): 701-704, 1990.) Saliva of patients expected to include glycol protein composite CA125 which is recognized as a marker of ovarian tumors was collected. From each saliva fraction molecular weights of 10000 or higher were fractionated and concentrated using a cartridge column. These were distilled with PBS (1000, 200, 40, 10, 1, 0.1 ng/μl as glycoproteins, 1 μl for each), and the sugar chains were treated with a hydrazine solution and adhered on points on the replica production plate produced in Example X1 so as to form an array. Immediately after adhering to points on a solid phase carrier, it was left at 25° C. in a moisture chamber for 1 hour. Then, blocking treatment was performed by immersing into 1% BSA/0.05% Tween 20-PBS(PBS-T) for 1 hour, and a sugar chain array was obtained. To the sugar chain array anti-CA125 monoclonal antibody was added, and incubated in a moisture chamber at 25° C. for 1 hour. Next, the array was washed with PBS-T three times, rinsed with PBS and then dried. The obtained reaction array was labeled using fluorescence label anti-IgG antibody, rinsed with PBS and then dried. Then, the fluorescence intensity of the array surface was measured by a scanning apparatus. General molecular biological methods such as labeling can be performed in accordance with any of the methods described in: "Molecular Cloning-Laboratory Manual", second edition, Sambrook, Fritschand Maniatis (Cold Spring Harbor Laboratory, 1989); or "Latest protocol of molecular biology", volumes 1-3, F M Asubel, R Brentand, R E Kingston ed., John Wiley Publishing, 1998.

The present invention has been illustrated with reference to the preferred embodiments of the present invention. It is noted that the scope of the present invention should be construed only by the scope of the claims. It is noted that patents, patent applications and documents cited in the present specification are herein incorporated by reference as if the contents themselves are specifically described in the present specification.

INDUSTRIAL APPLICABILITY

According to the methods of the present invention, by efficiently separating, purifying or concentrating composite glycolipids such as glycoproteins, glycolipid and the like derived from cells or biological samples, and previously taking components such as mingling protein, lipids and the like, direct analysis methods such as mass spectrometry become easy. Further, it becomes possible to transfer sugar chains derived from a pathologic section as a two-dimensional image. For contacting the sugar chain-trapping polymer disclosed by the present invention with a living organism surface which has been subjected to an appropriate pre-treatment in combination with in vivo enzymes or the like, it becomes possible to fractionate sugar chains derived from the lumen of cells of vessels attached to a glandular system which has been impossible to collect previously (lactiferous duct, bile duct or the like). The fractionated sugar chain composition can be used as medicines such as vaccines, health foods, medicines having reduced residue proteins or lipids with less antigency, and less allergen food.

The invention claimed is:
1. A substance which can specifically interact with sugar chains, the substance having a formula X—Y—Z,
wherein X is selected from the group consisting of

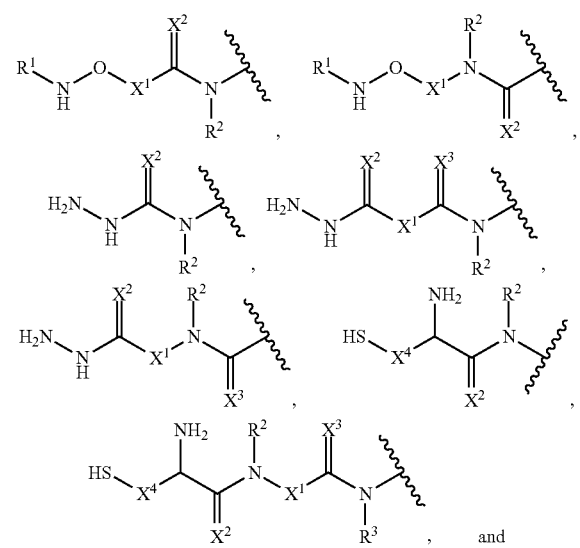

and

-continued

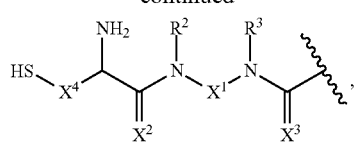

wherein $X^1$ is substituted or unsubstituted alkylene or substituted or unsubstituted alkenylene, $X^2$ and $X^3$ are independently oxygen or sulfur, $X^4$ is methylene or ethylene, $R^1$ is hydrogen or alkyl, and $R^2$ and $R^3$ are independently hydrogen or alkyl, wherein the alkylene of $X^1$ may comprise one or more atoms selected from oxygen and sulfur;

wherein when X is

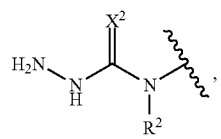

$X^2$ is oxygen and Y is a single bond or an optionally substituted $C_3$-$C_{12}$ alkylene in which at least one moiety may intervene, which intervening moiety is selected from the group consisting of —O—, —S—, —S—S—, —N($R^a$)—C(=O)—, —C(=O)—N($R^b$)—, and phenylene which may be substituted, wherein $R^a$ and $R^b$ are independently hydrogen or alkyl;

wherein when X is

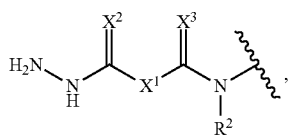

$X^1$ is substituted or unsubstituted $C_2$-$C_{12}$ alkylene or substituted or unsubstituted alkenylene, and wherein when X is

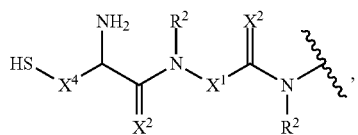

$R^2$ is alkyl;

Y is a single bond; or an optionally substituted alkylene in which at least one moiety may intervene, which intervening moiety is selected from the group consisting of —O—, —S—, —S—S—, —N($R^a$)—C(=O)—, —C(=O)—N($R^b$)—, and phenylene which may be substituted, wherein $R^a$ and $R^b$ are independently hydrogen or alkyl; and Z is a polymerizable functional group comprising a moiety selected from the group consisting of

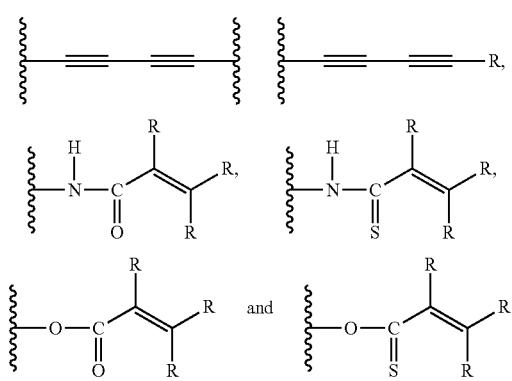

wherein each R is independently hydrogen or alkyl.

2. The substance according to claim 1, which is bindable to a support by either a covalent bond or a non-covalent bond.

3. A substance that can specifically interact with sugar chains, the substance having a formula X—Y—Z, wherein X is selected from the group consisting of

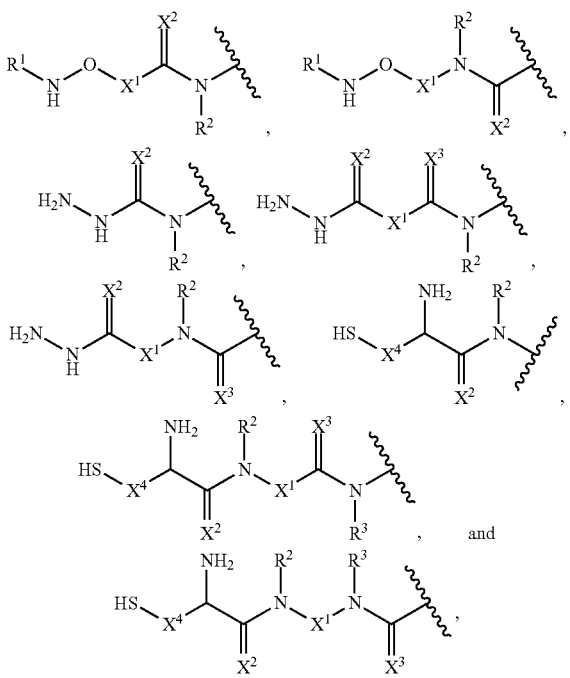

wherein $X^1$ is substituted or unsubstituted alkylene or substituted or unsubstituted alkenylene, $X^2$ and $X^3$ are independently oxygen or sulfur, $X^4$ is methylene or ethylene, $R^1$ is hydrogen or alkyl, and $R^2$ and $R^3$ are independently hydrogen or alkyl, wherein the alkylene of $X^1$ may comprise one or more atoms selected from oxygen and sulfur;

wherein Y is a single bond; an optionally substituted alkylene in which at least one moiety selected from the group consisting of —O—, —S—, —S—S—, —N($R^a$)—C(=O)—, —C(=O)—N($R^b$)—, and phenylene which may be substituted, may intervene, wherein, $R^a$ and $R^b$ are independently hydrogen or alkyl; and wherein Z is selected from the group consisting of

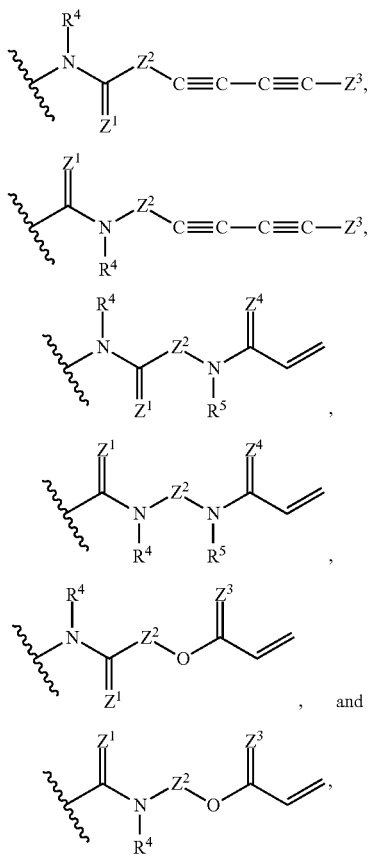

, and

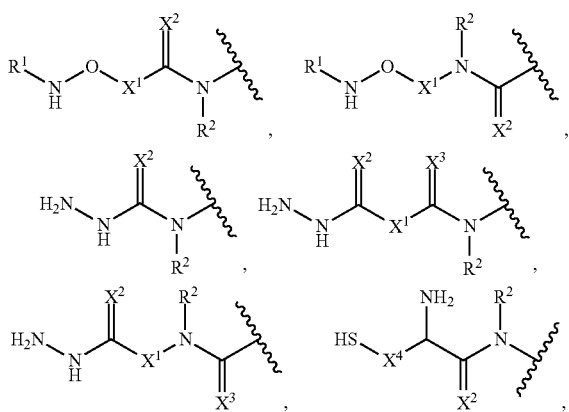

wherein $Z^1$ is oxygen or sulfur, $Z^2$ and $Z^3$ are independently optionally substituted alkylene in which phenylene may intervene, or optionally substituted alkenylene in which phenylene may intervene, $Z^4$ is oxygen or sulfur, $R^4$ and $R^5$ are independently hydrogen or alkyl.

4. A polymer obtained by polymerizing the substance of claim 1 having the formula X—Y—Z.

5. A substance which can specifically interact with sugar chains, the substance having a formula X—Y—Z, wherein X is selected from the group consisting of

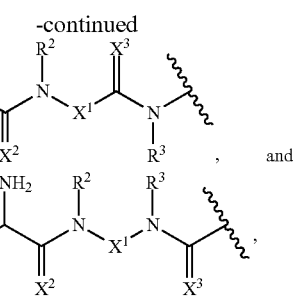

, and wherein $X^1$ is substituted or unsubstituted alkylene or substituted or unsubstituted alkenylene, $X^2$ and $X^3$ are independently oxygen or sulfur, $X^4$ is methylene or ethylene, $R^1$ is hydrogen or alkyl, and $R^2$ and $R^3$ are independently hydrogen or alkyl, wherein the alkylene of $X^1$ may comprise one or more atoms selected from oxygen and sulfur;

wherein when X is

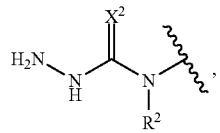

$X^2$ is oxygen and Y is a single bond or an optionally substituted $C_3$-$C_{12}$ alkylene in which at least one moiety may intervene, which intervening moiety is selected from the group consisting of —O—, —S—, —S—S—, —N($R^a$)—C(=O)—, —C(=O)—N($R^b$)—, and phenylene which may be substituted, wherein $R^a$ and $R^b$ are independently hydrogen or alkyl, wherein the alkylene of Y is optionally substituted with alkyl, cycloalkyl, alkenyl, cycloalkenyl, alkynyl, alkoxy, unsubstituted carbocyclic group, heterocyclic group, halogen, hydroxy, thiol, cyano, nitro, amino, carboxy, carbamoyl, acyl, acylamino, thiocarboxy, amide, substituted carbonyl, substituted thiocarbonyl, substituted sulfonyl or substituted sulfinyl;

and wherein when X is

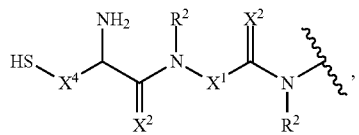

$R^2$ is alkyl;

Y is a single bond; or an optionally substituted alkylene in which at least one moiety may intervene, which intervening moiety is selected from the group consisting of —O—, —S—, —S—S—, —N($R^a$)—C(=O)—, —C(=O)—N($R^b$)—, and phenylene which may be substituted, wherein $R^a$ and $R^b$ are independently hydrogen or alkyl, wherein the alkylene of Y is optionally substituted with alkyl, cycloalkyl, alkenyl, cycloalkenyl, alkynyl, alkoxy, unsubstituted carbocyclic group, heterocyclic group, halogen, hydroxy, thiol, cyano, nitro, amino, carboxy, carbamoyl, acyl, acylamino, thiocarboxy, amide, substituted carbonyl, substituted thiocarbonyl, substituted sulfonyl or substituted sulfinyl; and Z is a polymerizable functional group comprising a moiety selected from the group consisting of
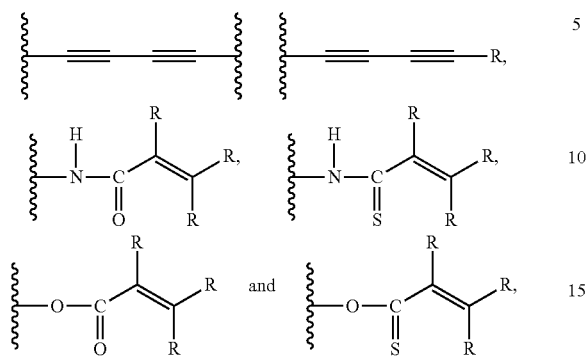
wherein each R is independently hydrogen or alkyl.
* * * * *